(12) United States Patent
Piller et al.

(10) Patent No.: US 7,723,570 B2
(45) Date of Patent: May 25, 2010

(54) EDIBLE VACCINES EXPRESSED IN SOYBEANS

(75) Inventors: Kenneth John Piller, Davidson, NC (US); Kenneth Lee Bost, Davidson, NC (US)

(73) Assignee: SoyMeds, Inc., Davidson, NC (US)

(*) Notice: Subject to any disclaimer, the term of this patent is extended or adjusted under 35 U.S.C. 154(b) by 790 days.

(21) Appl. No.: 11/249,182

(22) Filed: Oct. 12, 2005

(65) Prior Publication Data

US 2007/0192905 A1    Aug. 16, 2007

Related U.S. Application Data

(60) Provisional application No. 60/617,792, filed on Oct. 12, 2004.

(51) Int. Cl.
*C12N 15/82* (2006.01)
*A01H 5/00* (2006.01)
*A61K 39/085* (2006.01)
*A61K 47/00* (2006.01)

(52) U.S. Cl. .................. 800/288; 800/295; 800/312; 800/278; 800/294; 424/439; 424/184.1; 424/192.1; 424/237.1

(58) Field of Classification Search ............... None
See application file for complete search history.

(56) References Cited

U.S. PATENT DOCUMENTS

| | | | |
|---|---|---|---|
| 5,861,277 A | 1/1999 | Rose et al. | |
| 5,889,189 A | 3/1999 | Rodriguez | |
| 5,914,451 A | 6/1999 | Martinell et al. | |
| 5,968,830 A | 10/1999 | Dan et al. | |
| 6,034,298 A | 3/2000 | Lam et al. | |
| 6,136,320 A | 10/2000 | Arntzen et al. | |
| 6,194,560 B1 | 2/2001 | Arntzen et al. | |
| 6,392,121 B1 | 5/2002 | Mason et al. | |
| 6,395,964 B1* | 5/2002 | Arntzen et al. | 800/288 |
| 6,444,805 B1 | 9/2002 | Sohn et al. | |
| 6,551,820 B1 | 4/2003 | Mason et al. | |
| 6,673,355 B1 | 1/2004 | Estes et al. | |
| 6,846,809 B2 | 1/2005 | Cristiano et al. | |
| 7,002,058 B2 | 2/2006 | Martinell et al. | |
| 7,473,822 B1 | 1/2009 | Paz et al. | |
| 2006/0059589 A1 | 3/2006 | Martinell et al. | |
| 2009/0077694 A1 | 3/2009 | Martinell et al. | |

FOREIGN PATENT DOCUMENTS

WO    WO 97/10347    *    3/1997

OTHER PUBLICATIONS

Woody et al. Staphylococcal enterotoxin B mutants (N23K and F44S): biological effects and vaccine potential in a mouse model. (1997) Vaccine; vol. 15; pp. 133-139.*

Akdis, C. et al., "Epitope-Specific T Cell Tolerance to Phospholipase $A_2$ in Bee Venom Immunotherapy and Recovery by IL-2 and IL-15 In Vitro," J. Clin. Invest., vol. 98, No. 7, pp. 1676-1683, 1996.

Alexander, C. et al., "Peptide-based Vaccines in the Treatment of Specific Allergy," Current Drug Targets-Inflammation and Allergy, vol. 1, pp. 353-361, 2002.

Arakawa, T. et al., "A Plant-Based Cholera Toxin B Subunit-Insulin Fusion Protein Protects Against the Development of Autoimmune Diabetes," Nat. Biotechnol., vol. 16, pp. 934-938, 1998.

Aramaki, Y. et al., "Induction of Oral Tolerance After Feeding of Ragweed Pollen Extract in Mice," Immunology Letters, vol. 40, pp. 21-25, 1994.

Astori, M. et al., "Inducing Tolerance by Intranasal Administration of Long Peptides in Naïve and Primed CBA/J Mice," Journal of Immunology, vol. 165, pp. 3497-3505, 2000.

Avalos, J. et al., "Bialaphos Resistance as a Dominant Selectable Marker in *Neurospora crassa*," Curr. Genet., vol. 16, pp. 369-372, 1989.

Badger, T. et al., "The Health Consequences of Early Soy Consumption," J. Nutr., vol. 132, pp. 559S-565S, 2002.

Barnard, J., "Studies of 400 Hymenoptera Sting Deaths in the United States," J. Allergy Clin. Immunol., vol. 52, No. 5, pp. 259-264, 1973.

Berk, Z., "Technology of Production of Edible Flours and Protein Products from Soybeans," Chapter 3, Oil Mill Operations, web page at http://www.fao.org/docrep/t0532e/t0532e04.htm, as available via the Internet and printed Aug. 16, 2006, 21 pages.

Birnbaum, J. et. al., "Hymenoptera Ultra-Rush Venom Immunotherapy : A Safety Study and Risk Factors," Clin. Exp. Allergy, vol. 33, pp. 58-64, 2003.

Boyles, S., "Feeding Potato Processing Wastes and Culls to Cattle," web page at http://beef.osu.edu/library/potato.html, as available via the Internet and printed Aug. 16, 2006.

Caiyin, Q. et al., "Isolation and Structural Analysis of the Seed-Specific Promoter from Soybean," Agricultural Sciences in China, vol. 4, No. 6, pp. 401-407, 2005.

Carrington, J. et al., "Cap-Independent Enhancement of Translation by a Plant Potyvirus 5' Nontranslated Region," Journal of Virology, vol. 64, No. 4, pp. 1590-1597, 1990.

Cheah, K. et al., Identification and Characterization of the Human Type II Collagen Gene (COL2A1), Proc. Natl. Acad. Sci. USA, vol. 82, No. 9, pp. 2555-2559, 1985.

(Continued)

*Primary Examiner*—Cathy Kingdon Worley
(74) *Attorney, Agent, or Firm*—Kilpatrick Stockton LLP

(57) ABSTRACT

The present invention relates to vaccines that are made in transgenic soybeans for use in humans, animals of agricultural importance, pets, and wildlife. These vaccines are used as vaccines against viral, bacterial, fungal, parasitic or prion related diseases, cancer antigens, toxins, and autologous or self proteins. The transgenic soybeans of the instant invention also can be used for inducing tolerance to allergens or tolerance to autoimmune antigens, wherein an individual shows hypersensitivity to said allergen or has developed autoimmunity to autologous or self proteins, respectively. The invention also relates to prophylatically treating individuals and/or populations prior to showing hypersensitivity to allergens. Other aspects of the invention include using the transgenic soybeans as an oral contraceptive, and the expression of protein adjuvants in transgenic soybeans.

16 Claims, 35 Drawing Sheets

OTHER PUBLICATIONS

Figure 2:
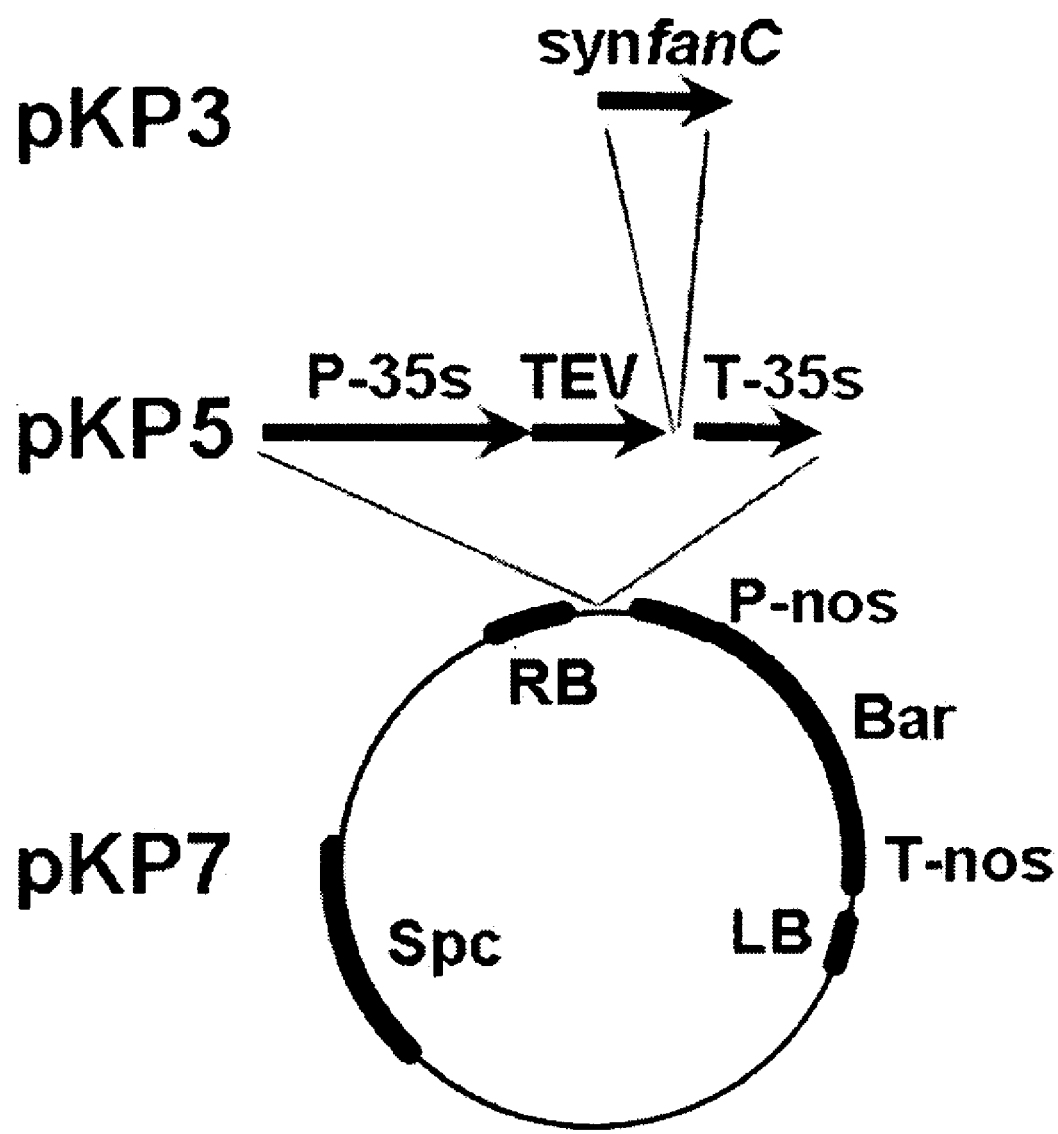

Clemente, T. et al., "Progeny Analysis of Glyphosate Selected Transgenic Soybeans Derived from Agrobacterium-Mediated Transformation," Crop Sci., vol. 40, pp. 797-803, 2000.

Cole, S. et al., "Deciphering the Biology of *Mycobaterium tuberculosis* from the Complete Genome Sequence," Nature, vols. 393 & 396, pp. 190-198, 537-544, 1998.

Collett, M. et al., "Molecular Cloning and Nucleotide Sequences of the Pestivirus Bovine Viral Diarrhea Virus," Virology, vol. 165, No. 1, pp. 191-199, 1988.

Content, J. et al., "The Genes Coding for the Antigen 85 Complexes of *Mycobacterium tuberculosis* and *Mycobacterium bovis* BCG are Members of a Gene Family: Cloning, Sequence Determination, and Genomic Organization of the Gene Coding for Antigen 85-C of *M. tuberculosis*," Infection and Immunity, vol. 59, No. 9, pp. 3205-3212, 1991.

Coussens, L. et al., "Tyrosine Kinase Receptor with Extensive Homology to EGF Receptor Shares Chromosomal Location with Neu Oncogene," Science, vol. 230, No. 4730, pp. 1132-1139, 1985.

De Block, M. et al., "Engineering Herbicide Resistance in Plants by Expression of a Detoxifying Enzyme," EMBO Journal, vol. 6, No. 9, pp. 2513-2518, 1987.

Ditta, G. et al., "Broad Host Range DNA Cloning System for Gram-Negative Bacteria: Construction of a Gene Bank of *Rhizobium meliloti*," Proc. Natl. Acad. Sci. USA, vol. 77, No. 12, pp. 7347-7351, 1980.

Elhofy, A. et al., "Salmonella Infection Does Not Increase Expression and Activity of the High Affinity IL-12 Receptor," J. Immunol., vol. 165, pp. 3324-3332, 2000.

Elliott, K. et al., "Comparative Structure of Human Neuronal Alpha 2-Alpha 7 and Beta 2-Beta 4 Nicotinic Acetylcholine Receptor Subunits and Functional Expression of the Alpha 2, Alpha 3, Alpha 4, Alpha 7, Beta 2, and Beta 4 Subunits," J. Mol. Neurosci., vol. 7, No. 3, pp. 217-228, 1996.

Elsawa, S. et al., "Reduced CTL Response and Increased Viral Burden in Substance P Receptor-Deficient Mice Infected with Murine γ-Herpesvirus 68," J. Immunol., vol. 170, pp. 2605-2612, 2003.

Fang, G. et al., "Recombination following Superinfection by HIV-1," AIDS, vol. 18, No. 2, pp. 153-160, 2004.

Faria, A. et al., "Oral Tolerance Induced by Continuous Feeding: Enhanced Up-Regulation of Transforming Growth Factor-β/Interleukin-10 and Suppression of Experimental Autoimmune Encephalomyelitis," J. Autoimmunity, vol. 20, pp. 135-145, 2003.

Friedman, M. et al., "Nutritional and Health Benefits of Soy Proteins," J. Agric Food Chem., vol. 49, No. 3, pp. 1069-1086, 2001.

Giddings, G., "Transgenic Plants as Protein Factories," Curr. Opin. Biotechnol., vol. 12, pp. 450-454, 2001.

Golden, D. et al., "Discontinuing Venom Immunotherapy: Outcome after Five Years," J. Allergy Clin. Immunol., vol. 97, pp. 579-587, 1996.

Golden, D. et al., "Outcomes of Allergy to Insect Stings in Children, with and without Venom Immunotherapy," New England Journal of Medicine, vol. 351, pp. 668-674, 2004.

Golden, D., "Insect Sting Allergy and Venom Immunotherapy: A Model and a Mystery," Allergy Clin. Immunol., vol. 115, pp. 439-447, 2005.

Goldstein, D. et al., "Biopharmaceuticals Derived from Genetically Modified Plants," Q J Med., vol. 97, pp. 705-716, 2004.

Hajdukiewicz, P. et al., "The Small, Versatile pPZP Family of Agrobacterium Binary Vectors for Plant Transformation," Plant Mol. Biol., vol. 25, pp. 989-994, 1994.

Haq, T. et al., "Oral Immunization with a Recombinant Bacterial Antigen Produced in Transgenic Plants," Science, vol. 268, pp. 714-716, 1995.

Hatic II, S. et al., "In Vitro Assembly of Novel Cholera Toxin-like Complexes," Anal. Biochem., vol. 292, pp. 171-177, 2001.

He, R. et al., "Analysis of Multimerization of the SARS Coronavirus Nucleocapsid Protein," Biochem. Biophys. Res. Commun., vol. 316, No. 2, pp. 476-483, 2004.

Helm, R., "Food Biotechnology: Is This Good or Bad? Implications to Allergic Diseases," Ann. Allergy Asthma, & Immunol., vol. 90, Suppl. 3, pp. 90-98, 2003.

Henahan, S., "Herpes Vaccine from Soy?" Web page at http://www.accessexcellence.org/WN/SU/plantmabs1298.html, as available via the Internet and printed Sep. 28, 2005.

Hinchee, M. et al., "Production of Transgenic Soybean Plants using Agrobacterium-Mediated DNA Transfer," Bio/Technology, vol. 6, pp. 915-922, 1988.

Hoffman, D., "Hymenoptera Venom Proteins," Adv. Exp. Med. Biol., vol. 391, pp. 169-186, 1996.

Hoffman, D., "Fatal Reactions to Hymenoptera Stings," Allergy & Asthma Proc., vol. 24, No. 2, pp. 123-127, 2003.

Holloway, S. et al., "Identification, Sequence Analysis and Characterization of Equine Herpesvirus 5 Glycoprotein B," Arch. Virol., vol. 144, No. 2, pp. 287-307, 1999.

Hood, E. et al., "The Hypervirulence of *Agrobacterium tumefaciens* A281 is Encoded in a Region of pTiBo542 Outside of T-DNA," J. Bacteriol., vol. 168, No. 3, pp. 1291-1301, 1986.

Hunt, K. et al., "A Controlled Trial of Immunotherapy in Insect Hypersensitivity," N. Engl. J. Med., vol. 299, No. 4, pp. 157-161, 1978.

Israeli, R. et al., "Molecular Cloning of a Complementary DNA Encoding a Prostate-Specific Membrane Antigen," Cancer Res. vol. 53, No. 2, pp. 227-230, 1993.

Jilek, S. et al., "Antigen-Independent Suppression of the Allergic Immune Response to Bee Venom Phospholipase $A_2$ by DNA Vaccination in CBA/J Mice," J. Immunol., vol. 166, pp. 3612-3621, 2001.

Kawakami, Y. et al., "Cloning of the Gene Coding for a Shared Human Melanoma Antigen Recognized by Autologous T Cells Infiltrating into Tumor," Proc. Natl. Acad. Sci. USA, vol. 91, No. 9, pp. 3515-3519, 1994.

Kim, J. et al., "Induction of Oral Tolerance to Japanese Cedar Pollen," Arch. Pharm. Res., vol. 24, No. 6, pp. 557-563, 2001.

Kitts, D. et al., "Bioactive Proteins and Peptides from Food Sources. Applications of Bioprocesses used in Isolation and Recovery," Current Pharm. Des., vol. 9, pp. 1309-1323, 2003.

Kretzschmar, H. et al., "Molecular Cloning of a Human Prion Protein cDNA," DNA, vol. 5, No. 4, pp. 315-324, 1986.

Larrick, J. et al., "Producing Proteins in Transgenic Plants and Animals," Curr. Opin. Biotechnol., vol. 12, pp. 411-418, 2001.

Leitermann, K. et al., "Cat Allergen 1: Biochemical, Antigenic, and Allergenic Properties," J. Allergy Clin. Immunol., vol. 74, No. 2, pp. 147-153, 1984.

Lin, T. et al., "STAT3 Activation in Macrophages Following Infection with Salmonella," Biochem. Biophys. Res. Commun., vol. 321, pp. 828-834, 2004.

Liu, K., "Soybeans Chemistry, Technology, and Utilization" Aspen Publishers, Inc., Gaithersburg, Maryland, 1999, ISBN: 0-8342-1299-4.

Lo, R. et al., "Nucleotide Sequence of the Leukotoxin Genes of *Pasteurella haemolytica* Al," Infection and Immunity, vol. 55, No. 9, pp. 1987-1996, 1987.

Lusas, E. et al., "Soy Protein Products: Processing and Use," J. Nutr., vol. 125, pp. 573S-580S, 1995.

Ma, J., "Genes, Greens, and Vaccines," Nat. Biotechnology, vol. 18, pp. 1141, 2000.

Ma, S. et al., "Induction of Oral Tolerance to Prevent Diabetes with Transgenic Plants requires Glutamic Acid Decarboxylase (GAD) and IL-4," Proc. Natl. Acad. Sci. USA., vol. 101, No. 15, pp. 5680-5685, 2004.

Ma, S. et al., "Transgenic Plants Expressing Autoantigens Fed to Mice to Induce Oral Immune Tolerance," Nat. Med., vol. 3, No. 7, pp. 793-796, 1997.

Mason, H. et al., "Expression of Hepatitis B Surface Antigen in Transgenic Plants," Proc. Natl. Acad. Sci. USA, vol. 89, pp. 11745-11749, 1992.

Matsuo, K. et al., "Cloning and Expression of the *Mycobacterium bovis* BCG Gene for Extracellular Alpha Antigen," J. Bacteriology, vol. 170, No. 9, pp. 3847-3854, 1988.

Mayer, L. et al., "Therapeutic Potential of Oral Tolerance," Nat. Rev. Immunol., vol. 4, pp. 407-419, 2004.

McGeoch, D. et al., "DNA Sequence and Genetic Content of the HindIII / Region in the Short Unique Component of the Herpes Simplex Virus Type 2 Genome: Identification of the Gene Encoding Glycoprotein G, and Evolutionary Comparisons," J. Gen. Virol., vol. 68, (Pt. 1), pp. 19-38, 1987.

Messina, M., "Legumes and Soybeans: Overview of Their Nutritional Profiles and Health Effects," Am J. Clin. Nutr., vol. 70 (suppl), pp. 439S-450S, 1999.

Midoro-Horiuti, T. et al., "Identification of Mutations in the Genes for the Pollen Allergens of Eastern Red Cedar (*Juniperes virginiana*)," Clin. Exp. Allergy, vol. 31, No. 5, pp. 771-778, 2001.

Miller, A. et al., "Orally Administered Myelin Basic Protein in Neonates Primes for Immune Responses and Enhances Experimental Autoimmune Encephalomyelitis in Adult Animals," Eur. J. Immunol., vol. 24, pp. 1026-1032, 1994.

Min, K. et al., "Nucleotide Sequence of eCG Alpha-Subunit cDNA and Its Expression in the Equine Placenta," Journal Reprod. Dev., vol. 40, No. 4, pp. 301-305, 1994.

Moreira, L. et al., "Bee Venom Phospholipase Inhibits Malaria Parasite Development in Transgenic Mosquitoes," J. Biol. Chem., vol. 277, No. 43, pp. 40839-40843, 2002.

Motil, K., "Infant Feeding: A Critical Look at Infant Formulas," Curr. Opin. Pediatr., vol. 12, pp. 469-476, 2000.

Muller, U. et al., "Recent Developments and Future Strategies for Immunotherapy of Insect Venom Allergy," Curr. Opin. Allergy Clin. Immunol., vol. 3, pp. 299-303, 2003.

Muller, U. et al., "Successful Immunotherapy with T-Cell Epitope Peptides of Bee Venom Phospholipase A2 Induces Specific T-Cell Anergy in Patients Allergic to Bee Venom," J. Allergy Clin. Immunol., vol. 101, pp. 747-754, 1998.

Muller, U., "Recombinant Hymenoptera Venom Allergens," Allergy, vol. 57, pp. 570-576, 2002.

Nelson, D. et al., "Expression of Hemokinin 1 mRNA by Murine Dendritic Cells," J. Neuroimmunol., vol. 155, pp. 94-102, 2004.

Pall, M., "The Use of Ignite (Basta; glufosinate; phosphinothricin) to Select Transformants of Bar-Containing Plasmids in *Neurospora crassa*," web page at http://www.fgsc.net/fgn/pall1.html, as available via the Internet and printed Aug. 21, 2006.

Papazisi, L. et al., "The Complete Genome Sequence of the Avian Pathogen *Mycoplasma gallisepticum* Strain $R_{low}$," Microbiology, vol. 149 (Part 9), pp. 2307-2316, 2003.

Patriarca, G. et al., "Oral Desensitizing Treatment in Food Allergy: Clinical and Immunological Results," Aliment Pharmacol Ther., vol. 17, pp. 459-465, 2003.

Peacock, J. et al., "Murine Gammaherpesvirus-68-Induced Interleukin-10 Increases Viral Burden, but Limits Virus-Induced Splenomegaly and Leukocytosis," Immunology, vol. 104, pp. 109-117, 2001.

Peterson, R. et al., On Risk and Plant-Based Biopharmaceuticals, Trends Biotechnol., vol. 22, No. 2, pp. 64-66, 2004.

Piller, K. et al., "Expression and Immunogenicity of an *Escherichia coli* K99 Fimbriae Subunit Antigen in Soybean," Planta, vol. 222, pp. 6-18, 2005.

Reisman, R., "Insect Sting Allergy: The Dilemma of the Negative Skin Test Reactor," J. Allergy Clin. Immunol., vol. 107, pp. 781-782, 2001.

Rizzetto, M. et al., "Viral Hepatitis and Liver Disease," Edizioni Minerva Medica Turin 1997, Proceedings of IX Triennial International Symposium on Viral Hepatitis and Liver Disease, Rome, Italy, Hepatitis D, pp. 313-316, 1996.

Rogers, B. et al., "Complete Sequence of the Allergen Amb Alpha II, Recombinant Expression and Reactivity with T Cells from Ragweed Allergic Patients," J. Immunol., vol. 147, No. 8, pp. 2547-2552, 1991.

Ross, R. et al., "Effectiveness of Specific Immunotherapy in the Treatment of Hymenoptera Venom Hypersensitivity: A Meta-Analysis," Clinical Therapeutics, vol. 22, No. 3, pp. 351-358, 2000.

Roth, H. et al., "Evidence for the Expression of Four Myelin Basic Protein Variants in the Developing Human Spinal Cord Through cDNA Cloning," J. Neurosci. Res., vol. 17, No. 4, pp. 321-328, 1987.

Rueff, F. et al., "Patients still Reacting to a Sting Challenge While Receiving Conventional Hymenoptera Venom Immunotherapy are Protected by Increased Venom Doses," J. Allergy Clin. Immunol., vol. 108, pp. 1027-1032, 2001.

Sato, S. et al., "Production of γ-Linolenic Acid and Stearidonic Acid in Seeds of Market-Free Transgenic Soybean," Crop Sci., vol. 44, pp. 646-652, 2004.

Schrewe, H. et al., "Cloning of the Complete Gene for Carcinoembryonic Antigen: Analysis of its Promoter Indicates a Region Conveying Cell Type-Specific Expression," Mol. Cell. Biol., vol. 10, No. 6, pp. 2738-2748, 1990.

Seeger, M. et al., "Antigen-Independent Suppression of the IgE Immune Response to Bee Venom Phospholipase $A_2$ by Maternally Derived Monoclonal IgG Antibodies," Eur. J. Immunol., vol. 28, pp. 2124-2130, 1998.

Seppo, L. et al., "A Follow-Up Study of Nutrient Intake, Nutritional Status, and Growth in Infants with Cow Milk Allergy Fed Either a Soy Formula or an Extensively Hydrolyzed Whey Formula," Am. J. Clin. Nutr., vol. 82, pp. 140-145, 2005.

Slavin, J., "Nutritional Benefits of Soy Protein and Soy Fiber," J. Am. Diet Assoc., vol. 91, No. 7, pp. 816-819, 1991.

Smith, M. et al., "Hepatitis B Surface Antigen (HBsAg) Expression in Plant Cell Culture: Kinetics of Antigen Accumulation in Batch Culture and Its Intercellular Form," Biotechnol. Bioeng., vol. 80, No. 7, pp. 812-822, 2002.

Sojikul, P. et al., "A Plant Signal Peptide-Hepatitis B Surface Antigen Fusion Protein with Enhaced Stability and Immunogenicity Expresses in Plant Cells," Proc. Natl. Acad. Sci. USA, vol. 100, No. 5, pp. 2209-2214, 2003.

Son, Y. et al., "A Novel Bulk-Culture Method for Generating Mature Dendritic Cells from Mouse Bone Marrow Cells," J. Immunol. Methods, vol. 262, pp. 145-157, 2002.

Stepkowski, S. et al., "Induction of Tolerance by Oral Administration of a Tolerogenic Allochimeric Donor/Recipient Class I MHC Protein," Transplantation Proc., vol. 31, p. 1557, 1999.

Strobel, S. et al., "Immune Responses to Fed Protein Antigens in Mice. 3. Systemic Tolerance or Priming is Related to Age at Which Antigen if First Encountered," Pediatric Res., vol. 18, No. 7, pp. 588-594, 1984.

Takahashi, I. et al., "Mechanisms for Mucosal Immunogenicity and Adjuvancy of *Escherichia coli* Labile Enterotoxin," J. Infect. Dis., vol. 173, pp. 627-635, 1996.

Tavares, B. et al., "Development of New IGE Specificities to Hymenoptera Allergens during Venom Specific Immunotherapy," European Annals of Allergy and Clinical Immunology, vol. 37, No. 5, pp. 171-176, 2005.

Telford, E. et al., "The DNA Sequence of Equine Herpesvirus-1," Virology, vol. 189, No. 1, pp. 304-316, 1992.

Valentine, M. et al., "The Value of Immunotherapy with Venom in Children with Allergy to Insect Stings," N. Engl. J. Med., vol. 323, No. 23, pp. 1601-1603, 1990.

Viquez, O. et al., "Structure and Organization of the Genomic Clone of a Major Peanut Allergen Gene, Ara H 1," Mol. Immunol., vol. 40, No. 9, pp. 565-571, 2003.

Von Garnier, C. et al., "Allergen-Derived Long Peptide Immunotherapy Down Regulates Specific IgE Response and Protects from Anaphylaxis," Eur. J. Immunol., vol. 30, pp. 1638-1645, 2000.

Von Garnier, C. et al., "In Vivo Kinetics of the Immunoglobulin E Response to Allergen: Bystander Effect of Coimmunization and Relationship with Anaphylaxis," Clin. Exp. Allergy, vol. 32, pp. 401-410, 2002.

Wang, X et al., "Transgene Vaccination using *Ulex europaeus* Agglutinin 1 (UEA-1) for Targeted Mucosal Immunization against HIV-1 Envelope," Vaccine, vol. 23, pp. 3836-3842, 2005.

Wenzel, J. et al., "Safety of Rush Insect Venom Immunotherapy. The Results of a Retrospective Study in 178 Patients." Allergy, vol. 58, pp. 1176-1179, 2003.

Winningham, K. et al., "Hymenoptera Venom Protease Allergens," J. Allergy Clin. Immunol., vol. 114, pp. 928-933, 2004.

Wu, H. et al., "Oral Tolerance," Immon. Res., vol. 28, No. 3, pp. 265-284, 2003.

Wymann, D. et al., "Enzymatic Activity of Soluble Phospholipase $A_2$ does not Affect the Specific IgE, IgG4 and Cytokine Responses in Bee Sting Allergy," Clin. Exp. Allergy, vol. 28, pp. 839-849, 1998.

Yonezawa, N. et al., "Molecular Cloning of Bovine *Zona pellucida* Glycoproteins ZPA and ZPB and Analysis for Sperm-Binding Component of the Zona," Eur. J. Biochem., vol. 268, No. 12, pp. 3587-3594, 2001.

Zavazava, N. et al., "Oral Feeding of an Immunodominant MHC Donor-Derived Synthetic Class I Peptide Prolongs Graft Survival of Heterotopic Cardiac Allografts in a High-Responder Rat Strain Combination," J. Leukoc. Biol., vol. 67, pp. 793-800, 2000.

Zeitlin, L. et al., "A Humanized Monoclonal Antibody Produced in Transgenic Plants for Immunoprotection of the Vagina against Genital Herpes," Nat. Biotechnol., vol. 16, pp. 1361-1364, 1998.

Zhang, Z. et al., "The Use of Glufosinate as a Selective Agent in Agrobacterium-Mediated Transformation of Soybean," Plant Cell Tissue Organ Cult, vol. 56, pp. 37-46, 1999.

Aziz et al., "Oral vaccines: new needs, new possibilities," BioEssays 29:591-604, 2007.

Chang et al., "*Agrobacterium tumefaciens*-mediated transformation of soybean (*Glycine max* (L.) Merr.) is promoted by the inclusion of potato suspension culture," Bot. Bull. Academia Sinica 32:171-178, 1991.

Cheng et al., "The role of cAMP in mucosal adjuvanticity of *Escherichia coli* heat-labile enterotoxin (LT)," Vaccine 18:38-49, 1999.

Douce et al., "Intranasal Immunogenicity and Adjuvanticity of Site-Directed Mutant Derivatives of Cholera Toxin," Infect. Immun. 65:2821-2828, 1997.

Haynes et al., "Critical issues in mucosal immunity for HIV-1 vaccine development," J. Allergy Clin. Immunol. 122(1):3-9, 2008.

Ko et al., "Two critical factors are required for efficient transformation of multiple soybean cultivars: *Agrobacterium* strain and orientation of immature cotyledonary explant," Theor. Appl. Genet. 107:439-447, 2003.

Lamphear et al., "A corn-based delivery system for animal vaccines: an oral transmissible gastroenteritis virus vaccine boosts lactogenic immunity in swine," Vaccine 22:2420-2424, 2004.

Lauterslager et al., "Oral immunization of naïve and primed animals with transgenic potato tubers expressing LT-B," Vaccine 19:2749-2755, 2001.

Lavelle et al., "Delivery systems and adjuvants for oral vaccines," Expert Opin. Drug Deliv. 3:747-762, 2006.

Mann et al., "Delivery systems: a vaccine strategy for overcoming mucosal tolerance?," Expert Rev. Vaccines 8:103-112, 2009.

Mason et al., "Edible plant vaccines: applications for prophylactic and therapeutic molecular medicine," Trends in Mol. Med. 8(7):324-329, 2002.

A Revolution in Biotechnology, Jean L. Marx Ed., pp. 126-129, 1989.

Mayer et al., "Therapeutic potential of oral tolerance," Nature Rev. Immunol. 4:407-419, 2004.

Meurer et al., "Factors affecting soybean cotyledonary node transformation," Plant Cell Reports 18:180-186, 1998.

Moravec et al., "Production of *Escherichia coli* heat labile toxin (LT) B subunit in soybean seed and analysis of its immunogenicity as an oral vaccine," Vaccine 25:1647-1657, 2007.

Neutra et al., "Mucosal vaccines: the promise and the challenge," Nature Rev. Immunol. 6(2):148-158, 2006.

Noad et al., "Virus-like particles as immunogens," Trends in Microbiology 11(9):438-444, 2003.

Oakes et al., "Stability of a soybean seed-derived vaccine antigen following long-term storage, processing and transport in the absence of a cold chain," J. Sci. Food Agr., pp. 1-30 (in press), 2009.

Paz et al., "Improved cotyledonary node method using an alternative explant derived from mature seed for efficient *Agrobacterium*-mediated soybean transformation," Plant Cell Rep. 25:206-213, 2006.

Paz et al., "Assessment of conditions affecting *Agrobacterium*-mediated soybean transformation using the cotyledonary node explant," Euphytica 136:167-179, 2004.

Paz et al., "*Agrobacterium*-mediated transformation of soybean and recovery of transgenic soybean plants," Iowa State University, Department of Agronomy, pp. 1-6, Jan. 27, 2006.

Piller et al., "Expression and immunogenicity of an *Escherichia coli* K99 fimbriae subunit antigen in soybean," Planta 222:6-18, 2005.

Rosales-Mendoza et al., "Expression of an *Escherichia coli* antigenic fusion protein comprising the heat labile toxin B subunit and the heat stable toxin, and its assembly as a functional oligomer in transplastomic tobacco plants," The Plant Journal 57:45-54, 2009.

Ryan et al., "Immunomodulators and delivery systems for vaccination by mucosal routes," Trends in Biotechnology 19(8):293-304, 2001.

Shewen et al., "Challenges in mucosal vaccination of cattle," Vet. Immunol. Immunopath. 128:192-198, 2009.

Silin et al., "Oral vaccination: where we are?," Expert Opin. Drug Deliv. 4(4):323-340, 2007.

Simmons et al., "MHC Class I-Restricted Cytotoxic Lymphocyte Responses Induced by Enterotoxin-Based Mucosal Adjuvants," J. Immunol. 163:6502-6510, 1999.

Stiles et al., "Mucosal Vaccination with Recombinantly Attenuated Staphylococcal Enterotoxin B and Protection in a Murine Model," Infection and Immunity 69:2031-2036, 2001.

Verweij et al., "Musosal immunoadjuvant activity of recombinant *Esherichia coli* heat-labile enterotoxin and its B subunit: Induction of systemic IgG and secretory IgA responses in mice by intranasal immunization with influenza virus surface antigen," Vaccine 16(20):2069-2076, 1998.

Zeng et al., "Refined glufosinate selection in *Agrobacterium*-mediated transformation of soybean [*Glycine max* (L.) Merrill]," Plant Cell Rep. 22:478-482, 2004.

* cited by examiner

```
fanC:     atgaaaaaaacactgctagctattatcttaggtggtatggcttttgcgactaccaatgct 60 fanC:     tctgcgaatacaggtactattaacttcaatggcaaaataacgagtgctacttgtacaatt 120
             ||||||||  |||||  |||||  ||  ||  ||  ||  ||    ||  ||  || |||||
synfanC:     atgaatacaggcactatcaactttaacggaaagattacttccgcgacgtgcacaatc 57 fanC:     gaccctgaggtcaatggtaatcgtacatcaactatagatcttgggcaggctgctattagt 180
          ||||| |||||  || ||  ||||| |||||  ||  ||  ||||| ||  || || |||
synfanC:  gaccccgaggtgaacggaaatcgcacatccactatcgacctgggccaggccgcgatcagt 117 fanC:     ggtcatggcactgtagtggattttaaactaaaaccagcgcccggcagtaatgactgccta 240
          ||  ||  ||||||  ||  ||  |||||| ||  || ||||| || |||   |||||| |
synfanC:  ggacacggcacggttgtagactttaagctcaagccagcccctggctctaacgactgcttg 177 fanC:     gcgaaaacaaatgctcgtattgactggtctggttctatgaacagtttaggttttaataat 300
          ||  ||  ||||| ||||| ||||||||||||||||||  ||  ||  ||||||    | || ||  |||||
synfanC:  gccaagacaaacgctcggattgactggtcgggctcgatgaactcgcttggattcaataac 237 fanC:     acagcttcaggaaatactgctgctaaaggataccatatgactttgcgcgcaacaaacgtt 360
          ||  |||   ||  |||||| ||||| ||||| ||||  ||  |||||    | ||  || || ||||||
synfanC:  actgctagcggcaataccgctgccaaagggtatcacatgaccctacgtgcgactaacgtg 297 fanC:     ggaaatgggtctggtggtgctaatattaatacttcattcactacggctgaatacactcac 420
          ||||| ||    |||||||||||| ||  ||  |||||||||||| ||||| |||||||| |||
synfanC:  ggaaacggtagtggtggtgcgaacatcaacacttcattcaccacggcggaatacacccac 357 fanC:     acttctgcaattcagtcatttaactattcagcccagctgaaaaaagatgaccgcgctccg 480
          ||||| ||  || ||||| ||  |||||||||| |||||  ||  |||||  |  || ||
synfanC:  acttcggctatacagtccttcaactattccgcccaacttaagaaagacgatagggcacct 417 fanC:     tctaatggtggatataaagctggcgtatttactacttcagcatccttcttagtcacttat 540
          ||||| ||  ||  |||||| ||  ||  ||  ||  ||     || ||  |||  | || |||
synfanC:  tctaacggagggtataaggcgggagtcttcacgaccagcgcgtcattcctcgtgacctat 477 fanC:     atgtaa 546
          |||||
synfanC:  atgtag 483

SEQ ID NO: 36 fanC
SEQ ID NO: 37 synfanC
```

Fig. 1

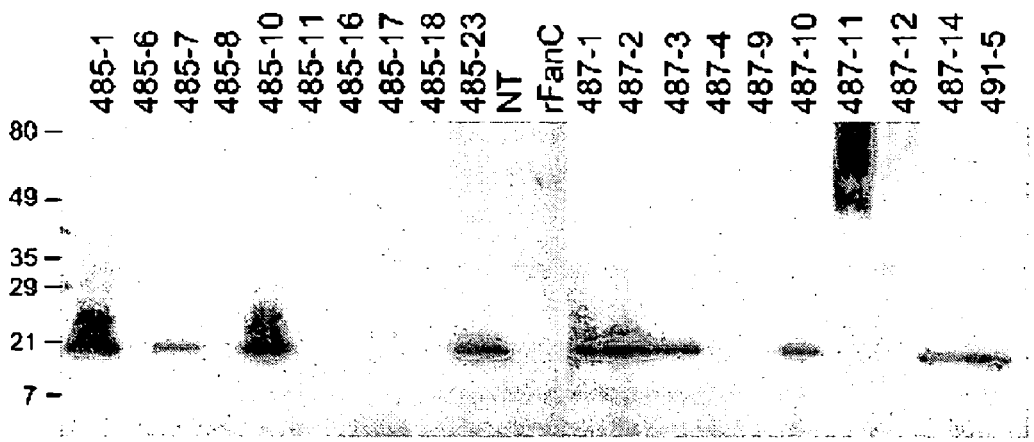
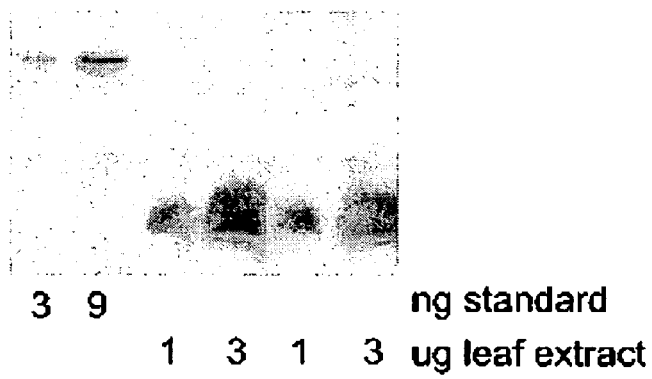
Fig. 4

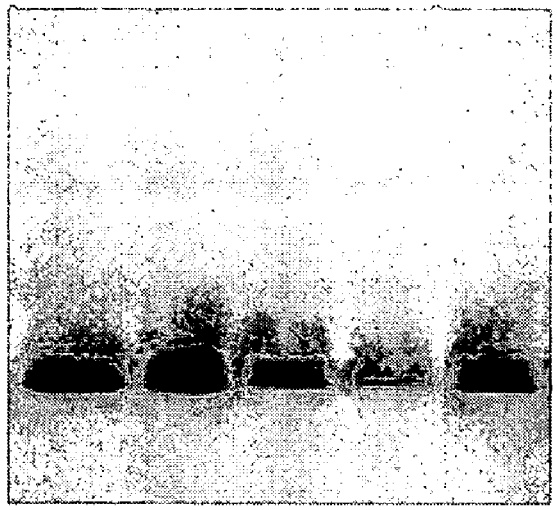 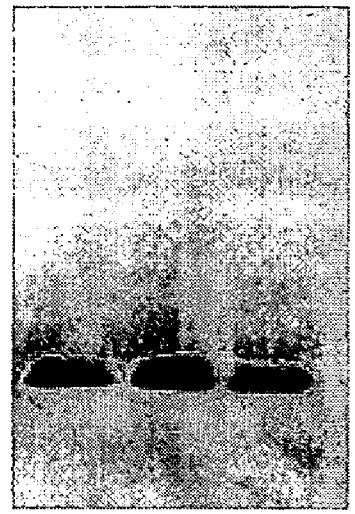
Fig. 5

485-1 Wild type
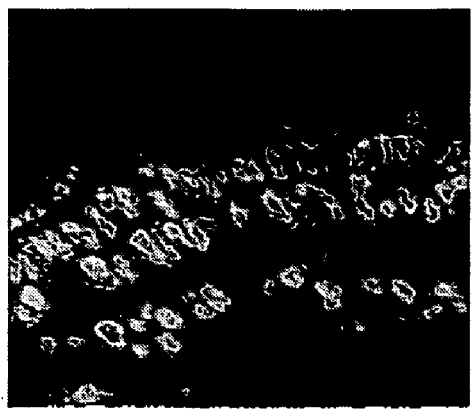
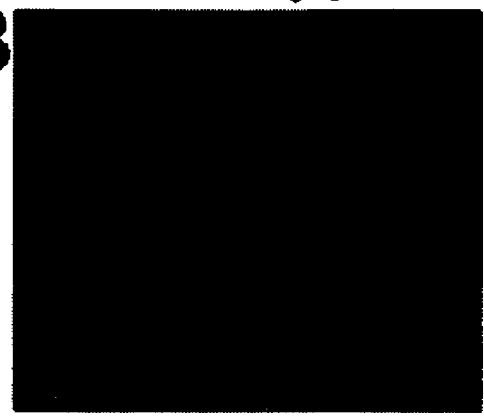
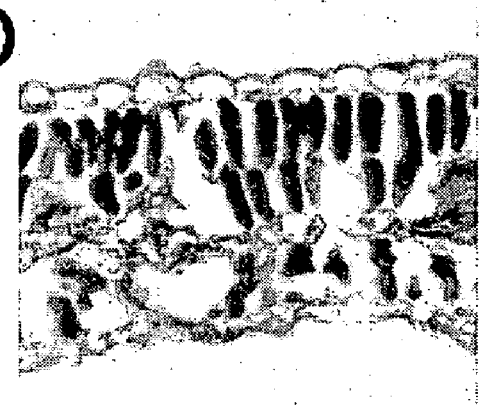
Fig. 7

```
  1 atgtataaga gattatttat ttcacatgta attttgatat tcgcactgat attagttatt
 61 tctacaccca acgttttagc agagagtcaa ccagatccta aaccagatga gttgcacaaa
121 tcgagtaaat tcactggtTT Gatggaaaat atgaaagttt tgtatgatga taatcatgta
181 tcagcaataa acgttaaatc tatagatcaa tttctatact ttgacttaat atattctatt
241 aaggacacta agttagggaa tTATgataat gttcgagtcg aatttaaaaa caaagattta
301 gctgataaat acaaagataa atacgtagat gtgtttggag ctaattatta ttatcaatgt
361 tattttcta aaaaaacgaa tgatattaat tcgcatcaaa ctgacaaacg aaaaacttgt
421 atgtatggtg gtgtaactga gcataatgga aaccaattag ataaatatag aagtattact
481 gttcgggtat ttgaagatgg taaaaattta ttatcttttg acgtacaaac taataagaaa
541 aaggtgactg ctcaagaatt agattaccta actcgtcact atttggtgaa aaataaaaaa
601 ctctatgaat ttaacaactc gccttatgaa acgggatata ttaaatttat agaaaatgag
661 aatagctttt ggtatgacat gatgcctgca ccaggagata aatttgacca atctaaatat
721 ttaatgatgt acaatgacaa taaaatggtt gattctaaag atgtgaagat tgaagtttat
781 cttacgacaa agaaaaagtg a
```

SEQ ID NO: 38

FanC-1:
TCATGAATACAGGCACTATCAACTTTAACGGAAAGATTACTTCCGCGACGTG
CACAATCGACCCCGAGGTGAACGGAAATCG SEQ ID NO: 1

FanC-2:
CACGGCACGGTTGTAGACTTTAAGCTCAAGCCAGCCCCTGGCTCTAACGACT
GCTTGGCCAAGACAAACGCTCGGATTGACTGGTCGGGCTCGATGAACT SEQ
ID NO: 2

FanC-3:
CAATAACACTGCTAGCGGCAATACCGCTGCCAAAGGGTATCACATGACCCTA
CGTGCGACTAACGTGGGA SEQ ID NO: 3

FanC-4:
TCATTCACCACGGCGGAATACACCCACACTTCGGCTATACAGTCCTTCAACTA
TTCCGCCCAACTTAAGAAAGACGATAGGGCACCTTCTAACGGAGGGT SEQ ID
NO: 4

FanC-5:
TCTAGAGCTCGTCCTWCATATAGGTCACGAGGAATGACGCGCTGGTCGTGAA
GACTCCCGCCTTATACCCTCCGTTAGAAGGTGCCCTATCGTCTT
SEQ ID NO: 5

FanC-6:
AGTGTGGGTGTATTCCGCCGTGGTGAATGAAGTGTTGATGTTCGCACCACCAC
TACCGTTTCCCACGTTAGTCGCACGTAGGGTCATGTG SEQ ID NO: 6

FanC-7:
GCAGCGGTATTGCCGCTAGCAGTGTTATTGAATCCAAGCGAGTTCATCGAGC
CCGACCAGTCAATCCGA SEQ ID NO: 7

FanC-8:
CTTGAGCTTAAAGTCTACAACCGTGCCGTGTCCACTGATCGCGGCCTGGCCCA
GGTCGATAGTGGATGTGCGATTTCCGTTCACCTCGGGGTCGATTGTG SEQ ID
NO: 8

Fig. 25A

FanC-9: GCCCTTTCATGAAT ACAGGCAC          SEQ ID NO: 9
FanC-10: GCTCTAGAGCTCGTCCTTCATATAGG      SEQ ID NO: 10
FanC-11: CGGAAAGATTACTTCCGCGACG          SEQ ID NO: 11
FanC12: TAGGGCACCTTCTAACGGAGGG           SEQ ID NO: 12
FanC-13: TAGGTCACGAGGAATGACGCGC          SEQ ID NO: 13
FanC-14: TCGATTGTGCACGTCGCGGAAG          SEQ ID NO: 14
FanC-15:
ACATATGCATCATCATCATCATCATGGTATGAATACAGGCACTATCAAC
SEQ ID NO: 15
FanC-16: GATCTAGACTACATATAGGTCACGAGGAATGACG SEQ ID NO: 16
VSP-1: GCTTCCACACATGGGAGCAG             SEQ ID NO: 17
VSP-2: CCTCTGTGGTCTCCAAGCAG             SEQ ID NO: 18
VSP-3: CGGCATAGATAACACCGTACTC           SEQ ID NO: 19
VSP-4: AGTCTCTGGCAATGCCGGTG             SEQ ID NO: 20
LT-A-F1: TGGTATCGTGTGAACTTCGGTG          SEQ ID NO: 21
LT-A-R1: CGAAGTATTCGTTGTGTCCTCTG         SEQ ID NO: 22
LT-A-R2: GTACCTGTCGCGGTATTCACGG          SEQ ID NO: 23
LT-B-F1: CTGTCATACACTGAGAGCATGG          SEQ ID NO: 24
LT-B-R1: TTGGGTGTTCCTATACTCGGAG          SEQ ID NO: 25
LT-B-R2: GTTCTTCATGCTAATTGCAGCG          SEQ ID NO: 26
T35S-R1: ACTAAGGGTTTCTTATATGCTC          SEQ ID NO: 27
TEV-R1: TGCTGCAATAGAAGTAGAATGC           SEQ ID NO: 28
P35S-R1: AGCTGGGCAATGGAATCCGAGG          SEQ ID NO: 29
P35S-R2: GCCCTTTGGTCTTCTGAGACTG          SEQ ID NO: 30
PNos-R1: ACGTTGCGGTTCTGTCAGTTCC          SEQ ID NO: 31
PNos-R2: AAACGATCCAGATCCGGTGCAG          SEQ ID NO: 32
SEB-F1: GGACAAGCGCCTCTTCATCTC           SEQ ID NO: 33
SEB-R1: AGGTACACCTCGATCTTCACG           SEQ ID NO: 34
SEB-R2: TCCGTTGTGCTCAGTCACGC            SEQ ID NO: 35

Fig. 25B

The sequence for K99 fanC
```
1    tagggaatgg ctatgttttc tggtgattcc acggaactaa aaaataatat cgaacaatgg
61   agaatctaga tgaaaaaaac actgctagct attatcttag gtggtatggc ttttgcgact
121  accaatgctt ctgcgaatac aggtactatt aacttcaatg gcaaaataac gagtgctact
181  tgtacaattg accctgaggt caatggtaat cgtacatcaa ctatagatct tgggcaggct
241  gctattagtg gtcatggcac tgtagtggat tttaaactaa aaccagcgcc cggcagtaat
301  gactgcctag cgaaaacaaa tgctcgtatt gactggtctg gttctatgaa cagtttaggt
361  tttaataata cagcttcagg aaatactgct gctaaaggat accatatgac tttgcgcgca
421  acaaacgttg gaaatgggtc tggtggtgct aatattaata cttcattcac tacggctgaa
481  tacactcaca cttctgcaat tcagtcattt aactattcag cccagctgaa aaaagatgac
541  cgcgctccgt ctaatggtgg atataaagct ggcgtattta ctacttcagc atccttctta
601  gtcacttata tgtaatattt aaagtatttt acattgcggg catatctatg attgcccgca
661  atattactga tggatattat atgaatagaa aaaaacatca gattttaaaa attttattgt
721  tgtgtctaat aagcagtaaa
```

SEQ ID NO: 36

Synthetic fanC DNA sequence optimized for expression in soybean. The translational start (ATG) and stop (TAA) signals are shown in bold.

TCATGAATACAGGCACTATCAACTTTAACGGAAAGATTACTTCCGCGACGTGCACAATCGACCCCGAGGTG
AACGGAAATCGCACATCCACTATCGACCTGGGCCAGGCCGCGATCAGTGGACACGGCACGGTTGTAGACTT
TAAGCTCAAGCCAGCCCCTGGCTCTAACGACTGCTTGGCCAAGACAAACGCTCGGATTGACTGGTCGGGCT
CGATGAACTCGCTTGGATTCAATAACACTGCTAGCGGCAATACCGCTGCCAAAGGGTATCACATGACCCTA
CGTGCGACTAACGTGGGAAACGGTAGTGGTGGTGCGAACATCAACACTTCATTCACCACGGCGGAATACAC
CCACACTTCGGCTATACAGTCCTTCAACTATTCCGCCCAACTTAAGAAAGACGATAGGGCACCTTCTAACG
GAGGGTATAAGGCGGGAGTCTTCACGACCAGCGCGTCATTCCTCGTGACCTATATGTAGGACGAGCTCTAG

SEQ ID NO: 37

Translated synthetic FanC amino acid sequence
MNTGTINFNGKITSATCTIDPEVNGNRTSTIDLGQAAISGHGTVVDFKLKPAPGSNDCLAKTNARIDWSGS
MNSLGFNNTASGNTAAKGYHMTLRATNVGNGSGGANINTSFTTAEYTHTSAIQSFNYSAQLKKDDRAPSNG
GYKAGVFTTSASFLVTYM

SEQ ID NO: 38

Fig. 25C

Synthetic fanC DNA sequence targeted for expression in soybean
chloroplasts. The translational start (ATG) and stop (TAG) signals are
shown in bold. The underlined sequence encodes a chloroplast targeting
peptide to direct protein accumulation to the chloroplast. The
chloroplast targeting peptide should be cleaved from this protein to
yield a mature transgenic FanC protein whose sequence is analogous to
that above.

ATG<u>GCTTCTATGATATCCTCTTCCGCTGTGACAACAGTCAGCCGTGCCTCTAGGGGGCAATCCGCCGCAAT</u>
<u>GGCTCCATTCGGCGGCCTCAAATCCATGACTGGA</u>TTCCCAGTGAGGAAGGTCAACACTGACATTACTTCCA
TTACAAGCAATGGTGGAAGAGTAAAGTGCATGCAGGTGTGGCCTCCAATTGGAAAGAAGAAGTTTGAGACT
CTTTCCTATTTGCCACCATTGACGAGAGATTCCCGGGCCATGAATACAGGCACTATCAACTTTAACGGAAA
GATTACTTCCGCGACGTGCACAATCGACCCCGAGGTGAACGGAAATCGCACATCCACTATCGACCTGGGCC
AGGCCGCGATCAGTGGACACGGCACGGTTGTAGACTTTAAGCTCAAGCCAGCCCCTGGCTCTAACGACTGC
TTGGCCAAGACAAACGCTCGGATTGACTGGTCGGGCTCGATGAACTCGCTTGGATTCAATAACACTGCTAG
CGGCAATACCGCTGCCAAAGGGTATCACATGACCCTACGTGCGACTAACGTGGGAAACGGTAGTGGTGGTG
CGAACATCAACACTTCATTCACCACGGCGGAATACACCCACACTTCGGCTATACAGTCCTTCAACTATTCC
GCCCAACTTAAGAAAGACGATAGGGCACCTTCTAACGGAGGGTATAAGGCGGGAGTCTTCACGACCAGCGC
GTCATTCCTCGTGACCTATATGTAG

SEQ ID NO: 39

Synthetic SEB DNA sequence optimized for expression in soybean. The
translational start (ATG) and stop (TAA) signals are shown in bold.
The locations of the arginine and alanine codons, which render SEB
nontoxic, are underlined.

CCATGGACAAGCGCCTCTTCATCTCACACGTGATCCTCATCTTCGCTCTTATCCTCGTGATCTCAACTCCA
AACGTGCTTGCTGAGTCACAGCCAGACCCCAAGCCAGACGAGTTGCACAAGTCATCTAAGTTCACTGGC<u>AG</u>
<u>G</u>ATGGAGAACATGAAGGTGCTTTACGACGACAACCACGTGTCTGCTATCAACGTGAAGTCAATCGACCAGT
TCCTTTACTTCGACCTCATCTACTCTATCAAGGACACAAAGCTCGGCAAC<u>GCC</u>GACAACGTGAGGGTGGAG
TTCAAGAACAAGGACCTTGCTGACAAGTACAAGGACAAGTACGTGGACGTGTTCGGCGCCAACTACTACTA
CCAGTGCTACTTCTCTAAGAAGACCAACGACATCAACTCTCACCAGACAGACAAGAGGAAGACATGCATGT
ACGGCGGCGTGACTGAGCACAACGGAAACCAGCTTGACAAGTACAGGTCTATCACCGTGAGGGTGTTCGAG
GACGGAAAGAACCTTCTTTCTTTCGACGTGCAGACAAACAAGAAGAAGGTGACCGCCCAGGAGCTGGACTA
CCTTACCAGGCACTACCTTGTGAAGAACAAGAAGCTCTACGAGTTCAACAACTCACCATACGAGACCGGAT
ACATCAAGTTCATCGAGAACGAGAACTCTTTCTGGTACGACATGATGCCCGCCCCTGGTGACAAGTTCGAC
CAGTCTAAGTACCTTATGATGTACAACGACAACAAGATGGTGGACTCTAAGGACGTGAAGATCGAGGTGTA
CCTTACTACTAAGAAGAAGTAATCTAGA

SEQ ID NO: 40

The sequence for Staphylococcus aureus SEB. The arginine and alanine
codons which render SEB nontoxic are underlined (WILD TYPE HAS
TYROSINES AT THESE POSITIONS).
1    MDKRLFISHV ILIFALILVI STPNVLAESQ PDPKPDELHK SSKFTGRMEN MKVLYDDNHV
61   SAINVKSIDQ FLYFDLIYSI KDTKLGN<u>A</u>DN VRVEFKNKDL ADKYK<u>D</u>KYVD VFGANYYYQC
121  YFSKKTNDIN SHQTDKRKTC MYGGVTEHNG NQLDKYRSIT VRVFEDGKNL LSFDVQTNKK
181  KVTAQELDYL TRHYLVKNKK LYEFNNSPYE TGYIKFIENE NSFWYDMMPA PGDKFDQSKY
241  LMMYNDNKMV DSKDVKIEVY LTTKKK

SEQ ID NO: 41

Fig. 25D

Native DNA sequence for E. coli labile toxin: ORIGIN
```
   1 ggatccgtca tgttgcatat aggttaaaca aaacaagtgg cgttatcttt ttccggattg
  61 tcttcttgta tgatatataa gttttcctcg atgaaaaata taactttcat ttttttatt
 121 ttattagcat cgccattata tgcaaatggc gacaaattat accgtgctga ctctagaccc
 181 ccagatgaaa taaaacgttc cggaggtctt atgcccagag ggcataatga gtacttcgat
 241 agaggaactc aaatgaatat taatctttat gatcacgcga gaggaacaca aaccggcttt
 301 gtcagatatg atgacggata tgtttccact tctcttagtt tgagaagtgc tcacttagca
 361 ggacagtcta tattatcagg atattccact tactatatat atgttatagc gacagcacca
 421 aatatgttta atgttaatga tgtattaggc gtatacagcc ctcacccata tgaacaggag
 481 gtttctgcgt taggtggaat accatattct cagatatatg gatggtatcg tgttaatttt
 541 ggtgtaattg atgaacgatt acatcgtaac agggaatata gagaccggta ttacagaaat
 601 ctgaatatag ctccggcaga ggatggttac agattagcag gtttcccacc ggatcaccaa
 661 gcttggagag aagaccctg gattcatcat gcaccacaag gttgtggaaa ttcatcaaga
 721 acaattacag atggatacttg taatgaggag acccagaatc tgagcacaat atatctcagg
 781 aaatatcaat caaaagttaa gaggcagata ttttcagact atcagtcaga ggttgacata
 841 tataacagaa ttcgggatga attatgaata aagtaaaatg ttatgtttta tttacggcgt
 901 tactatcctc tctatgtgca tacggagctc cccagtctat tacagaacta tgttcggaat
 961 atcgcaacac acaaatatat acgataaatg acaagatact atcatatacg gaatcgatgg
1021 caggtaaaag agaaatggtt atcattacat ttaagagcgg cgcaacattt caggtcgaag
1081 tcccgggcag tcaacatata gactcccaaa aaaagccat gaaaggatg aaggacacat
1141 taagaatcac atatctgacc gagaccaaaa ttgataaatt atgtgtatgg aataataaaa
1201 cccccaattc aattgcggca atcagtatgg aaaactagtt tgctttaaaa gcatgtctaa
1261 tgctaggaac ctatataaca actactgtac ttatactaat gagccttatg ctgcatttga
1321 aaaggcggta gaggatgcaa taccgatcct taactgtaa cactataaca gcttccacta
1381 cagggagctg ttatagcaca cagaaaaaac taagctaggc tgggggggcaa gctt
```

SEQ ID NO: 42

Synthetic LT-A sequence optimized for expression in soybeans. The translational start (ATG) and stop (TAG) signals are shown in bold.
ATGGGTGATAGACTCTATCGTGCTGACTCTAGGCCACCTGATGAGATCAAGCGCTCAGGGGGCTTGATGCC
CAGAGGACACAACGAATACTTCGATAGGGGTACTCAAATGAACATCAATCTCTATGACCACGCAAGAGGAA
CCCAGACAGGTTTTGTTAGATATGATGACGGCTACGTGTCCACTAGTCTGTCTCTTAGGAGCGCTCATCTA
GCCGGGCAATCCATCTTGAGTGGATACTCAACCTACTACATCTACGTCATTGCAACAGCCCCAAACATGTT
CAACGTGAATGATGTGTTAGGCGTGTACTCTCCACACCCTTATGAGCAGGAAGTTAGCGCTCTCGGAGGTA
TTCCTTACTCACAAATCTACGGGTGGTATCGTGTGAACTTCGGTGTCATTGATGAGAGGCTTCATAGAAAC
CGTGAATACCGCGACAGGTACTACCGTAACTTGAACATAGCTCCCGCAGAGGATGGATACCGCCTGGCCGG
TTTCCCACCTGATCACCAGGCTTGGAGAGAGGAACCTTGGATTCATCATGCACCACAAGGCTGCGGAAACT
CTTCCGGTACTATCACCGGGGACACATGTAACGAGGAAACTCAGAATCTTAGTACCATCTACTTGAGGGAA
TACCAAAGCAAGGTGAAAAGACAGATATTCTCTGATTACCAATCAGAGGTTGACATCTACAACAGGATTAG
GGATGAACTCTAG

SEQ ID NO: 43

Translated synthetic LT-A protein sequence. The arginine to glycine change at position 192 (underlined) renders LT-A nontoxic.
MGDRLYRADSRPPDEIKRSGGLMPRGHNEYFDRGTQMNINLYDHARGTQTGFVRYDDGYV
STSLSLRSAHLAGQSILSGYSTYYIYVIATAPNMFNVNDVLGVYSPHPYEQEVSALGGIP
YSQIYGWYRVNFGVIDERLHRNREYRDRYYRNLNIAPAEDGYRLAGFPPDHQAWREEPWI
HHAPQGCGNSS<u>G</u>TITGDTCNEETQNLSTIYLREYQSKVKRQIFSDYQSEVDIYNRIRDEL

Fig. 25E

SEQ ID NO: 45

Synthetic LT-B sequence optimized for expression in soybeans. The translational start (ATG) and stop (TAG) signals are shown in bold.

CCATGGCCCCTCAGACCATTACAGAGCTTTGCTCCGAGTATAGGAACACCCAAATCTACACCATAAACGAC
AAGATCCTGTCATACACTGAGAGCATGGCCGGGAAGAGGGAGATGGTCATAATCACCTTTAAGTCCGGCGA
AACCTTCCAGGTCGAAGTGCCCGGTAGCCAGCATATCGACTCCCAAAAGAAGGCCATTGAGAGGATGAAGG
ACACCTTGCGCATTACTTACCTTACTGAGACTAAGATCGACAAACTCTGCGTGTGGAACAACAAGACTCCA
AACTCTATCGCTGCAATTAGCATGAAGAACTAGTCTAGA

SEQ ID NO: 46

Translated synthetic LT-B protein sequence.

MAPQTITELCSEYRNTQIYTINDKILSYTESMAGKREMVIITFKSGETFQVEVPGSQHI
DSQKKAIERMKDTLRITYLTETKIDKLCVWNNKTPNSIAAISMKN

SEQ ID NO: 48

The native sequence for honey bee (Apis mellifera) phospholipase A2:

```
1   gtgctctcgc gtactctgtg aaaatcaccg gaaggaaccg cttttcgcct cgctcctcga
61  ccattttcca ttcaaagagg ctctccttcc tcttcttgta acctccgctt cccttcttct
121 cctcttctcc cacgatgcaa gtcgttctcg gatccttgtt ccttctcctc ctctctacct
181 ctcacggatg gcaaatcagg gataggatcg gggataacga gttggaggaa cggataatat
241 atccaggaac gttatggtgc gggcatggta acaagtcgtc cggcccgaac gagctaggtc
301 ggttcaagca cacggatgca tgctgtcgaa cccacgacat gtgcccggac gtgatgtcag
361 ctggtgaatc gaagcacggc ctgaccaaca cggcctccca caccaggttg tcgtgcgact
421 gcgacgacaa gttctatgat tgtcttaaaa attcggcgga cacgattagc tcgtatttcg
481 tagggaagat gtacttcaat ctgatagaca cgaagtgtta caaactggag catcctgtca
541 ccgggtgcgg tgagagaacc gagggtcgtt gtcttcacta caccgtggac aaaagcaaac
601 cgaaagtgta ccaatggttc gatcttcgca agtattgata aattcacggg gcggatcttg
661 agagtaccac ttcgagatcg tttattta
```

SEQ ID NO: 49

Synthetic phospholipase A2 DNA sequence optimized for expression in soybean. The translational start (ATG) and stop (TAA) signals are shown in bold. The location of the amino acid change used to inactivate phospholipase A2 activity is underlined.

TCATGATCATCTATCCTGGAACCTTGTGGTGCGGACATGGTAACAAGTCATCAGGTCCAAATGAGTTGGGG
AGGTTCAAGCACACAGACGCCTGTTGCAGGACACAGGATATGTGTCCAGATGTGATGAGCGCTGGCGAATC
AAAGCACGGTTTGACAAACACCGCTTCTCATACTCGTCTCTCTTGTGATTGTGATGACAAGTTTTACGATT
GTCTGAAGAACTCCGCTGACACTATTTCTTCCTATTTCGTGGGTAAGATGTACTTCAACTTGATAGATACC
AAGTGCTACAAGCTGGAACACCCTGTGACTGGCTGCGGAGAAAGGACCGAAGGTAGGTGCCTTCACTACAC
CGTGGACAAATCAAAGCCCAAAGTTTATCAGTGGTTCGATCTGCGCAAATACTAATCTAGA

SEQ ID NO: 50

Fig. 25F

Translated synthetic phospholipase A2 protein sequence. The histidine to glutamic acid (Q) change rendering phospholipase A2 inactive is underlined.

MIIYPGTLWCGHGNKSSGPNELGRFKHTDACCRTQDMCPDVMSAGESKHGLTNTASHTRLSCDCDDKFYDC
LKNSADTISSYFVGKMYFNLIDTKCYKLEHPVTGCGERTEGRCLHYTVDKSKPKVYQWFDLRKY

SEQ ID NO: 51

Sequence comparison of E. coli wildtype LT-A to the synthetic LT-A designed for soybean.

```
E. coli      1  atgaaaaatataactttcatttttttatttattagcatcgccattata      50
                                                               |
synLT-A      1                                                 A      1

E. coli     51  tgcaaatggcgacagattataccgtgctgactctagacccccagatgaaa    100
                  ||    ||.||.|||.|.||.|||||||||||||||.||.||.||||| .|
synLT-A      2  TG-----GGTGATAGACTCTATCGTGCTGACTCTAGGCCACCTGATGAGA     46

E. coli    101  taaaacgttccggaggtcttatgcccagagggcataatgagtacttcgat   150
                |.||.||.||.||.||...|.|||||||||||.||.||.||.||||||||
synLT-A     47  TCAAGCGCTCAGGGGGCTTGATGCCCAGAGGACACAACGAATACTTCGAT     96

E. coli    151  agaggaactcaaatgaatattaatctttatgatcacgcgagaggaacaca   200
                ||.||.||||||||||||.||.|||||.|||||.|||||.||||||||.||
synLT-A     97  AGGGGTACTCAAATGAACATCAATCTCTATGACCACGCAAGAGGAACCCA    146

E. coli    201  aaccggctttgtcagatatgatgacggatatgtttccacttctcttagtt   250
                .||.||.|||||.||||||||||||||||||.||.||.|||||...|||...|.
synLT-A    147  GACAGGTTTTGTTAGATATGATGACGGCTACGTGTCCACTAGTCTGTCTC    196

E. coli    251  tgagaagtgctcacttagcaggacagtctatattatcaggatattccact   300
                |.||.||.|||||...||||.||.||.||.||.||.||....|||||.||.||.
synLT-A    197  TTAGGAGCGCTCATCTAGCCGGGCAATCCATCTTGAGTGGATACTCAACC    246

E. coli    301  tactatatatatgttatagcgacagcaccaaatatgtttaatgttaatga   350
                |||||.||.||.||.||.||.|||||.|||||.|||||.||.||.|||||
synLT-A    247  TACTACATCTACGTCATTGCAACAGCCCCAAACATGTTCAACGTGAATGA    296

E. coli    351  tgtattaggcgtatacagccctcacccatatgaacaggaggtttctgcgt   400
                |||.||||||||.|||...||.|||||.|||||.|||||.|||...||..
synLT-A    297  TGTGTTAGGCGTGTACTCTCCACACCCCTTATGAGCAGGAAGTTAGCGCTC    346

E. coli    401  taggtggaataccatattctcagatatatggatggtatcgtgttaatttt   450
                |.||.||.||.||.||.||.||.|||||.||.|||||||||||||.||.||.
synLT-A    347  TCGGAGGTATTCCTTACTCACAAATCTACGGGTGGTATCGTGTGAACTTC    396

E. coli    451  ggtgtgattgatgaacgattacatcgtaacagggaatatagagaccggta   500
                |||||.||||||||..|...|.|||.|.|||.|.||||||...|.|||.||||
synLT-A    397  GGTGTCATTGATGAGAGGCTTCATAGAAACCGTGAATACCGCGACAGGTA    446
```

Fig. 25G

```
E. coli    501 ttacagaaatctgaatatagctccggcagaggatggttacagattagcag   550
               .|||.|.||..||||.||||||||.|||||||||||.|||.|..|.||.|
synLT-A    447 CTACCGTAACTTGAACATAGCTCCCGCAGAGGATGGATACCGCCTGGCCG   496

E. coli    551 gtttcccaccggatcaccaagcttggagagaagaaccctggattcatcat   600
               ||||||||||.||||||||.|||||||||||.|||||.||||||||||||
synLT-A    497 GTTTCCCACCTGATCACCAGGCTTGGAGAGAGGAACCTTGGATTCATCAT   546

E. coli    601 gcaccacaaggttgtggaaattcatcaagaacaatcacaggtgatacttg   650
               |||||||||||.||.|||||.||.||..|.||.|||||.||.||.||.||
synLT-A    547 GCACCACAAGGCTGCGGAAACTCTTCCGGTACTATCACCGGGGACACATG   596

E. coli    651 taatgaggagacccagaatctgagcacaatatatctcagggaatatcaat   700
               |||.|||||.||.||||||||.||.||.||.||..|.||||||||.|||.
synLT-A    597 TAACGAGGAAACTCAGAATCTTAGTACCATCTACTTGAGGGAATACCAAA   646

E. coli    701 caaaagttaagaggcagatattttcagactatcagtcagaggttgacata   750
               ..||.||.||.||.||||||||.||.||.||.||.||||||||||||||.
synLT-A    647 GCAAGGTGAAAAGACAGATATTCTCTGATTACCAATCAGAGGTTGACATC   696

E. coli    751 tataacagaattcgggatgaattatga    777
               ||.|||||.|||.||||||||.|.|..
synLT-A    697 TACAACAGGATTAGGGATGAACTCTAG    723
```

SEQ ID NOS: 43 AND 44

Sequence comparison of E. coli wildtype LT-B versus synthetic LT-B designed for soybean

```
E. coli      1 atgaataaagtaaaatgttatgttttatttacggcgttactatcctctct   50 synLT-B      1                                                      0

E. coli     51 atatgcacacggagctccccagactattacagaactatgttcggaatatc   100
                     .||.|  ||.||.|||||.||||||||.||.||.||.||.|||.
synLT-B      1       CCATG--GCCCCTCAGACCATTACAGAGCTTTGCTCCGAGTATA   42

E. coli    101 gcaacacacaaatatatacgataaatgacaagatactatcatatacggaa   150
               |.|||||.|||||.||.||.|||||.||||||||.||.|||||.||.||.
synLT-B     43 GGAACACCCAAATCTACACCATAAACGACAAGATCCTGTCATACACTGAG   92

E. coli    151 tcgatggcaggcaaaagagaaatggttatcattacatttaagagcggcga   200
               ...|||||.||.||.||.||.|||||.||.||.||.||||||..||||||
synLT-B     93 AGCATGGCCGGGAAGAGGGAGATGGTCATAATCACCTTTAAGTCCGGCGA   142
```

Fig. 25H

```
E. coli    201 aacatttcaggtcgaagtcccgggcagtcaacatatagactcccagaaaa    250
               |||.||.|||||||||||.||.||.||.||.|||||.||||||||.||.|
synLT-B    143 AACCTTCCAGGTCGAAGTGCCCGGTAGCCAGCATATCGACTCCCAAAAGA    192

E. coli    251 aagccattgaaaggatgaaggacacattaagaatcacatatctgaccgag    300
               |.||||||||.|||||||||||||||.||..|.||.||.||.||.||.|||
synLT-B    193 AGGCCATTGAGAGGATGAAGGACACCTTGCGCATTACTTACCTTACTGAG    242

E. coli    301 accaaaattgataaattatgtgtatggaataataaaacccccaattcaat    350
               ||.||.||.||.|||.|.||.||.|||||.||.||.||.||.||.||.||
synLT-B    243 ACTAAGATCGACAAACTCTGCGTGTGGAACAACAAGACTCCAAACTCTAT    292

E. coli    351 tgcggcaatcagtatgaaaaactag         375
               .||.|||||.||.|||||.||||||
synLT-B    293 CGCTGCAATTAGCATGAAGAACTAGTCTAGA   323
```

SEQ ID NOS: 46 and 47

Fig. 25I

A. Duplex PCR
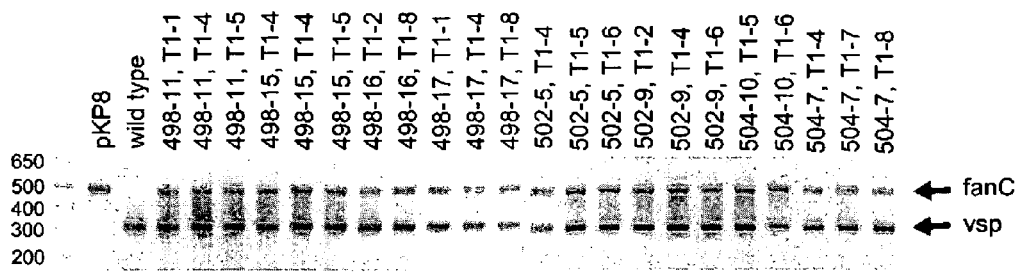
B. Western
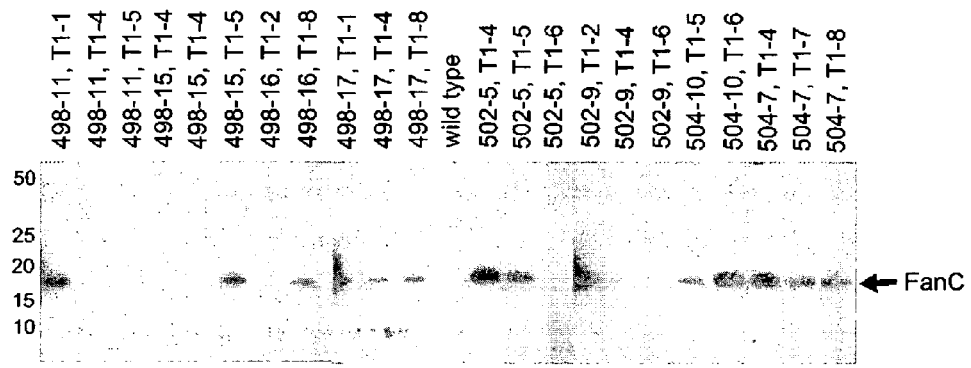
Fig. 26

SEQUENCE LISTING

<160> NUMBER OF SEQ ID NOS: 56

<210> SEQ ID NO 1
<211> LENGTH: 82
<212> TYPE: DNA
<213> ORGANISM: Artificial Sequence
<220> FEATURE:
<223> OTHER INFORMATION: Synthetic

<400> SEQUENCE: 1

```
tcatgaatac aggcactatc aactttaacg gaaagattac ttccgcgacg tgcacaatcg      60
accccgaggt gaacggaaat cg                                              82
```

<210> SEQ ID NO 2
<211> LENGTH: 100
<212> TYPE: DNA
<213> ORGANISM: Artificial Sequence
<220> FEATURE:
<223> OTHER INFORMATION: Synthetic

<400> SEQUENCE: 2

```
cacggcacgg ttgtagactt taagctcaag ccagccctg gctctaacga ctgcttggcc      60
aagacaaacg ctcggattga ctggtcgggc tcgatgaact                          100
```

<210> SEQ ID NO 3
<211> LENGTH: 70
<212> TYPE: DNA
<213> ORGANISM: Artificial Sequence
<220> FEATURE:
<223> OTHER INFORMATION: Synthetic

<400> SEQUENCE: 3
caataacact gctagcggca ataccgctgc caaagggtat cacatgaccc tacgtgcgac    60
taacgtggga                                                           70

<210> SEQ ID NO 4
<211> LENGTH: 100
<212> TYPE: DNA
<213> ORGANISM: Artificial Sequence
<220> FEATURE:
<223> OTHER INFORMATION: Synthetic

<400> SEQUENCE: 4
tcattcacca cggcggaata cacccacact tcggctatac agtccttcaa ctattccgcc    60
caacttaaga aagacgatag ggcaccttct aacggagggt                         100

<210> SEQ ID NO 5
<211> LENGTH: 96
<212> TYPE: DNA
<213> ORGANISM: Artificial Sequence
<220> FEATURE:
<223> OTHER INFORMATION: Synthetic

<400> SEQUENCE: 5
tctagagctc gtcctwcata taggtcacga ggaatgacgc gctggtcgtg aagactcccg    60
ccttataccc tccgttagaa ggtgccctat cgtctt                              96

<210> SEQ ID NO 6
<211> LENGTH: 93
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (93)..(93)
<223> OTHER INFORMATION: n is a, c, g, or t

<400> SEQUENCE: 6
agtgtgggtg tattccgccg tggtgaatga agtgttgatg ttcgcaccac cactaccgtt    60
tcccacgtta gtcgcacgta gggtcatgtg sdn                                 93

<210> SEQ ID NO 7
<211> LENGTH: 69
<212> TYPE: DNA
<213> ORGANISM: Artificial Sequence
<220> FEATURE:
<223> OTHER INFORMATION: Synthetic

<400> SEQUENCE: 7
gcagcggtat tgccgctagc agtgttattg aatccaagcg agttcatcga gcccgaccag    60
tcaatccga                                                            69

<210> SEQ ID NO 8
<211> LENGTH: 100
<212> TYPE: DNA
<213> ORGANISM: Artificial Sequence -continued

```
<220> FEATURE:
<223> OTHER INFORMATION: Synthetic

<400> SEQUENCE: 8
cttgagctta aagtctacaa ccgtgccgtg tccactgatc gcggcctggc ccaggtcgat    60
agtggatgtg cgatttccgt tcacctcggg gtcgattgtg                        100

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gccctttcat gaatacaggc ac                                            22

<210> SEQ ID NO 10
<211> LENGTH: 26
<212> TYPE: DNA
<213> ORGANISM: Artificial Sequence
<220> FEATURE:
<223> OTHER INFORMATION: Synthetic

<400> SEQUENCE: 10
gctctagagc tcgtccttca tatagg                                        26

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
cggaaagatt acttccgcga cg                                            22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
tagggcacct tctaacggag gg                                            22

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
taggtcacga ggaatgacgc gc                                            22

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
```

```
tcgattgtgc acgtcgcgga ag                                                    22

<210> SEQ ID NO 15
<211> LENGTH: 49
<212> TYPE: DNA
<213> ORGANISM: Artificial Sequence
<220> FEATURE:
<223> OTHER INFORMATION: Synthetic

<400> SEQUENCE: 15
acatatgcat catcatcatc atcatggtat gaatacaggc actatcaac                       49

<210> SEQ ID NO 16
<211> LENGTH: 34
<212> TYPE: DNA
<213> ORGANISM: Artificial Sequence
<220> FEATURE:
<223> OTHER INFORMATION: Synthetic

<400> SEQUENCE: 16
gatctagact acatataggt cacgaggaat gacg                                       34

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gcttccacac atgggagcag                                                       20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
cctctgtggt ctccaagcag                                                       20

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
cggcatagat aacaccgtac tc                                                    22

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
agtctctggc aatgccggtg                                                       20

<210> SEQ ID NO 21
<211> LENGTH: 22
<212> TYPE: DNA
<213> ORGANISM: Artificial Sequence
```

```
<220> FEATURE:
<223> OTHER INFORMATION: Synthetic

<400> SEQUENCE: 21
tggtatcgtg tgaacttcgg tg                                              22

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
cgaagtattc gttgtgtcct ctg                                             23

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
gtacctgtcg cggtattcac gg                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
ctgtcataca ctgagagcat gg                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
ttgggtgttc ctatactcgg ag                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
gttcttcatg ctaattgcag cg                                              22

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
actaagggtt tcttatatgc tc                                              22
```

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
tgctgcaata gaagtagaat gc                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
agctgggcaa tggaatccga gg                                              22

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30
gccctttggt cttctgagac tg                                              22

<210> SEQ ID NO 31
<211> LENGTH: 22
<212> TYPE: DNA
<213> ORGANISM: Artificial Sequence
<220> FEATURE:
<223> OTHER INFORMATION: Synthetic

<400> SEQUENCE: 31
acgttgcggt tctgtcagtt cc                                              22

<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32
aaacgatcca gatccggtgc ag                                              22

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
ggacaagcgc ctcttcatct c                                               21

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
aggtacacct cgatcttcac g                                              21

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tccgttgtgc tcagtcacgc                                                20

<210> SEQ ID NO 36
<211> LENGTH: 740
<212> TYPE: DNA
<213> ORGANISM: Artificial Sequence
<220> FEATURE:
<223> OTHER INFORMATION: Synthetic

<400> SEQUENCE: 36
tagggaatgg ctatgttttc tggtgattcc acggaactaa aaataatat cgaacaatgg      60 agaatctaga tgaaaaaaac actgctagct attatcttag gtggtatggc ttttgcgact    120
accaatgctt ctgcgaatac aggtactatt aacttcaatg gcaaataac gagtgctact    180 tgtacaattg accctgaggt caatggtaat cgtacatcaa ctatagatct tgggcaggct    240
gctattagtg gtcatggcac tgtagtggat tttaaactaa aaccagcgcc cggcagtaat    300
gactgcctag cgaaaacaaa tgctcgtatt gactggtctg gttctatgaa cagtttaggt    360
tttaataata cagcttcagg aaatactgct gctaaaggat accatatgac tttgcgcgca    420
acaaacgttg gaaatgggtc tggtggtgct aatattaata cttcattcac tacggctgaa    480
tacactcaca cttctgcaat tcagtcattt aactattcag cccagctgaa aaaagatgac    540
cgcgctccgt ctaatggtgg atataaagct ggcgtattta ctacttcagc atccttctta    600
gtcacttata tgtaatattt aaagtatttt acattgcggg catatctatg attgcccgca    660
atattactga tggatattat atgaatagaa aaaaacatca gattttaaaa attttattgt    720
tgtgtctaat aagcagtaaa                                               740

<210> SEQ ID NO 37
<211> LENGTH: 497
<212> TYPE: DNA
<213> ORGANISM: Artificial Sequence
<220> FEATURE:
<223> OTHER INFORMATION: Synthetic

<400> SEQUENCE: 37
tcatgaatac aggcactatc aactttaacg gaaagattac ttccgcgacg tgcacaatcg     60
accccgaggt gaacggaaat cgcacatcca ctatcgacct gggccaggcc gcgatcagtg    120
gacacggcac ggttgtagac tttaagctca agccagcccc tggctctaac gactgcttgg    180
ccaagacaaa cgctcggatt gactggtcgg gctcgatgaa ctcgcttgga ttcaataaca    240
ctgctagcgg caataccgct gccaaagggt atcacatgac cctacgtgcg actaacgtgg    300
gaaacggtag tggtggtgcg aacatcaaca cttcattcac cacggcggaa tacacccaca    360
cttcggctat acagtccttc aactattccg cccaacttaa gaaagacgat agggcacctt    420
ctaacggagg gtataaggcg ggagtcttca cgaccagcgc gtcattcctc gtgacctata    480
tgtaggacga gctctag                                                        497

<210> SEQ ID NO 38
<211> LENGTH: 160
<212> TYPE: PRT
<213> ORGANISM: Artificial Sequence
<220> FEATURE:
<223> OTHER INFORMATION: Synthetic

<400> SEQUENCE: 38

Met Asn Thr Gly Thr Ile Asn Phe Asn Gly Lys Ile Thr Ser Ala Thr
1               5                   10                  15

Cys Thr Ile Asp Pro Glu Val Asn Gly Asn Arg Thr Ser Thr Ile Asp
                20                  25                  30

Leu Gly Gln Ala Ala Ile Ser Gly His Gly Thr Val Val Asp Phe Lys
            35                  40                  45

Leu Lys Pro Ala Pro Gly Ser Asn Asp Cys Leu Ala Lys Thr Asn Ala
        50                  55                  60

Arg Ile Asp Trp Ser Gly Ser Met Asn Ser Leu Gly Phe Asn Asn Thr
65                  70                  75                  80

Ala Ser Gly Asn Thr Ala Ala Lys Gly Tyr His Met Thr Leu Arg Ala
                85                  90                  95

Thr Asn Val Gly Asn Gly Ser Gly Gly Ala Asn Ile Asn Thr Ser Phe
            100                 105                 110

Thr Thr Ala Glu Tyr Thr His Thr Ser Ala Ile Gln Ser Phe Asn Tyr
        115                 120                 125

Ser Ala Gln Leu Lys Lys Asp Asp Arg Ala Pro Ser Asn Gly Gly Tyr
    130                 135                 140

Lys Ala Gly Val Phe Thr Thr Ser Ala Ser Phe Leu Val Thr Tyr Met
145                 150                 155                 160

<210> SEQ ID NO 39
<211> LENGTH: 735
<212> TYPE: DNA
<213> ORGANISM: Artificial Sequence
<220> FEATURE:
<223> OTHER INFORMATION: Synthetic

<400> SEQUENCE: 39
atggcttcta tgatatcctc ttccgctgtg acaacagtca gccgtgcctc tagggggcaa      60
tccgccgcaa tggctccatt cggcggcctc aaatccatga ctggattccc agtgaggaag     120
gtcaacactg acattacttc cattacaagc aatggtggaa gagtaaagtg catgcaggtg     180
tggcctccaa ttggaaagaa gaagtttgag actctttcct atttgccacc attgacgaga     240
gattcccggg ccatgaatac aggcactatc aactttaacg gaaagattac ttccgcgacg     300
tgcacaatcg accccgaggt gaacggaaat cgcacatcca ctatcgacct gggccaggcc     360
gcgatcagtg gacacggcac ggttgtagac tttaagctca agccagcccc tggctctaac     420
gactgcttgg ccaagacaaa cgctcggatt gactggtcgg gctcgatgaa ctcgcttgga     480
ttcaataaca ctgctagcgg caataccgct gccaaagggt atcacatgac cctacgtgcg     540
actaacgtgg gaaacggtag tggtggtgcg aacatcaaca cttcattcac cacggcggaa     600
tacacccaca cttcggctat acagtccttc aactattccg cccaacttaa gaaagacgat     660
agggcacctt ctaacggagg gtataaggcg ggagtcttca cgaccagcgc gtcattcctc     720
gtgacctata tgtag                                                      735

<210> SEQ ID NO 40
<211> LENGTH: 809
<212> TYPE: DNA
<213> ORGANISM: Artificial Sequence
<220> FEATURE:
<223> OTHER INFORMATION: Synthetic

<400> SEQUENCE: 40

```
ccatggacaa gcgcctcttc atctcacacg tgatcctcat cttcgctctt atcctcgtga     60
tctcaactcc aaacgtgctt gctgagtcac agccagaccc aagccagac gagttgcaca    120
agtcatctaa gttcactggc aggatggaga acatgaaggt gctttacgac dcaaccacg    180
tgtctgctat caacgtgaag tcaatcgacc agttccttta cttcgacctc atctactcta    240
tcaaggacac aaagctcggc aacgccgaca acgtgagggt ggagttcaag aacaaggacc    300
ttgctgacaa gtacaaggac aagtacgtgg acgtgttcgg cgccaactac tactaccagt    360
gctacttctc taagaagacc aacgacatca actctcacca gacagacaag aggaagacat    420
gcatgtacgg cggcgtgact gagcacaacg gaaaccagct tgacaagtac aggtctatca    480
ccgtgagggt gttcgaggac ggaaagaacc ttctttcttt cgacgtgcag acaaacaaga    540
agaaggtgac cgcccaggag ctggactacc ttaccaggca ctaccttgtg aagaacaaga    600
agctctacga gttcaacaac tcaccatacg agaccggata catcaagttc atcgagaacg    660
agaactcttt ctggtacgac atgatgcccg cccctggtga caagttcgac cagtctaagt    720
accttatgat gtacaacgac aacaagatgg tggactctaa ggacgtgaag atcgaggtgt    780
accttactac taagaagaag taatctaga                                      809
```

<210> SEQ ID NO 41
<211> LENGTH: 266
<212> TYPE: PRT
<213> ORGANISM: Staphylococcus aureus

<400> SEQUENCE: 41

```
Met Asp Lys Arg Leu Phe Ile Ser His Val Ile Leu Ile Phe Ala Leu
1               5                   10                  15

Ile Leu Val Ile Ser Thr Pro Asn Val Leu Ala Glu Ser Gln Pro Asp
            20                  25                  30

Pro Lys Pro Asp Glu Leu His Lys Ser Ser Lys Phe Thr Gly Arg Met
        35                  40                  45

Glu Asn Met Lys Val Leu Tyr Asp Asp Asn His Val Ser Ala Ile Asn
    50                  55                  60

Val Lys Ser Ile Asp Gln Phe Leu Tyr Phe Asp Leu Ile Tyr Ser Ile
65                  70                  75                  80

Lys Asp Thr Lys Leu Gly Asn Ala Asp Asn Val Arg Val Glu Phe Lys
                85                  90                  95

Asn Lys Asp Leu Ala Asp Lys Tyr Lys Asp Lys Tyr Val Asp Val Phe
            100                 105                 110

Gly Ala Asn Tyr Tyr Tyr Gln Cys Tyr Phe Ser Lys Lys Thr Asn Asp
        115                 120                 125

Ile Asn Ser His Gln Thr Asp Lys Arg Lys Thr Cys Met Tyr Gly Gly
    130                 135                 140

Val Thr Glu His Asn Gly Asn Gln Leu Asp Lys Tyr Arg Ser Ile Thr
145                 150                 155                 160

Val Arg Val Phe Glu Asp Gly Lys Asn Leu Leu Ser Phe Asp Val Gln
                165                 170                 175

Thr Asn Lys Lys Lys Val Thr Ala Gln Glu Leu Asp Tyr Leu Thr Arg
```

```
                    180             185             190
His Tyr Leu Val Lys Asn Lys Lys Leu Tyr Glu Phe Asn Asn Ser Pro
        195                 200                 205

Tyr Glu Thr Gly Tyr Ile Lys Phe Ile Glu Asn Glu Asn Ser Phe Trp
    210                 215                 220

Tyr Asp Met Met Pro Ala Pro Gly Asp Lys Phe Asp Gln Ser Lys Tyr
225                 230                 235                 240

Leu Met Met Tyr Asn Asp Asn Lys Met Val Asp Ser Lys Asp Val Lys
                245                 250                 255

Ile Glu Val Tyr Leu Thr Thr Lys Lys Lys
            260                 265

<210> SEQ ID NO 42
<211> LENGTH: 1434
<212> TYPE: DNA
<213> ORGANISM: Escherica coli

<400> SEQUENCE: 42
ggatccgtca tgttgcatat aggttaaaca aaacaagtgg cgttatcttt ttccggattg      60
tcttcttgta tgatatataa gttttcctcg atgaaaaata taactttcat ttttttttatt    120 ttattagcat cgccattata tgcaaatggc gacaaattat accgtgctga ctctagaccc     180
ccagatgaaa taaaacgttc cggaggtctt atgcccagag gcataatga gtacttcgat      240 agaggaactc aaatgaatat taatctttat gatcacgcga gaggaacaca aaccggcttt    300
gtcagatatg atgacggata tgtttccact tctcttagtt tgagaagtgc tcacttagca    360
ggacagtcta tattatcagg atattccact tactatatat atgttatagc gacagcacca    420
aatatgttta tgttaatga tgtattaggc gtatacagcc ctcacccata tgaacaggag     480
gtttctgcgt taggtggaat accatattct cagatatatg gatggtatcg tgttaatttt    540
ggtgtaattg atgaacgatt acatcgtaac agggaatata gagaccggta ttacagaaat    600
ctgaatatag ctccggcaga ggatggttac agattagcag gtttcccacc ggatcaccaa    660
gcttggagag aagaaccctg gattcatcat gcaccacaag gttgtggaaa ttcatcaaga    720
acaattacag atgatacttg taatgaggag acccagaatc tgagcacaat atatctcagg    780
aaatatcaat caaagttaa gaggcagata ttttcagact atcagtcaga ggttgacata      840
tataacagaa ttcgggatga attatgaata agtaaaatg ttatgtttta tttacggcgt     900
tactatcctc tctatgtgca tacggagctc cccagtctat tacagaacta tgttcggaat    960
atcgcaacac acaaatatat acgataaatg acaagatact atcatatacg gaatcgatgg   1020
caggtaaaag agaaatggtt atcattacat ttaagagcgg cgcaacattt caggtcgaag   1080
tcccgggcag tcaacatata gactcccaaa aaaagccat gaaaggatg aaggacacat      1140 taagaatcac atatctgacc gagaccaaaa ttgataaatt atgtgtatgg aataataaaa   1200
cccccaattc aattgcggca atcagtatgg aaaactagtt tgctttaaaa gcatgtctaa   1260
tgctaggaac ctatataaca actactgtac ttatactaat gagccttatg ctgcatttga   1320
aaaggcggta gaggatgcaa taccgatcct taaactgtaa cactataaca gcttccacta   1380
cagggagctg ttatagcaca cagaaaaaac taagctaggc tgggggggcaa gctt         1434

<210> SEQ ID NO 43
<211> LENGTH: 723
<212> TYPE: DNA
<213> ORGANISM: Artificial Sequence
<220> FEATURE:
```

<223> OTHER INFORMATION: Synthetic

<400> SEQUENCE: 43

```
atgggtgata gactctatcg tgctgactct aggccacctg atgagatcaa gcgctcaggg      60
ggcttgatgc ccagaggaca caacgaatac ttcgataggg gtactcaaat gaacatcaat     120
ctctatgacc acgcaagagg aacccagaca ggttttgtta gatatgatga cggctacgtg     180
tccactagtc tgtctcttag gagcgctcat ctagccgggc aatccatctt gagtggatac     240
tcaacctact acatctacgt cattgcaaca gccccaaaca tgttcaacgt gaatgatgtg     300
ttaggcgtgt actctccaca cccttatgag caggaagtta gcgctctcgg aggtattcct     360
tactcacaaa tctacgggtg gtatcgtgtg aacttcggtg tcattgatga gaggcttcat     420
agaaaccgtg aataccgcga caggtactac cgtaacttga acatagctcc cgcagaggat     480
ggataccgcc tggccggttt cccacctgat caccaggctt ggagagagga accttggatt     540
catcatgcac acaaggctg cggaaactct tccggtacta tcaccgggga cacatgtaac      600
gaggaaactc agaatcttag taccatctac ttgagggaat accaaagcaa ggtgaaaaga     660
cagatattct ctgattacca atcagaggtt gacatctaca acaggattag ggatgaactc     720
tag                                                                    723
```

<210> SEQ ID NO 44
<211> LENGTH: 777
<212> TYPE: DNA
<213> ORGANISM: Escherica coli

<400> SEQUENCE: 44

```
atgaaaaata taactttcat ttttttttatt ttattagcat cgccattata tgcaaatggc      60
gacagattat accgtgctga ctctagaccc ccagatgaaa taaaacgttc cggaggtctt     120
atgcccagag gcataatgag gtacttcgat agaggaactc aaatgaatat taatctttat     180
gatcacgcga gaggaacaca aaccggcttt gtcagatatg atgacggata tgtttccact     240
tctcttagtt tgagaagtgc tcacttagca ggacagtcta tattatcagg atattccact     300
tactatatat atgttatagc gacagcacca aatatgttta atgttaatga tgtattaggc     360
gtatacagcc ctcacccata tgaacaggag gtttctgcgt taggtggaat accatattct     420
cagatatatg gatggtatcg tgttaatttt ggtgtgattg atgaacgatt acatcgtaac     480
agggaatata gagaccggta ttacagaaat ctgaatatag ctccggcaga ggatggttac     540
agattagcag gtttcccacc ggatcaccaa gcttggagag aagaaccctg gattcatcat     600
gcaccacaag gttgtggaaa ttcatcaaga acaatcacag gtgatacttg taatgaggag     660
acccagaatc tgagcacaat atatctcagg gaatatcaat caaaagttaa gaggcagata     720
ttttcagact atcagtcaga ggttgacata tataacagaa ttcgggatga attatga      777
```

<210> SEQ ID NO 45
<211> LENGTH: 240
<212> TYPE: PRT
<213> ORGANISM: Artificial Sequence
<220> FEATURE:
<223> OTHER INFORMATION: Synthetic

<400> SEQUENCE: 45

```
Met Gly Asp Arg Leu Tyr Arg Ala Asp Ser Arg Pro Pro Asp Glu Ile
1               5                   10                  15
Lys Arg Ser Gly Gly Leu Met Pro Arg Gly His Asn Glu Tyr Phe Asp
            20                  25                  30
```

Arg Gly Thr Gln Met Asn Ile Asn Leu Tyr Asp His Ala Arg Gly Thr
                35                  40                  45

Gln Thr Gly Phe Val Arg Tyr Asp Asp Gly Tyr Val Ser Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
                100                 105                 110

Val Ser Ala Leu Gly Gly Ile Pro Tyr Ser Gln Ile Tyr Gly Trp Tyr
            115                 120                 125

Arg Val Asn Phe Gly Val Ile Asp Glu Arg Leu His Arg Asn Arg Glu
            130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Gly
                180                 185                 190

Thr Ile Thr Gly Asp Thr Cys Asn Glu Glu Thr Gln Asn Leu Ser Thr
            195                 200                 205

Ile Tyr Leu Arg Glu Tyr Gln Ser Lys Val Lys Arg Gln Ile Phe Ser
    210                 215                 220

Asp Tyr Gln Ser Glu Val Asp Ile Tyr Asn Arg Ile Arg Asp Glu Leu
225                 230                 235                 240

<210> SEQ ID NO 46
<211> LENGTH: 323
<212> TYPE: DNA
<213> ORGANISM: Artificial Sequence
<220> FEATURE:
<223> OTHER INFORMATION: Synthetic

<400> SEQUENCE: 46
ccatggcccc tcagaccatt acagagcttt gctccgagta taggaacacc caaatctaca      60
ccataaacga caagatcctg tcatacactg agagcatggc cgggaagagg gagatggtca     120
taatcacctt taagtccggc gaaaccttcc aggtcgaagt gcccggtagc cagcatatcg     180
actcccaaaa gaaggccatt gagaggatga aggacaccct tgcgcattact taccttactg     240 agactaagat cgacaaactc tgcgtgtgga caacaagac tccaaactct atcgctgcaa      300
ttagcatgaa gaactagtct aga                                              323

<210> SEQ ID NO 47
<211> LENGTH: 375
<212> TYPE: DNA
<213> ORGANISM: Escherica coli

<400> SEQUENCE: 47
atgaataaag taaatgtta tgttttattt acggcgttac tatcctctct atatgcacac        60
ggagctcccc agactattac agaactatgt tcggaatatc gcaacacaca atatatacg      120 ataaatgaca agatactatc atatacggaa tcgatggcag gcaaaagaga atggttatc     180 attcacttta gagcggcga acatttcag gtcgaagtcc cggcagtca acatatagac       240 tcccagaaaa aagccattga aggatgaag gacacattaa gaatcacata tctgaccgag     300

```
accaaaattg ataaattatg tgtatggaat aataaaaccc ccaattcaat tgcggcaatc    360
agtatgaaaa actag                                                    375
```

<210> SEQ ID NO 48
<211> LENGTH: 104
<212> TYPE: PRT
<213> ORGANISM: Artificial Sequence
<220> FEATURE:
<223> OTHER INFORMATION: Synthetic

<400> SEQUENCE: 48

```
Met Ala Pro Gln Thr Ile Thr Glu Leu Cys Ser Glu Tyr Arg Asn Thr
1               5                  10                  15
Gln Ile Tyr Thr Ile Asn Asp Lys Ile Leu Ser Tyr Thr Glu Ser Met
            20                  25                  30
Ala Gly Lys Arg Glu Met Val Ile Ile Thr Phe Lys Ser Gly Glu Thr
        35                  40                  45
Phe Gln Val Glu Val Pro Gly Ser Gln His Ile Asp Ser Gln Lys Lys
    50                  55                  60
Ala Ile Glu Arg Met Lys Asp Thr Leu Arg Ile Thr Tyr Leu Thr Glu
65                  70                  75                  80
Thr Lys Ile Asp Lys Leu Cys Val Trp Asn Asn Lys Thr Pro Asn Ser
                85                  90                  95
Ile Ala Ala Ile Ser Met Lys Asn
            100
```

<210> SEQ ID NO 49
<211> LENGTH: 688
<212> TYPE: DNA
<213> ORGANISM: Apis mellifera

<400> SEQUENCE: 49

```
gtgctctcgc gtactctgtg aaaatcaccg gaaggaaccg cttttcgcct cgctcctcga     60
ccatttccca ttcaaagagg ctctccttcc tcttcttgta acctccgctt cccttctttct   120 cctcttctcc cacgatgcaa gtcgttctcg gatccttgtt ccttctcctc ctctctacct    180
ctcacggatg gcaaatcagg gataggatcg gggataacga gttggaggaa cggataatat    240
atccaggaac gttatggtgc gggcatggta acaagtcgtc cggcccgaac gagctaggtc    300
ggttcaagca cacggatgca tgctgtcgaa cccacgacat gtgcccggac gtgatgtcag    360
ctggtgaatc gaagcacggc ctgaccaaca cggcctccca ccaggttg tcgtgcgact      420 gcgacgacaa gttctatgat tgtcttaaaa attcggcgga cacgattagc tcgtatttcg    480
tagggaagat gtacttcaat ctgatagaca cgaagtgtta caaactggag catcctgtca    540
ccgggtgcgg tgagagaacc gagggtcgtt gtcttcacta caccgtggac aaaagcaaac    600
cgaaagtgta ccaatggttc gatcttcgca agtattgata aattcacggg gcggatcttg    660
agagtaccac ttcgagatcg tttattta                                      688
```

<210> SEQ ID NO 50
<211> LENGTH: 416
<212> TYPE: DNA
<213> ORGANISM: Artificial Sequence
<220> FEATURE:
<223> OTHER INFORMATION: Synthetic

<400> SEQUENCE: 50

```
tcatgatcat ctatcctgga accttgtggt gcggacatgg taacaagtca tcaggtccaa     60
```

-continued

```
atgagttggg gaggttcaag cacacagacg cctgttgcag gacacaggat atgtgtccag      120
atgtgatgag cgctggcgaa tcaaagcacg gtttgacaaa caccgcttct catactcgtc      180
tctcttgtga ttgtgatgac aagttttacg attgtctgaa gaactccgct gacactattt      240
cttcctattt cgtgggtaag atgtacttca acttgataga taccaagtgc tacaagctgg      300
aacaccctgt gactggctgc ggagaaagga ccgaaggtag gtgccttcac tacaccgtgg      360
acaaatcaaa gcccaaagtt tatcagtggt tcgatctgcg caaatactaa tctaga         416
```

<210> SEQ ID NO 51
<211> LENGTH: 135
<212> TYPE: PRT
<213> ORGANISM: Artificial Sequence
<220> FEATURE:
<223> OTHER INFORMATION: Synthetic

<400> SEQUENCE: 51

```
Met Ile Ile Tyr Pro Gly Thr Leu Trp Cys Gly His Gly Asn Lys Ser
1               5                   10                  15

Ser Gly Pro Asn Glu Leu Gly Arg Phe Lys His Thr Asp Ala Cys Cys
            20                  25                  30

Arg Thr Gln Asp Met Cys Pro Asp Val Met Ser Ala Gly Glu Ser Lys
        35                  40                  45

His Gly Leu Thr Asn Thr Ala Ser His Thr Arg Leu Ser Cys Asp Cys
    50                  55                  60

Asp Asp Lys Phe Tyr Asp Cys Leu Lys Asn Ser Ala Asp Thr Ile Ser
65                  70                  75                  80

Ser Tyr Phe Val Gly Lys Met Tyr Phe Asn Leu Ile Asp Thr Lys Cys
                85                  90                  95

Tyr Lys Leu Glu His Pro Val Thr Gly Cys Gly Glu Arg Thr Glu Gly
            100                 105                 110

Arg Cys Leu His Tyr Thr Val Asp Lys Ser Lys Pro Lys Val Tyr Gln
        115                 120                 125

Trp Phe Asp Leu Arg Lys Tyr
    130                 135
```

<210> SEQ ID NO 52
<211> LENGTH: 666
<212> TYPE: PRT
<213> ORGANISM: Artificial Sequence
<220> FEATURE:
<223> OTHER INFORMATION: Synthetic

<400> SEQUENCE: 52

```
Ser Glu Gln Ile Asp Asn Met Arg Pro Arg Pro Ile Leu Leu Leu Leu
1               5                   10                  15

Leu Met Phe Leu Pro Met Leu Pro Ala Pro Pro Gly Gln Pro Ser
            20                  25                  30

Gly Arg Arg Gly Arg Arg Ser Gly Gly Ser Gly Gly Phe Trp
        35                  40                  45

Gly Asp Arg Val Asp Ser Gln Pro Phe Ala Ile Pro His Ile His Pro
    50                  55                  60

Thr Asn Pro Phe Ala Pro Asp Val Thr Ala Ala Gly Ala Gly Pro
65                  70                  75                  80

Arg Val Arg Gln Pro Ala Arg Pro Leu Gly Ser Ala Trp Arg Asp Gln
                85                  90                  95

Ala Gln Arg Pro Ala Ala Thr Ser Arg Arg Arg Pro Thr Thr Ala Gly
```

-continued

```
                100                 105                 110
Ala Ala Pro Leu Thr Ala Val Ala Pro Ala His Asp Thr Pro Pro Val
            115                 120                 125
Pro Asp Val Asp Ser Arg Gly Ala Ile Leu Arg Arg Gln Tyr Asn Leu
        130                 135                 140
Ser Thr Ser Pro Leu Thr Ser Pro Val Ala Thr Gly Thr Asn Leu Val
145                 150                 155                 160
Leu Tyr Ala Ala Pro Leu Ser Pro Leu Leu Pro Leu Gln Asp Gly Thr
                165                 170                 175
Asn Thr His Ile Met Ala Thr Glu Ala Ser Asn Tyr Ala Gln Tyr Arg
            180                 185                 190
Val Ala Arg Ala Thr Ile Arg Tyr Arg Pro Leu Val Pro Asn Ala Val
        195                 200                 205
Gly Gly Tyr Ala Ile Ser Ile Ser Phe Trp Pro Gln Thr Thr Thr Thr
    210                 215                 220
Pro Thr Ser Val Asp Met Asn Ser Ile Thr Ser Thr Asp Val Arg Ile
225                 230                 235                 240
Leu Val Gln Pro Gly Ile Ala Ser Glu Leu Val Ile Pro Ser Glu Arg
                245                 250                 255
Leu His Tyr Arg Asn Gln Gly Trp Arg Ser Val Glu Thr Ser Gly Val
            260                 265                 270
Ala Glu Glu Ala Thr Ser Gly Leu Val Met Leu Cys Ile His Gly
        275                 280                 285
Leu Pro Val Asn Ser Tyr Thr Asn Thr Pro Tyr Thr Gly Ala Leu Gly
    290                 295                 300
Leu Leu Asp Phe Ala Leu Glu Phe Glu Phe Arg Asn Leu Thr Pro Gly
305                 310                 315                 320
Asn Thr Asn Thr Arg Val Ser Arg Tyr Ser Ser Thr Ala Arg His Arg
                325                 330                 335
Leu Arg Arg Gly Ala Asp Gly Thr Ala Glu Leu Thr Thr Thr Ala Ala
            340                 345                 350
Thr Arg Phe Met Lys Asp Leu Tyr Phe Thr Ser Thr Asn Gly Val Gly
        355                 360                 365
Glu Ile Gly Arg Gly Ile Ala Leu Thr Leu Phe Asn Leu Ala Asp Thr
    370                 375                 380
Leu Leu Gly Gly Leu Pro Thr Glu Leu Ile Ser Ser Ala Gly Gly Gln
385                 390                 395                 400
Leu Phe Tyr Ser Arg Pro Val Val Ser Ala Asn Gly Glu Pro Thr Val
                405                 410                 415
Lys Leu Tyr Thr Ser Val Glu Asn Ala Gln Gln Asp Lys Gly Ile Ala
            420                 425                 430
Ile Pro His Asp Ile Asp Leu Gly Glu Ser Arg Val Val Ile Gln Asp
        435                 440                 445
Tyr Asp Asn Gln His Glu Gln Asp Arg Pro Thr Pro Ser Pro Ala Pro
    450                 455                 460
Ser Arg Pro Phe Ser Val Leu Arg Ala Asn Asp Val Leu Trp Leu Ser
465                 470                 475                 480
Leu Thr Ala Ala Glu Tyr Asp Gln Ser Thr Tyr Gly Ser Ser Thr Gly
                485                 490                 495
Pro Val Tyr Val Ser Asp Ser Val Thr Leu Val Asn Val Ala Thr Gly
            500                 505                 510
Ala Gln Ala Val Ala Arg Ser Leu Asp Trp Thr Lys Val Thr Leu Asp
        515                 520                 525
```

```
Gly Arg Pro Leu Ser Thr Ile Gln Gln Tyr Ser Lys Thr Phe Phe Val
        530                 535                 540

Leu Pro Leu Arg Gly Lys Leu Ser Phe Trp Glu Ala Gly Thr Thr Lys
545                 550                 555                 560

Ala Gly Tyr Pro Tyr Asn Tyr Asn Thr Thr Ala Ser Asp Gln Leu Leu
                565                 570                 575

Ile Glu Asn Ala Ala Gly His Arg Val Ala Ile Ser Tyr Thr Thr
                580                 585                 590

Ser Leu Gly Ala Gly Pro Val Ala Ile Ser Ala Val Ala Val Leu Ala
                595                 600                 605

Pro His Ser Ala Leu Ala Leu Leu Glu Asp Thr Met Asp Tyr Pro Ala
        610                 615                 620

Arg Ala His Thr Phe Asp Asp Phe Cys Pro Glu Cys Arg Pro Leu Gly
625                 630                 635                 640

Leu Gln Gly Cys Ala Phe Gln Ser Thr Val Ala Glu Leu Gln Arg Leu
                645                 650                 655

Lys Met Lys Val Gly Lys Thr Arg Glu Leu
                660                 665

<210> SEQ ID NO 53
<211> LENGTH: 1693
<212> TYPE: PRT
<213> ORGANISM: Artificial Sequence
<220> FEATURE:
<223> OTHER INFORMATION: Synthetic

<400> SEQUENCE: 53

Met Glu Ala His Gln Phe Ile Lys Ala Pro Gly Ile Thr Thr Ala Ile
1               5                   10                  15

Glu Gln Ala Ala Leu Ala Ala Asn Ser Ala Leu Ala Asn Ala Val
                20                  25                  30

Val Val Arg Pro Phe Leu Ser His Gln Gln Ile Glu Ile Leu Ile Asn
            35                  40                  45

Leu Met Gln Pro Arg Gln Leu Val Phe Arg Pro Glu Val Phe Trp Asn
50                  55                  60

His Pro Ile Gln Arg Val Ile His Asn Glu Leu Glu Leu Tyr Cys Arg
65                  70                  75                  80

Ala Arg Ser Gly Arg Cys Leu Glu Ile Gly Ala His Pro Arg Ser Ile
                85                  90                  95

Asn Asp Asn Pro Asn Val Val His Arg Cys Phe Leu Arg Pro Val Gly
            100                 105                 110

Arg Asp Val Gln Arg Trp Tyr Thr Ala Pro Thr Arg Gly Pro Ala Ala
            115                 120                 125

Asn Cys Arg Arg Ser Ala Leu Arg Gly Leu Ser Ala Ala Asp Arg Thr
130                 135                 140

Tyr Cys Phe Asp Gly Phe Ser Gly Cys Asn Phe Pro Ala Glu Thr Gly
145                 150                 155                 160

Ile Ala Leu Tyr Ser Leu His Asp Met Ser Pro Ser Asp Val Ala Glu
                165                 170                 175

Ala Met Phe Arg His Gly Met Thr Arg Leu Tyr Ala Ala Leu His Leu
            180                 185                 190

Pro Pro Glu Val Leu Leu Pro Pro Gly Thr Tyr Arg Thr Ala Ser Tyr
            195                 200                 205

Leu Leu Ile His Asp Gly Arg Arg Val Val Val Thr Tyr Glu Gly Asp
        210                 215                 220
```

-continued

```
Thr Ser Ala Gly Tyr Asn His Asp Val Ser Asn Leu Arg Ser Trp Ile
225                 230                 235                 240

Arg Thr Thr Lys Val Thr Gly Asp His Pro Leu Val Ile Glu Arg Val
            245                 250                 255

Arg Ala Ile Gly Cys His Phe Val Leu Leu Thr Ala Ala Pro Glu
            260                 265                 270

Pro Ser Pro Met Pro Tyr Val Pro Tyr Pro Arg Ser Thr Glu Val Tyr
            275                 280                 285

Val Arg Ser Ile Phe Gly Pro Gly Gly Thr Pro Ser Leu Phe Pro Thr
290                 295                 300

Ser Cys Ser Thr Lys Ser Thr Phe His Ala Val Pro Ala His Ile Trp
305                 310                 315                 320

Asp Arg Leu Met Leu Phe Gly Ala Thr Leu Asp Gln Ala Phe Cys
            325                 330                 335

Cys Ser Arg Leu Met Thr Tyr Leu Arg Gly Ile Ser Tyr Lys Val Thr
            340                 345                 350

Val Gly Thr Leu Val Ala Asn Glu Gly Trp Asn Ala Ser Glu Asp Ala
            355                 360                 365

Leu Thr Ala Val Ile Thr Ala Ala Tyr Leu Thr Ile Cys His Gln Arg
370                 375                 380

Tyr Leu Arg Thr Gln Ala Ile Ser Lys Gly Met Arg Arg Leu Glu Arg
385                 390                 395                 400

Glu His Ala Gln Lys Phe Ile Thr Arg Leu Tyr Ser Trp Leu Phe Glu
            405                 410                 415

Lys Ser Gly Arg Asp Tyr Ile Pro Gly Arg Gln Leu Glu Phe Tyr Ala
            420                 425                 430

Gln Cys Arg Arg Trp Leu Ser Ala Gly Phe His Leu Asp Pro Arg Val
            435                 440                 445

Leu Val Phe Asp Glu Ser Ala Pro Cys His Cys Arg Thr Ala Ile Arg
450                 455                 460

Lys Ala Val Ser Lys Phe Cys Cys Phe Met Lys Trp Leu Gly Gln Glu
465                 470                 475                 480

Cys Thr Cys Phe Leu Gln Pro Ala Glu Gly Ala Gly Asp Gln Gly
            485                 490                 495

His Asp Asn Glu Ala Tyr Glu Gly Ser Asp Val Asp Pro Ala Glu Ser
            500                 505                 510

Ala Ile Ser Asp Ile Ser Gly Ser Tyr Val Val Pro Gly Thr Ala Leu
            515                 520                 525

Gln Pro Leu Tyr Gln Ala Leu Asp Leu Pro Ala Glu Ile Val Ala Arg
530                 535                 540

Ala Gly Arg Leu Thr Ala Thr Val Lys Val Ser Gln Val Asp Gly Arg
545                 550                 555                 560

Ile Asp Cys Glu Thr Leu Leu Gly Asn Lys Thr Phe Arg Thr Ser Phe
            565                 570                 575

Val Asp Gly Ala Val Leu Glu Thr Asn Gly Pro Glu Arg His Asn Leu
            580                 585                 590

Ser Phe Asp Ala Ser Gln Ser Thr Met Ala Ala Gly Pro Phe Ser Leu
            595                 600                 605

Thr Tyr Ala Ala Ser Ala Ala Gly Leu Glu Val Arg Tyr Val Ala Ala
            610                 615                 620

Gly Leu Asp His Arg Ala Val Phe Ala Pro Gly Val Ser Pro Arg Ser
625                 630                 635                 640
```

```
Ala Pro Gly Glu Val Thr Ala Phe Cys Ser Ala Leu Tyr Arg Phe Asn
            645                 650                 655

Arg Glu Ala Gln Arg His Ala Leu Thr Gly Asn Phe Trp Phe His Pro
        660                 665                 670

Glu Gly Leu Leu Gly Leu Phe Ala Pro Phe Ser Pro Gly His Val Trp
            675                 680                 685

Glu Ser Ala Asn Pro Phe Cys Gly Glu Ser Thr Leu Tyr Thr Arg Thr
690                 695                 700

Trp Ser Glu Val Asp Ala Val Ser Ser Pro Ala Arg Pro Asp Leu Gly
705                 710                 715                 720

Phe Ala Ser Glu Pro Ser Ile Pro Ser Arg Ala Ala Thr Pro Thr Pro
                725                 730                 735

Ala Ala Leu Gln Pro Ser Ser Ala Pro Asp Pro Phe Pro Pro Pro Ser
            740                 745                 750

Ala Pro Ala Leu Gly Glu Pro Ala Pro Gly Val Thr Ala Val Ala Pro
            755                 760                 765

Ala Ile Thr His Gln Thr Ala Arg His Arg Arg Leu Leu Phe Thr Tyr
770                 775                 780

Pro Asp Gly Ser Lys Val Phe Ala Gly Ser Leu Phe Glu Ser Thr Cys
785                 790                 795                 800

Thr Trp Leu Val Asn Ala Ser Asn Val Asp His Arg Pro Gly Gly Gly
                805                 810                 815

Leu Cys His Ala Phe Tyr Gln Arg Tyr Pro Thr Ser Phe Asp Ala Ala
            820                 825                 830

Ser Phe Val Met Arg Asp Gly Ala Ala Ala Tyr Thr Leu Thr Pro Arg
            835                 840                 845

Pro Ile Ile His Ala Val Ala Pro Asp Tyr Arg Leu Glu His Asn Pro
            850                 855                 860

Lys Arg Leu Glu Ala Ala Tyr Arg Glu Thr Cys Ser Arg Leu Gly Thr
865                 870                 875                 880

Ala Ala Tyr Pro Leu Leu Gly Thr Gly Ile Tyr Gln Val Pro Ile Gly
                885                 890                 895

Pro Ser Phe Asp Ala Trp Glu Arg Asn His Arg Pro Gly Asp Glu Leu
            900                 905                 910

Tyr Leu Pro Glu Leu Ala Ala Arg Trp Phe Glu Ala Asn Arg Pro Ala
            915                 920                 925

Cys Pro Thr Leu Thr Ile Thr Glu Asp Ala Ala Arg Thr Ala Asn Leu
        930                 935                 940

Ala Ile Glu Leu Asp Ser Ala Thr Asp Val Gly Arg Ala Cys Ala Gly
945                 950                 955                 960

Cys Arg Val Thr Pro Gly Val Val Gln Tyr Gln Phe Thr Ala Gly Val
                965                 970                 975

Pro Gly Ser Gly Lys Ser Arg Ser Ile Thr Gln Ala Asp Val Asp Val
            980                 985                 990

Val Val Val Pro Thr Arg Glu Leu Arg Asn Ala Trp Arg Arg Arg Gly
        995                 1000                1005

Phe Ala Ala Phe Thr Pro His Thr Ala Ala Arg Val Thr Gln Gly
    1010                1015                1020

Arg Arg Val Val Ile Asp Glu Ala Pro Ser Leu Pro Pro His Leu
    1025                1030                1035

Leu Leu Leu His Met Gln Arg Ala Ala Thr Val His Leu Leu Gly
    1040                1045                1050

Asp Pro Asn Gln Ile Pro Ala Ile Asp Phe Glu His Ala Gly Leu
```

-continued

```
               1055                 1060                 1065
Val Pro Ala Ile Arg Pro Asp Leu Ala Pro Thr Ser Trp Trp His
    1070                1075                1080

Val Thr His Arg Cys Pro Ala Asp Val Cys Glu Leu Ile Arg Gly
    1085                1090                1095

Ala Tyr Pro Met Ile Gln Thr Thr Ser Arg Val Leu Arg Ser Leu
    1100                1105                1110

Phe Trp Gly Glu Pro Ala Val Gly Gln Lys Leu Val Phe Thr Gln
    1115                1120                1125

Ala Ala Lys Ala Ala Asn Pro Gly Ser Val Thr Val His Glu Ala
    1130                1135                1140

Gln Gly Ala Thr Tyr Thr Glu Thr Thr Ile Ile Ala Thr Ala Asp
    1145                1150                1155

Ala Arg Gly Leu Ile Gln Ser Ser Arg Ala His Ala Ile Val Ala
    1160                1165                1170

Leu Thr Arg His Thr Glu Lys Cys Val Ile Ile Asp Ala Pro Gly
    1175                1180                1185

Leu Leu Arg Glu Val Gly Ile Ser Asp Ala Ile Val Asn Asn Phe
    1190                1195                1200

Phe Leu Ala Gly Gly Glu Ile Gly His Gln Arg Pro Ser Val Ile
    1205                1210                1215

Pro Arg Gly Asn Pro Asp Thr Asn Val Asp Thr Leu Ala Ala Phe
    1220                1225                1230

Pro Pro Ser Cys Gln Ile Ser Ala Phe His Gln Leu Ala Glu Glu
    1235                1240                1245

Leu Gly His Arg Pro Ala Pro Val Ala Ala Val Leu Pro Pro Cys
    1250                1255                1260

Pro Glu Leu Glu Gln Gly Leu Leu Tyr Leu Pro Gln Glu Leu Thr
    1265                1270                1275

Thr Cys Asp Ser Val Val Thr Phe Glu Leu Thr Asp Ile Val His
    1280                1285                1290

Cys Arg Met Ala Ala Pro Ser Gln Arg Lys Ala Val Leu Ser Thr
    1295                1300                1305

Leu Val Gly Arg Tyr Gly Arg Arg Thr Lys Leu Tyr Asn Ala Ser
    1310                1315                1320

His Ser Asp Val Arg Asp Ser Leu Ala Arg Phe Ile Pro Thr Ile
    1325                1330                1335

Gly Pro Val Gln Val Thr Thr Cys Glu Leu Tyr Glu Leu Val Glu
    1340                1345                1350

Ala Met Val Glu Lys Gly Gln Asp Gly Ser Ala Val Leu Glu Leu
    1355                1360                1365

Asp Leu Cys Asn Arg Asp Val Ser Arg Ile Thr Phe Phe Gln Lys
    1370                1375                1380

Asp Cys Asn Lys Phe Thr Thr Gly Glu Thr Ile Ala His Gly Lys
    1385                1390                1395

Val Gly Gln Gly Ile Ser Ala Trp Ser Lys Thr Phe Cys Ala Leu
    1400                1405                1410

Phe Gly Pro Trp Phe Arg Ala Ile Glu Lys Ala Ile Leu Ala Leu
    1415                1420                1425

Leu Pro Gln Gly Val Phe Tyr Gly Asp Ala Phe Asp Asp Thr Val
    1430                1435                1440

Phe Ser Ala Ala Val Ala Ala Ala Lys Ala Ser Met Val Phe Glu
    1445                1450                1455
```

```
Asn Asp Phe Ser Glu Phe Asp Ser Thr Gln Asn Asn Phe Ser Leu
    1460                1465                1470

Gly Leu Glu Cys Ala Ile Met Glu Glu Cys Gly Met Pro Gln Trp
    1475                1480                1485

Leu Ile Arg Leu Tyr His Leu Ile Arg Ser Ala Trp Ile Leu Gln
    1490                1495                1500

Ala Pro Lys Glu Ser Leu Arg Gly Phe Trp Lys Lys His Ser Gly
    1505                1510                1515

Glu Pro Gly Thr Leu Leu Trp Asn Thr Val Trp Asn Met Ala Val
    1520                1525                1530

Ile Thr His Cys Tyr Asp Phe Arg Asp Leu Gln Val Ala Ala Phe
    1535                1540                1545

Lys Gly Asp Asp Ser Ile Val Leu Cys Ser Glu Tyr Arg Gln Ser
    1550                1555                1560

Pro Gly Ala Ala Val Leu Ile Ala Gly Cys Gly Leu Lys Leu Lys
    1565                1570                1575

Val Asp Phe Arg Pro Ile Gly Leu Tyr Ala Gly Val Val Val Ala
    1580                1585                1590

Pro Gly Leu Gly Ala Leu Pro Asp Val Val Arg Phe Ala Gly Arg
    1595                1600                1605

Leu Thr Glu Lys Asn Trp Gly Pro Gly Pro Glu Arg Ala Glu Gln
    1610                1615                1620

Leu Arg Leu Ala Val Ser Asp Phe Leu Arg Lys Leu Thr Asn Val
    1625                1630                1635

Ala Gln Met Cys Val Asp Val Val Ser Arg Val Tyr Gly Val Ser
    1640                1645                1650

Pro Gly Leu Val His Asn Leu Ile Gly Met Leu Gln Thr Val Ala
    1655                1660                1665

Asp Gly Lys Ala His Phe Thr Glu Ser Val Lys Pro Val Leu Asp
    1670                1675                1680

Leu Thr Asn Ser Ile Leu Cys Arg Val Glu
    1685                1690

<210> SEQ ID NO 54
<211> LENGTH: 4
<212> TYPE: PRT
<213> ORGANISM: Artificial Sequence
<220> FEATURE:
<223> OTHER INFORMATION: Synthetic

<400> SEQUENCE: 54

Lys Asp Glu Leu
1

<210> SEQ ID NO 55
<211> LENGTH: 4
<212> TYPE: PRT
<213> ORGANISM: Artificial Sequence
<220> FEATURE:
<223> OTHER INFORMATION: Sythetic

<400> SEQUENCE: 55

His Asp Glu Leu
1

<210> SEQ ID NO 56
<211> LENGTH: 4
<212> TYPE: PRT
```

-continued

```
<213> ORGANISM: Artificial Sequence
<220> FEATURE:
<223> OTHER INFORMATION: Synthetic

<400> SEQUENCE: 56

Arg Asp Glu Leu
1
```

EDIBLE VACCINES EXPRESSED IN SOYBEANS

This invention claims priority under 37 CFR 1.119(e) to U.S. Provisional Patent Application 60/617,792 filed Oct. 12, 2004, the entire contents of which is hereby incorporated by reference.

BACKGROUND OF THE INVENTION

The use of vaccines likely represents the most important, practical contribution that immunologists have made to human health. Effective vaccines establish a state of resistance to microbial diseases in the host prior to infection. Thus, vaccinations function to prevent disease, and such prophylaxis has undoubtedly saved countless lives. In fact, vaccinations have been so successful, that widespread immunizations directed against a variety of bacterial, viral, and parasitic pathogens have become the rule, once an appropriate vaccine has been identified. The most notable example of global immunization was the use of a vaccine against smallpox which eliminated this viral disease.

Ultimately, the success and practicality of widespread immunizations against a particular pathogen depends upon the characteristics of an individual vaccine. These characteristics include: 1) efficacy, i.e. the ability to induce a response that imparts some level of protection in the vast majority of individuals; 2) safety, i.e. limited side effects in immunocompetent children and/or adults; 3) method of delivery, e.g. injectable, oral, intranasal, or transdermal administration; 4) immunization regimen, i.e. single or multiple exposures; 5) stability, i.e., the shelf life and conditions needed for shipping, such as refrigeration; and 6) cost, i.e., the total expense for an immunization regimen, including vaccine production, shipping, and administration. Using these considerations, the most successful vaccines would likely be cheap to produce, highly stable for shipping, and administered in a desirable form that does not require specialized personnel for delivery.

The enormous potential for the use of plant-derived vaccines has been discussed since the first demonstration of the feasibility of such technology in the early 1990s (Mason et al. 1992. Expression of hepatitis B surface antigen in transgenic plants. *Proc Natl Acad Sci* U S A 89:11745, which is herein incorporated by reference in its entirety). An edible vaccine expressed in transgenic plants would represent a cost-effective method for production, as well as the promise of safe administration of an antigen in a highly stable form that could be shipped throughout the world. While the concept of eating a vaccine is easy to visualize, this technology is relatively new. Although some progress has been made toward demonstrating the feasibility of expressing subunit protein antigens in plants, there are drawbacks to the systems methods and use as well as some practical questions concerning the effectiveness of edible vaccines that prior to the instant invention had yet to be addressed.

Despite the promise of plant based vaccines as a low cost method for stimulating mucosal immunity, significant questions still remain about the feasibility of developing such methods for immunizing humans and animals.

Moreover, while widespread vaccination to prevent microbial diseases occurs daily throughout the world, a similar, prophylactic approach has not been used for the widespread prevention of allergic reactions and/or autoimmune antigens. Presently, immunotherapy may be used once an individual has already demonstrated a significant hypersensitivity against a particular allergen or has developed a specific autoimmune disease. However, it has seemed impractical to suggest that it might be feasible to induce tolerance toward specific allergens in individuals even before they demonstrate hypersensitivity.

A criticism for all investigators who have attempted to express vaccines in transgenic plants has been the efficacy and practicality of such immunization strategies. Often the immunogen expressed in plants has had to be purified or significantly concentrated prior to its use as a vaccine. Moreover, often the concentrated or purified plant-derived immunogen must be given parenterally or intranasally to demonstrate its ability to stimulate an immune response.

Soybeans first emerged as a domestic crop in the eastern half of China around the 11th century. Soybeans were later introduced from the Orient to Europe in the early 1700s, and then to North America in the early 1800s. Large scale introduction in the US was in the early 1900s. (from "Soybeans Chemistry, Technology, and Utilization, by KeShun Liu, Aspen Publishers, Inc. Gaithersburg, Maryland, 1999, ISBN: 0-8342-1299-4). The incorporation of recombinant nucleotide sequences into soybeans first made an appearance in 1988 see Hinchee, et al. 1988. Bio/Technology 6, 915-922. However, to the inventors knowledge, to date, no transgenic soybeans have been used or exploited for antigen production, for soy milk formulations, for use to make adjuvants, for edible vaccines in general, or for any other immunogenic purpose.

1. Field of the Invention

The field of the present invention relates to vaccines that are made in transgenic soybeans for use in humans, animals of agricultural importance, pets, and wildlife. These vaccines can be used for a plurality of purposes, such as vaccines against viral, bacterial, fungal, parasitic or prion related diseases, cancer antigens, toxins, and autologous or self proteins. Moreover, the transgenic soybeans of the instant invention can be used for inducing tolerance to allergens or tolerance to autoimmune antigens, wherein an individual shows hypersensitivity to said allergen or has developed autoimmunity to autologous or self proteins, respectively. The present invention also relates to prophylatically treating individuals and/or populations prior to showing hypersensitivity to allergens. Other aspects of the invention include using the transgenic soybeans as an oral contraceptive, and the expression of protein adjuvants in transgenic soybeans.

2. Description of Related Art

U.S. Pat. Nos. 6,034,298 and 6,136,320, both of which are incorporated herein in their entirety, disclose using a hepatitis B surface antigen, which is incorporated into potato tubers to generate an immune response. Potato tubers are known to have protein content, which is usually on the order of 2% (See http://beef.osu.edu/library/potato.html visited on Oct. 12, 2005 for a report on the protein content in potatoes). Soybeans, in contrast, have protein amounts that are on the order of 38% protein. The present invention generally has protein amounts that are equal to or above 15%, more preferably 20% and even more preferably 30%. Thus, it is noted that soybeans have more than an order of magnitude higher concentration of protein than potatoes. Because of this relatively low protein content in potatoes, one may or may not generate an immune response since it may or may not be possible to provide an effective dose without consumption of an unrealistic amount of raw potato. Generally, the immune response may be attributable to the concentration of the antigen protein, some unusual property of the antigen protein being expressed or the combinatorial use of an adjuvant to increase immune response. In U.S. Pat. Nos. 6,034,298 and 6,136,320, the immune response was triggered due to unusual properties of hepatitis B surface antigen. There are two properties that likely made the hepatic B subunit antigen immunogenic at the relatively low protein concentrations seen in potato tubers.

First, the hepatitis B subunit antigen self-associates into large polymers. This is an unusual property that is not possessed by most subunit protein antigens. In fact, the vast majority of subunit antigens (i.e. >95%) will not self-associate into such large conglomerates. It is known that large polymers are much more immunogenic than single proteins. Thus, for the hepatitis B subunit antigen, the immunogenic response was likely attained in part due to this self-association. In the absence of self association (or high concentrations), the probability of it being immunogenic when given orally would be negligible without the incorporation of an adjuvant used in conjunction with the protein antigen.

Second, the hepatitis B subunit antigen protein happens to bind to epithelial cells on mucosal surfaces. The vast majority of subunit antigens (i.e. >95%) will not have such a property. Therefore, most subunit antigens will pass right through the gut without ever interacting to any large extent with epithelial cells (unless the concentration is sufficiently high or unless the vaccine is combined with an adjuvant). Such antigens that don't bind to mucosal surfaces have a very low probability of being immunogenic without the incorporation of an adjuvant (or without having the concentration sufficiently high to overcome the poor immunogenic response). Thus, using potato or some other transgenic plant other than soybean is disadvantageous in that it generally requires the a subunit protein antigen to have some unusual property in order to get an immune response.

U.S. Pat. Nos. 6,034,298 and 6,136,320 also focus on "antigens located on the surface of a pathogenic organism", which may be a limitation of the system (i.e., potatoes) that is used. These antigens only represent a small number of viral or bacterial antigens and they are not likely to include some of the more important antigens that can be used in vaccine development. A protein does not have to be on the surface of a pathogen to be immunogenic or to provide protective immunity.

Responses of T helper lymphocytes are triggered by antigens that do not have to appear on the surface of a pathogenic organism. Memory T helper cells must be formed to have optimal antibody responses and for optimal cytotoxic T cell responses. In fact, helper T lymphocytes cannot recognize antigens on the surface of pathogen. They can recognize peptide fragments from any protein antigen from the pathogen (i.e. external, cytoplasmic, nuclear, etc.). The reason for this is that T cells don't recognize antigens directly (like antibodies do), but rather T cells must recognize proteins that have been processed into peptides and expressed on an antigen presenting cells (i.e. dendritic cells or macrophages). T helper cells recognize peptide antigens presented to them by antigen presenting cells. Thus, one good measure of a vaccine is its "processcivity", i.e., how well it can be degraded by antigen presenting cells so that it can be presented to T helper cells so they can help B lymphocytes and T cytotoxic cells perform their function. Thus, the consideration of antigens appearing (or not appearing) on the surface of a pathogenic organism is a relevant consideration to keep in mind when making a vaccine.

Similarly, T cytotoxic lymphocytes target and kill virally infected cells (without having to recognize antigens on the surface of a pathogenic organism). A primary goal of many anti-viral vaccines is to stimulate a cytotoxic T lymphocyte response to combat viral infections. T cytotoxic lymphocytes can only recognize viral peptides presented to them by the infected cell (i.e. epithelial cell) that the cytotoxic cells are trying to kill. Thus, any subunit antigen (i.e. external, internal, etc.) should be considered an appropriate vaccine candidate. The ability of a vaccine to stimulate T cytotoxic cell activity using subunit vaccines that are not expressed on the surface of the pathogen is an important consideration in designing a vaccine.

Moreover, the goal of oral vaccines is generally to induce the production of long lived T helper and B lymphocyte memory cells. Only if such memory cells are induced can a vaccine be efficacious. If a vaccine does not induce long lived memory cells, then it is likely to not be effective. Different vaccines induce different longevities of memory cells. For example, it is known that a tetanus immunization should be updated every decade or so, but the attenuate polio vaccine likely induces inmmunity for life. This is due to the nature of this particular vaccine's ability to induce very long-lived B and T memory cells. If one does not recognize these goals and drawbacks, one cannot effectively design a vaccine or propose assays to determine vaccine efficacy.

Another consideration that should be kept in mind when designing a vaccine is overcoming oral tolerance. Subunit antigens given orally which do not have special properties (i.e. high affinity for gut epithelium or endogenous adjuvant activity) will pass through the gastrointestinal tract without stimulating any detectable memory B or T lymphocyte formation. Thus, vaccine formulations which include most (>95%) of oral subunit protein vaccines must have a strategy to overcome oral tolerance. In the absence of such a strategy, it is highly unlikely that most subunit protein will function as a useful vaccine when given orally. One means of having a subunit vaccine given orally inducing long term immunity is by the concurrent administration of an adjuvant.

The ability of oral vaccine formulations to induce mucosal and systemic memory responses depends upon the expansion of memory T and B lymphocytes at mucosal and at systemic sites. Therefore, the goal of an effective mucosal immune response is not solely the formation of mucosal IgA, but includes the formation of memory T helper lymphocytes and the formation of memory T cytotoxic lymphocytes at mucosal and systemic sites. Failure to recognize this fact limits the scope of vaccine development when designing oral vaccine formulations.

BRIEF SUMMARY OF THE INVENTION

The present invention relates transgenic soybeans, to vaccines and to the use of transgenic soybeans for the incorporation of immunogens that can be used as vaccines. Accordingly, this invention, in one embodiment, relates to producing edible subunit vaccines for oral immunization to individuals. Individuals refer to all animals or any of a plurality of animals, including but not limited to humans, livestock, laboratory animals, pets, and wild animals.

In another embodiment of the present invention, induction of tolerance in individuals (for example, children) using transgenic soybeans is contemplated (and fits within the scope of the instant invention) as a viable method for prophylactically or therapeutically treating the development or ongoing nature of potentially life threatening allergic reactions.

Thus, the present invention relates to preventing allergy before an individual develops such allergy (i.e., prophylactic treatment) and also relates to including treatment of individuals who have already developed allergic disease (i.e., therapeutic treatment) using edible transgenic soybeans. Presently some individuals go through "desensitization injections", and there are many disadvantages which are overcome by the present invention.

Prophylactic oral allergen therapy to prevent the development of hypersensitivity in individuals who have not yet shown clinical symptoms is a novel idea. In an embodiment of the present invention, prophylactic oral allergen therapy is disclosed wherein the allergens are expressed in transgenic soybeans. The advantages of prophylactic oral allergen therapy as disclosed in the instant invention include:

1) High levels of allergen can be expressed in a stable form in transgenic soybeans for pennies a dose. The soybean protein content is considerably higher than that of any other transgenic plants, such as tomatoes, potatoes, tobacco, carrot, apple, rice, corn, berries such as strawberries and raspberries, banana, etc. Therefore, the cost of numerous exposures to any oral toleragen is significantly reduced from known vaccine technology, and the efficacy is significantly superior to using any other transgenic plant system. Further, many of these transgenic systems require processing conditions (e.g., cooking a potato or pasteurizing a tomato to make tomato juice) that will likely destroy the antigenic protein. Many of these plants have other inherent disadvantages (such as the relative acidity of tomatoes and the inedibility of tobacco) that make them less suitable for use as edible vaccines.

2) Soy protein and soy milk formulations for human consumption are safe and are easily made. In fact, soy milk formulations are so safe that they are routinely fed to infants with little or no side effects. Such safety further supports the notion that widespread therapy with allergen-containing soy formulations would not pose any significant risk, even to those individuals who might never develop hypersensitivity to that particular allergen. With the ability to process soy into a desired formulation, one can also control the dosage of protein that appears in that desired formulation. Similarly, one can adjust dosages dependent upon how the soy is processed into powder, protein and/or soymilk (or mixtures thereof). The different way of processing the soybean to acquire a desired dosage is an advantage that simply does not exist with other transgenic plants such as potatoes or tomatoes. Soymilk is a particularly attractive vehicle for administering desired dosages as soymilk can be produced in large quantities, and then a correct dosage for a given "lot" of soymilk can be determined and administered to an individual.

3) The instant invention can be used with any of a number of antigens to induce tolerance to a variety of antigens following their oral administration. Thus, this invention also can be used to induce oral tolerance to allergens in children, with an example being certain food allergies.

4) Transgenic soybean is remarkably stable over long periods of time and the proteins that are expressed in soybean are shown in the present invention to have stability for periods of up to two years or longer. Thus, transgenic soybean is an ideal way to store and/or stockpile vaccines without the need for refrigeration. This storage capacity of soybeans makes soybean particular attractive in third world locations where refrigeration may be a problem. The transgenic soybean storage ability also has potential uses in the bio-terrorism area. When the above alluded to storage capacity of soybeans is combined with the high protein concentrations in soybeans, one is left with a unique formulation that will not require concentration of protein (and thus, not require refrigeration in processing. Other transgenic plants lack this combination of features and are thus, are inferior to soybeans in possible vaccine and/or toleragen use.

Soybeans also provide the following advantages relative to other transgenic plants.

A) Antigen dosage levels required to induce mucosal memory T and B lymphocyte responses in individuals can be obtained using transgenic soybeans or their formulations, but cannot be obtained using other transgenic plants (e.g., potatoes). This is because individuals cannot practically be expected to consume enough transgenic potato to induce memory mucosal T and B lymphocytes without extensive purification or concentration of the antigen made in these transgenic potatoes.

B) The ability to store antigens indefinitely without refrigeration in transgenic soybean seeds prior to their use in vaccine formulations is a unique physical property of this plant, but not of other transgenic plants. For example, fruits or vegetables cannot be stored for any length of time even under refrigeration without significant spoilage. Accordingly, other transgenic plants suffer from a loss of usefulness as oral vaccines.

C) The integrity of antigens expressed in transgenic soybeans is maintained even following their formulation for consumption into soy protein powder and soy milk. This is not the case for edible formulations of other plants following their formulation. For example, it is unreasonable to expect that formulation of transgenic tomatoes into tomato juice (i.e. pasteurization) and the resulting low pH of such canned juice would be an environment conducive for maintenance of the integrity of most subunit protein antigens.

The present invention has not only the advantages discussed above but also has the following additional uses disclosed below.

One such use of transgenic soybeans is the induction of tolerance in individuals as a method for prophylactically or therapeutically treating the development or further exacerbation of autoimmune diseases. The present invention is directed to preventing the development of autoimmunity before an individual develops such diseases (i.e., prophylactic treatment). Moreover, the present invention also includes treatment of individuals who have already developed autoimmune disease (i.e., therapeutic treatment).

In another embodiment, the present invention relates to the use of transgenic soybeans for the incorporation of mucosal protein adjuvants that can be used in oral vaccine formulations. Accordingly, this invention, in one embodiment, relates to producing edible adjuvants for use in vaccine formulations for the purpose of orally immunizing individuals. Individuals refer to all animals or any of a plurality of animals, including but not limited to humans, livestock, laboratory animals, pets, and wild animals.

An advantage of the present invention is that it is not necessary to purify allergens, autoimmune antigens, or subunit protein antigens from transgenic soybeans. However, it is contemplated and within the scope of the invention that partial purification may occur, such as a purification that may generate soy powder or soy milk formulations from such plants. Known techniques can be used to concentrate and/or purify desired protein.

It is contemplated, within the scope of the instant invention, and shown in the disclosure that follows that non-purified transgenic soybeans induce an immunological response in mice. Thus, the non-purified soybeans and any formulations that are isolated from these transgenic soybeans can be used to induce tolerance when given orally to young mice. This supports the notion that widespread consumption of soy formulations containing allergens or autoimmune self antigens to induce systemic tolerance is a viable therapy for children or young adults which would prevent (or significantly limit) the development of immediate type hypersensitivity reactions and autoimmunity later in life.

Further, soybeans have protein amounts that are on the order of 38% protein—Thus, the present invention generally has protein amounts that are equal to or above 15%, more preferably 20% and even more preferably 30%.

When soybeans are mentioned in the present invention, it is meant all parts of the soybeans including, but not limited to, the seeds, the leaves, and other parts of the soybean including but not limited to any of the internal parts of the soybean plant (such as chloroplasts, endoplasmic reticulum, cytosol, vacuoles, and/or other organelles and the like).

BRIEF DESCRIPTION OF THE SEVERAL
VIEWS OF THE DRAWING

FIG. 1 shows the nucleotide comparison of the native and synthetic versions of fanC. Numbering begins with the start of transcription. Synthetic fanC lacks 63 nucleotides at the 5' terminus, which encode a leader sequence in the native version (shown in bold type). The synthetic version encodes a peptide of 160 amino acids with a predicted mobility of 18 kDa. The native and synthetic sequences share 75.1% homology at the nucleotide level and are identical at the amino acid level with the exception of the leader sequence deletion and insertion of an N-terminal methionine residue for translation initiation. The unique NheI restriction site in the synthetic sequence is underlined FIG. 2 shows the Design of synthetic fanC plant expression vectors. The plasmids pKP3 and pKP5 represent intermediate cloning vectors; pKP7 is the final plant transformation vector used for soybean transformation. Elements are labeled as follows: synfanC, synthetic fanC; P-35S, cauliflower mosaic virus (CaMV) 35S constitutive promoter; TEV, tobacco Etch Virus leader sequence; T-35S, 35S viral terminator element; P-nos and T-nos, *Agrobacterium tumefaciens* nopaline synthase promoter and terminator elements, respectively; Bar, bialophos herbicide resistance gene; RB and LB, *A. tumefaciens* T-DNA right and left border repeats; Spc, spectinomicin antibiotic resistance gene.

Figure 3:
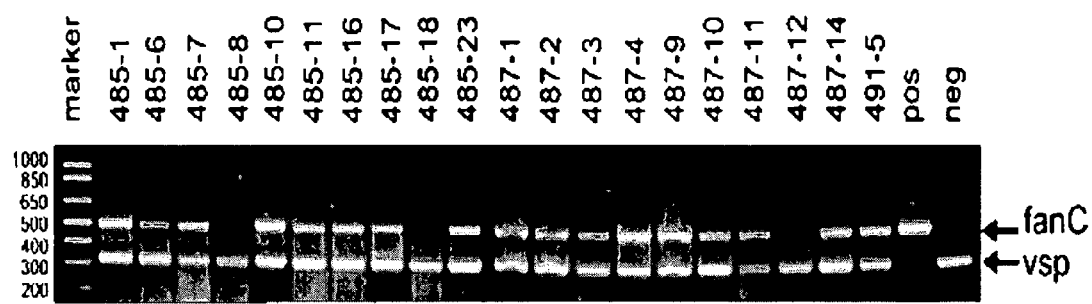

FIG. 3 shows the identification of fanC transgenic lines. $T_0$ genomic DNA was isolated from leaf tissue and used in duplex PCR. fanC primers spanning the translational start and stop sites were chosen to ensure intactness of the fanC ORF (Open Reading Frame), while primers amplifying an internal segment of the vegetative storage protein (vsp) gene served as an internal control. Amplification of intact transgenic fanC and the internal vsp fragment results in products of ~500 bp and ~325 bp, respectively. Positive (pos) and negative (neg) controls were pKP7 plasmid DNA and non-transformed soybean genomic DNA, respectively. The sizes of a molecular weight standard are shown in base pairs on the left side (marker).

FIG. 4 shows Expression of synthetic FanC in transgenic soybean. A. Western blot showing immunological detection of synthetic FanC. Protein was isolated from leaves of transgenic and control plants. 12 µg protein was loaded in each lane. Rabbit serum containing polyclonal antibodies raised against bacterially-expressed K99 (primary antibody) and HRP-conjugated goat anti-rabbit Ig (secondary antibody) were used for immunodetection. Protein isolated from a bacterially-expressed FanC fusion protein (rFanC) and from non-transformed (NT) control plants served as positive and negative controls, respectively. The predicted mobilities for transgenic FanC and rFanC are ~18 kDa and ~60 kDa, respectively. The sizes of molecular weight standards are shown as kDa. B. Western blot used for quantification of FanC. 10 ng and 30 ng of rFanC protein was loaded as a standard. 1 µg and 3 µg of leaf-extracted protein was loaded for comparison to the standard.

FIG. 5 shows FanC protein accumulation in $T_1$ progeny of lines 485-1 and 485-10. The Western blot shows immunological detection of synthetic FanC in $T_0$ parents and $T_1$ progeny. 3 µg of total protein from the indicated plants were loaded in each lane.

Figure 6:
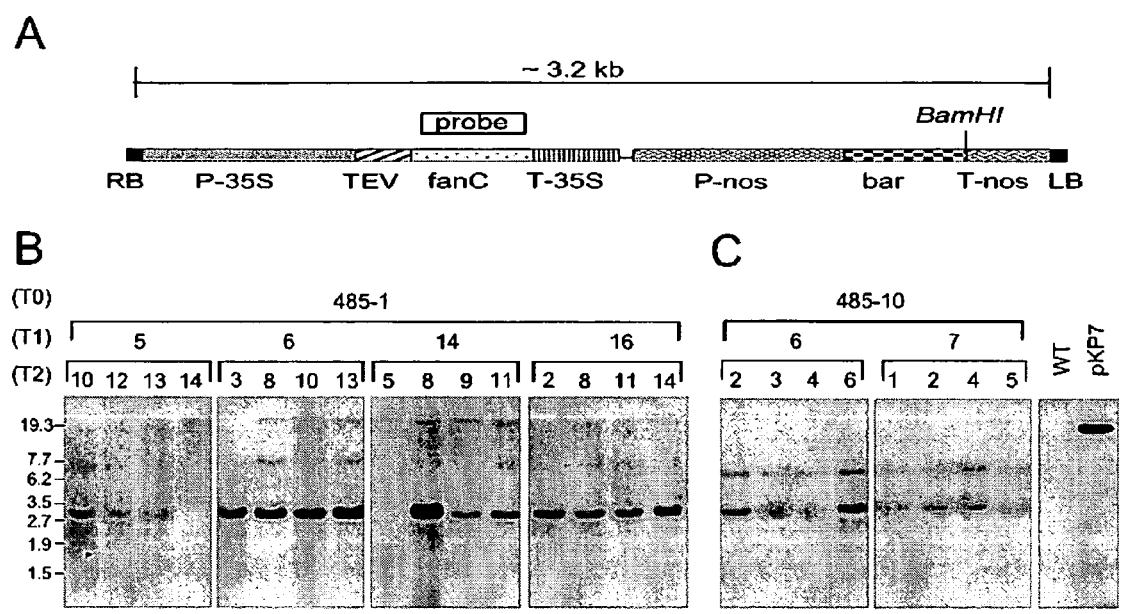

FIG. 6 shows Southern analysis of $T_2$ progeny from lines 485-1 and 485-10. A. Schematic diagram of the T-DNA region from pKP7. The locations of the BanHI restriction site and fanC probe are shown. The entire length of the T-DNA between the borders is ~3.2 kb. B. Southern gel of $T_2$ progeny derived from line 485-1. Genomic DNA was digested with BamHI, and membranes were probed with a 32P-labeled fanC probe. The sizes of molecular weight standards are shown in kb. C. Southern gel of $T_2$ progeny derived from line 485-10. Positive and negative controls were BamHI-digested pKP7 DNA and BamHI-digested genomic DNA isolated from untransformed (WT) plants, respectively.

FIG. 7 shows Immunohistochemical detection of FanC. FIGS. 7A, B. 10 µm cross sections of paraffin-embedded transgenic leaf tissue (Figure A) and control leaf tissue (Figure B) were processed and incubated with rabbit serum containing anti-K99 antibodies followed by an Alexafluor 594 goat anti-rabbit IgG secondary antibody. Samples were viewed at 20× magnification using confocal microscopy. Identical parameters on the microscope were used for photography of both tissue samples. FIGS. 7C and D show 10 µm cross sections of paraffin-embedded transgenic leaf tissue (Figure C) and control leaf tissue (Figure D) were processed and incubated with hematoxylin and eosin stains. Samples were viewed at 20× magnification using a light microscope.

Figure 8:
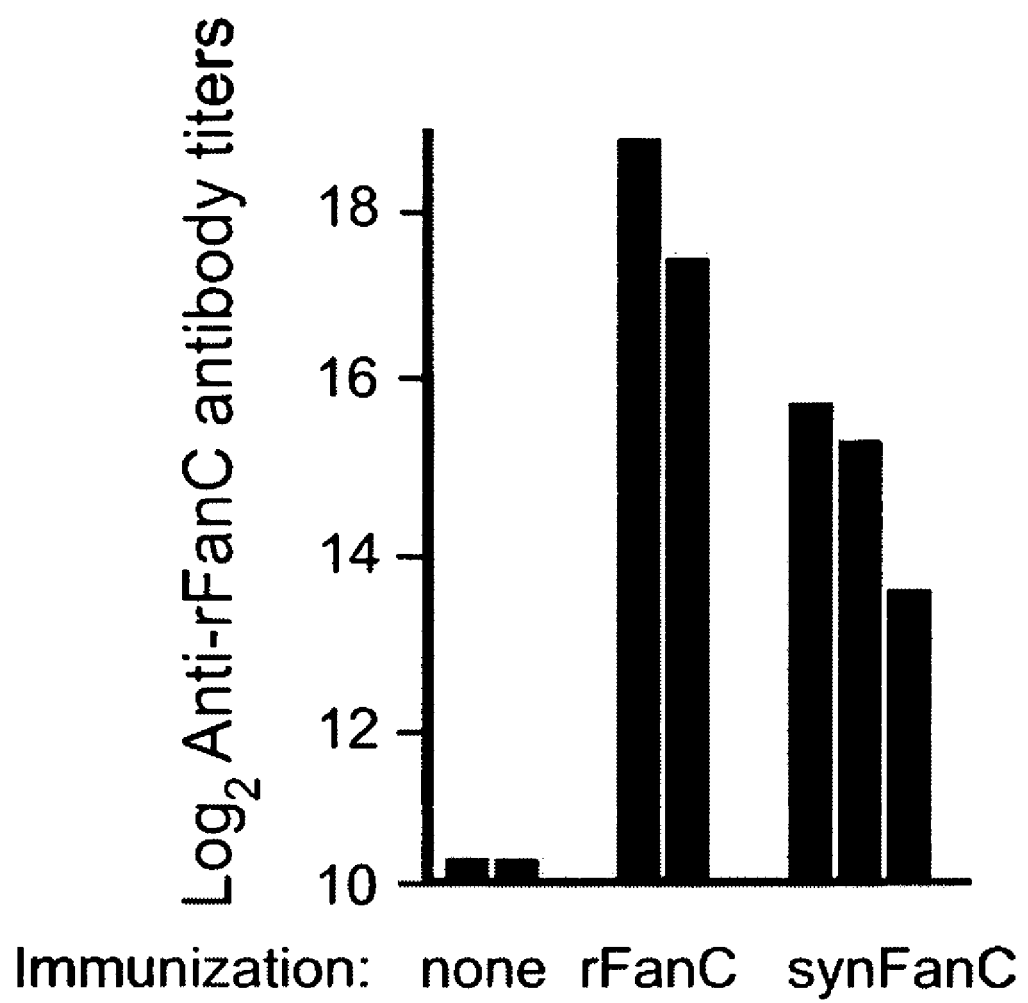

FIG. 8 shows Antibody titers in mice immunized with soybean-derived FanC. Groups of mice were untreated (none), immunized with recombinant FanC fusion protein (rFanC), or immunized with protein lysates derived from soybean expressing synthetic FanC (synFanC). Serum was taken from mice 21 days following immunization, and an ELISA was used to detect the presence of antibodies against bacterially-derived rFanC. Results are shown as antibody titers from individual mice immunized as indicated.

Figure 9:
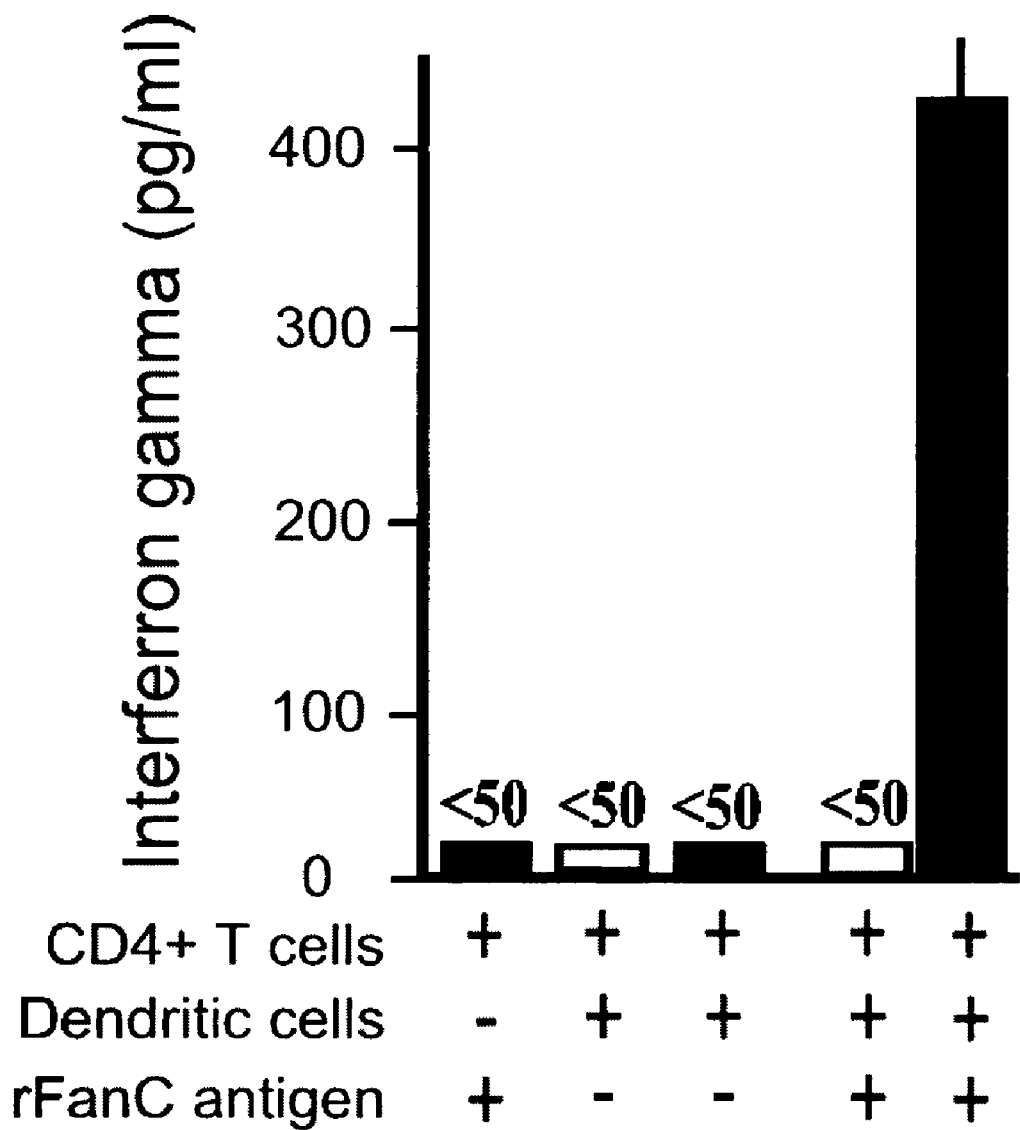

FIG. 9 shows FanC-specific CD4+ T lymphocyte responses in immunized mice. Groups of mice were untreated (white columns) or immunized with protein lysates derived from soybean expressing synthetic FanC (black columns). CD4+ splenic leukocytes were isolated from these mice and cultured in the presence (+) or absence (−) of dendritic cells pulsed with bacterially-derived FanC (rFanC). Four days following culture, supernates were taken, and the amount of secreted interferon gamma was quantified using an ELISA. Results are presented as means of triplicate determinations (+standard deviation) from three different mice.

Figure 10:
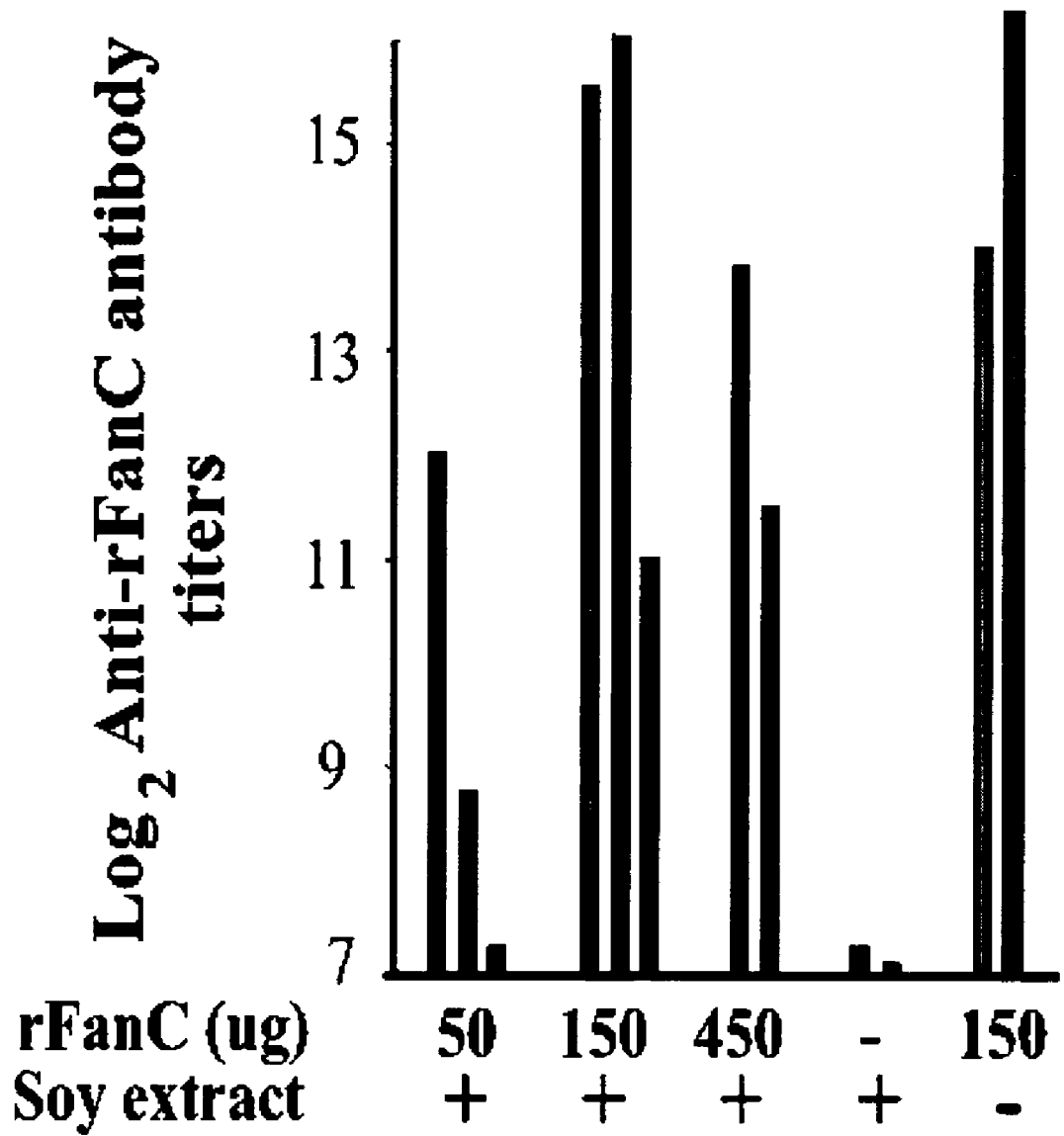

FIG. 10 shows antibody titers in mice immunized with rFanC plus soybean extract. Groups of mice were immunized by oral gavage with (+) or without (−) 10 mg of soybean protein containing the indicated amount of rFanC antigen. A booster dose was given on days 21 and 35, and serum was collected on day 53. An ELISA was used to detect the presence of antibodies against rFanC. Results are shown as antibody titers from individual mice. Titers were defined as the highest dilution of sera that had an absorbance value twice that of background. Animals immunized with soy extract alone and rFanC alone served as controls.

Figure 11:
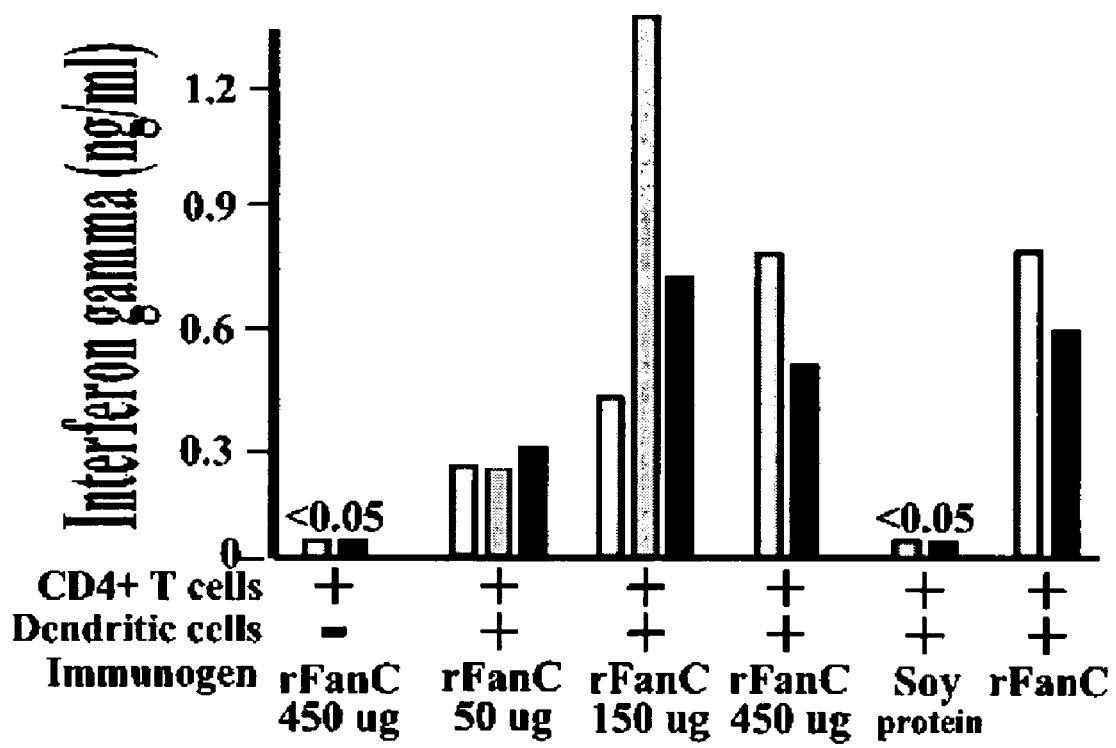

FIG. 11 shows FanC-specific CD4+ T lymphocyte responses in immunized mice. The immunization of mice was described in FIG. 10 above. CD4+ splenic leukocytes were isolated from mice and cultured in the presence(+) or absence (−) of dendritic cells pulsed with rFanC. Four days following culture, supernates were taken, and the CD4+ T cells amount of secreted interferon gamma was quantified using an ELISA.

Figure 12:
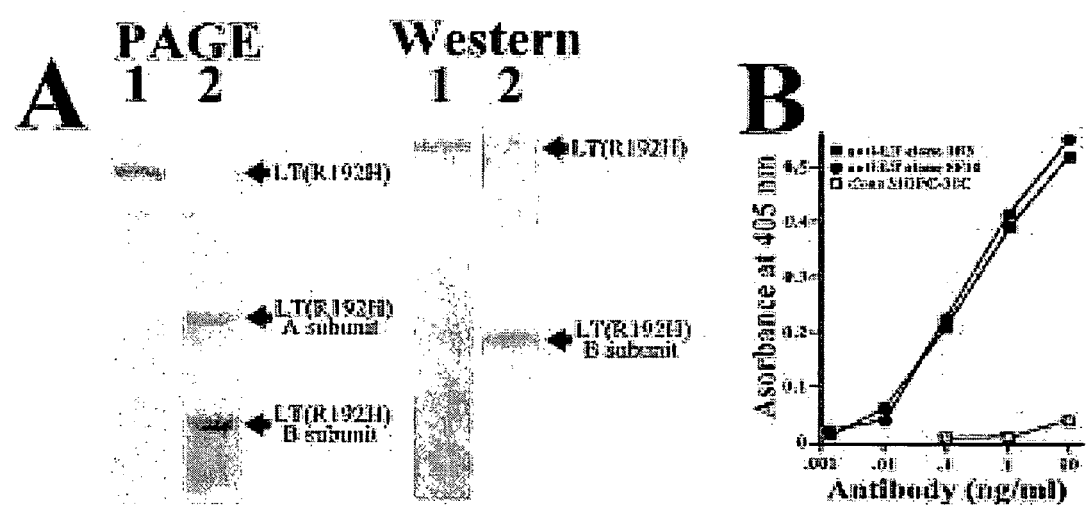

FIGS. 12A-B show purified LT(R192H), which was characterized by electrophoresis on polyacrylamide gels and by western blot analyses. FIG. 12A shows the characterization of both recombinant LT(R192H) and monoclonal antibodies produced against LT. Several of the cloned and expanded monoclonal antibodies were assayed for their ability to recognize LT(R192H) using Western blot analyses and using ELISAs. Together these results demonstrate the specificity of these antibodies and demonstrate that at least one of the monoclonal antibodies was directed against the B subunit of LT.

FIG. 13 shows the Nucleotide sequence of SEB. The locations of the two amino acid mutations to relinquish SEB nontoxic are shown as bold and underlined nucleotides. The SEB sequence can be back translated using soybean codon usage, and all regulatory sequences such as mRNA processing, polyadenylation, secondary structures, etc. can be eliminated. The plant-optimized SEB sequence can be cloned as an expression cassette that targets SEB protein accumulation to the endoplasmic reticulum, or to other subcellular locations. A seed specific promoter such as soybean 7S can be used to target SEB accumulation to seeds. (See Caiyin et al., Cloning and functional analysis of soybean seed-specific promoter, bases 1 to 666 directly Submitted on 23 Apr. 2004 to the Microbiology Department, Life Science Institution of Nankai University, 94 Weijin Road, Tianjin 300071, China, the sequence is hereby incorporated by reference in its entirety). The SEB expression cassette can be cloned into a binary vector containing an expression cassette for selection such as the bar gene driven by nopaline synthase elements to create a plant transformation vector that can be used in *Agrobacterium*-transformation of soybean.

Figure 14:
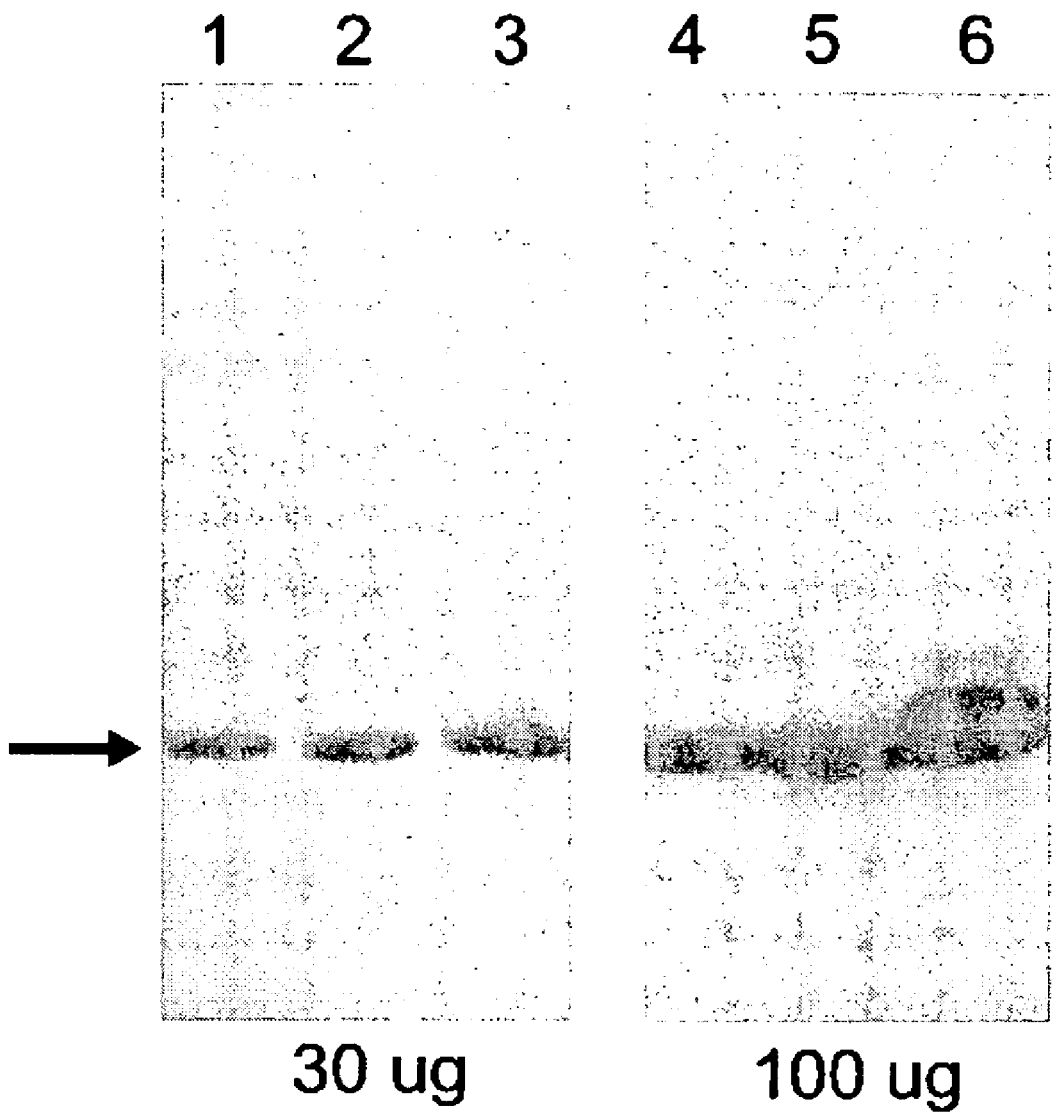

FIG. 14 shows antigen stability in 18 month old stored seeds used to make different formulations that could be applied to commercial scale-up. The stability of transgenic FanC following long term storage and formulation into soy protein and soymilk formulations is shown. T1 transgenic seeds (line 485-10) were stored for 18 months, and then used in various different formulations. The first formulation served as a control, and seeds were extracted with buffer as previously described (Piller, et. al 2005) (Lanes 1 and 4). In the second formulation, seeds were treated with hexane, ethanol, and heat, analogous to commercial methods for making soy flour and soy flakes. For this formulation, seeds were dehulled and ground to a fine powder. The powder was extracted with 10 parts of warm hexane, and then washed in 100% ethanol and heated to 90° C. for 10 minutes. Proteins were then extracted from the protein-enriched soy powder for use in Western analysis (Lanes 2 and 5). In the third formulation, soymilk was extracted as would be accomplished using either commercial or personal soymilk makers such as the SoyQuick Soymilk Maker (Kitchen's Best Manufacturing Group, Ltd.) or the Hurricane Soymilk Maker (Internet Kits, Inc.). Soymilk was subjected to boiling at 100° C. for 10 minutes and clarified prior to use in the Western analysis (Lanes 3 and 6). Protein from the preparations was quantified, and either 30 micrograms or 100 micrograms of protein was subjected to Western blot analysis using a polyclonal anti-FanC antibody to determine whether intact FanC was detectable. The arrow indicates the expected molecular weight for FanC, as estimated from molecular weight standards and a histidine-tagged recombinant FanC run on the same gel. Protein in lanes 1 (30 µg) and 4 (100 µg) was derived from the non-processed control. Protein in lanes 2 (30 µg) and 4 (100 µg) was derived from soy protein powder formulations. Protein in lanes 3 (30 µg) and 6 (100 µg) was derived from soymilk formulations. Surprisingly, processing of soybean seed into soy-enriched powder or soymilk did not appear to significantly impact the stability of the FanC antigen.

Figure 15:
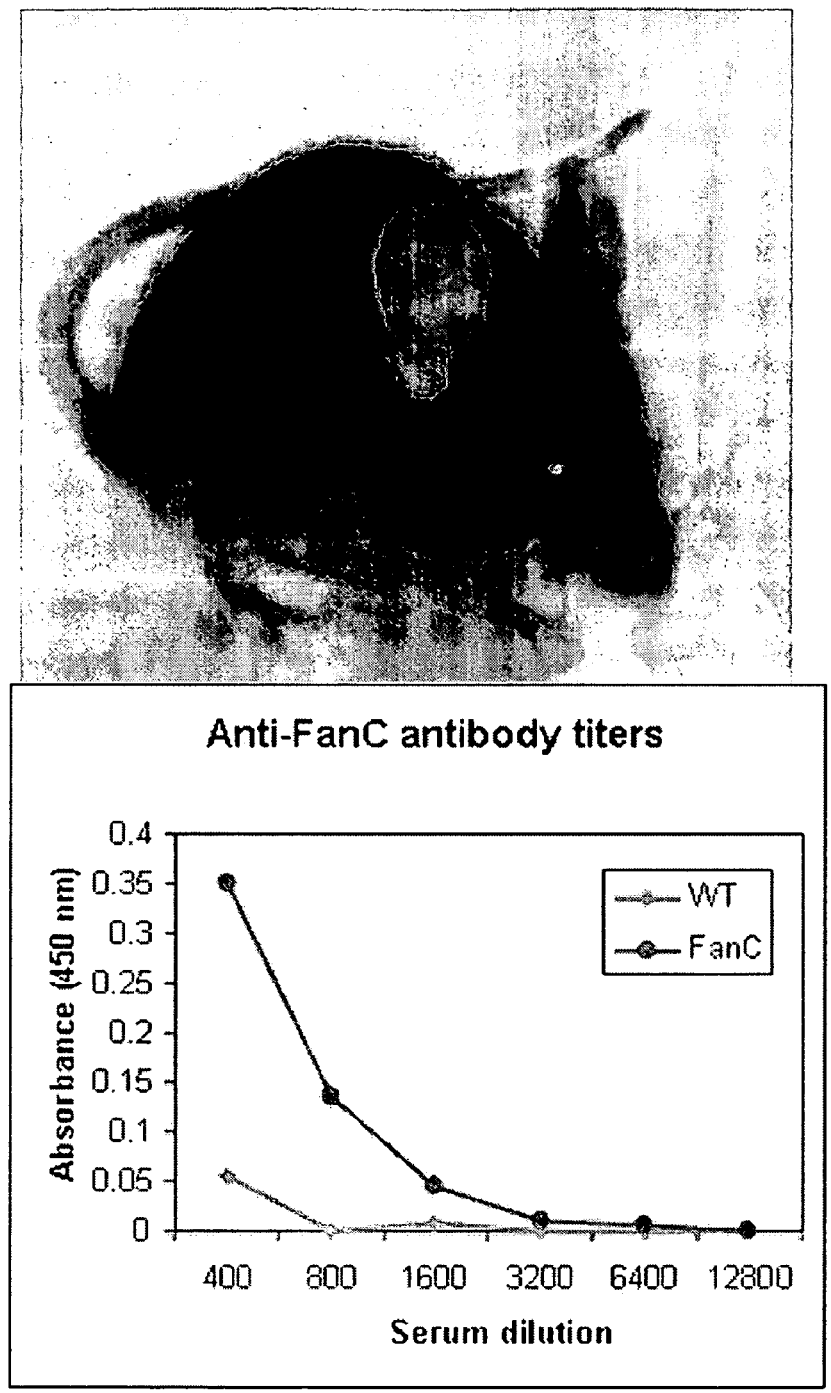

FIG. 15 shows a mouse consuming a soybean seed in FIG. 15A, but more importantly in panel FIG. 15B shows the anti FanC antibody titer following oral immunization of such mice.

Figure 16:
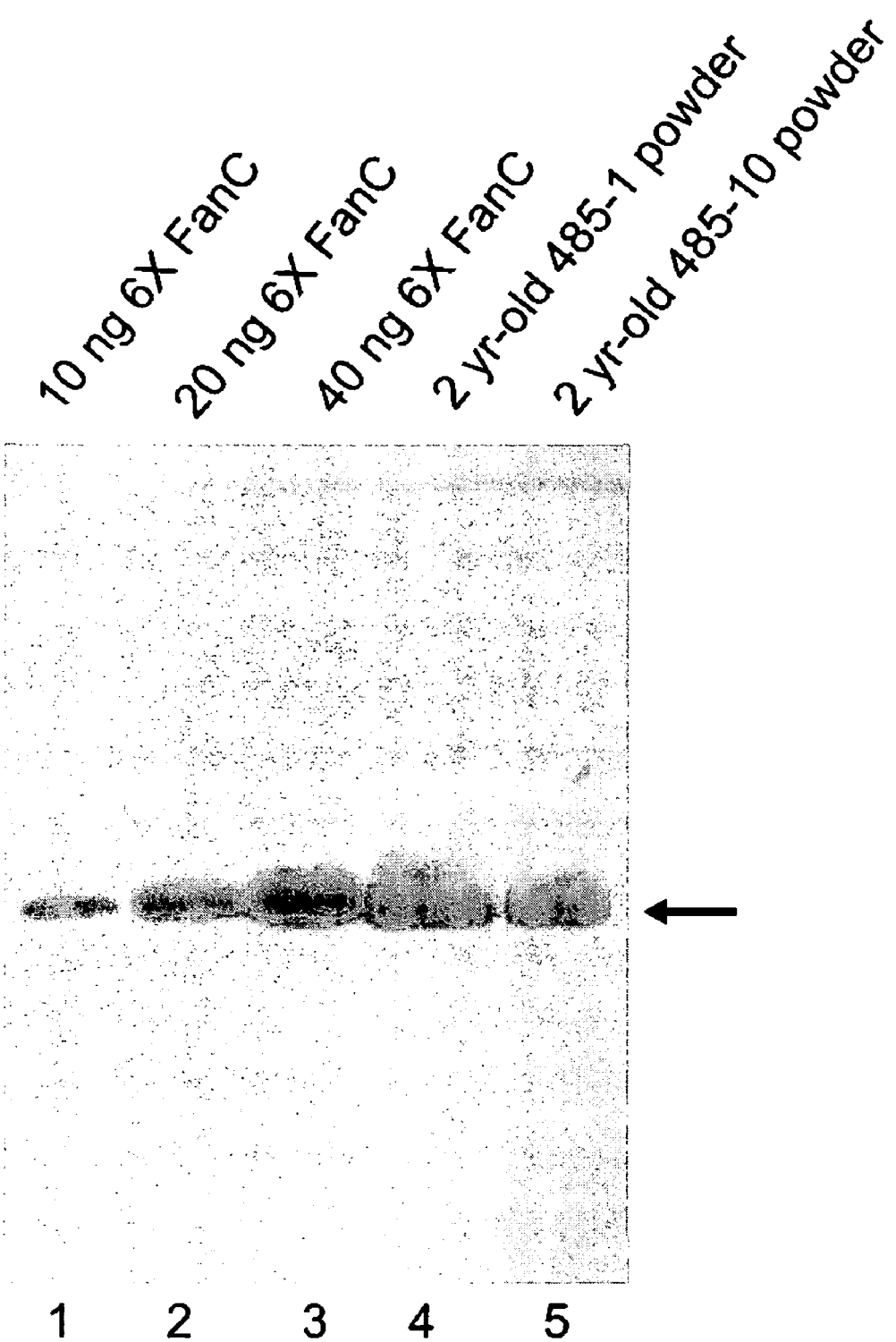

FIG. 16 shows the stability of FanC antigen in dried soybean leaves stored for 2 years at room temperature. To transgenic leaves from lines 485-1 and 485-10 were air dried, ground to a powder, and stored in a 50 ml conical tube at room temperature on a laboratory shelf for 24 months. After 24 months, protein was extracted from the dried leaf material and quantified using the Bradford protein assay. Fifteen micrograms of protein from each line was then subjected to SDS-PAGE and Western analysis, as previously described (Piller et al 2005). Known concentrations of recombinant histidine tagged FanC (6×FanC) were included as a standard. This result clearly shows that the FanC antigen can be stored for prolonged periods of time in a stable form in dried leaves.

Figure 17:
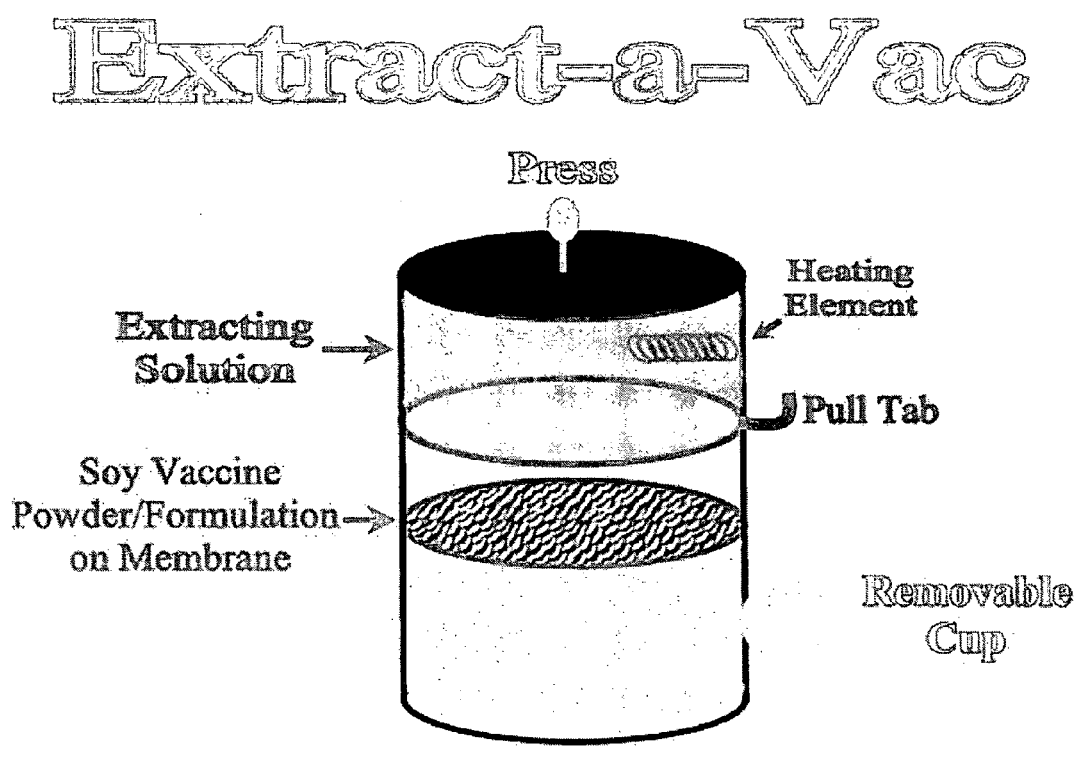

FIG. 17 shows the extract-a-vac for extracting the protein of interest from soybeans.

Figure 18:
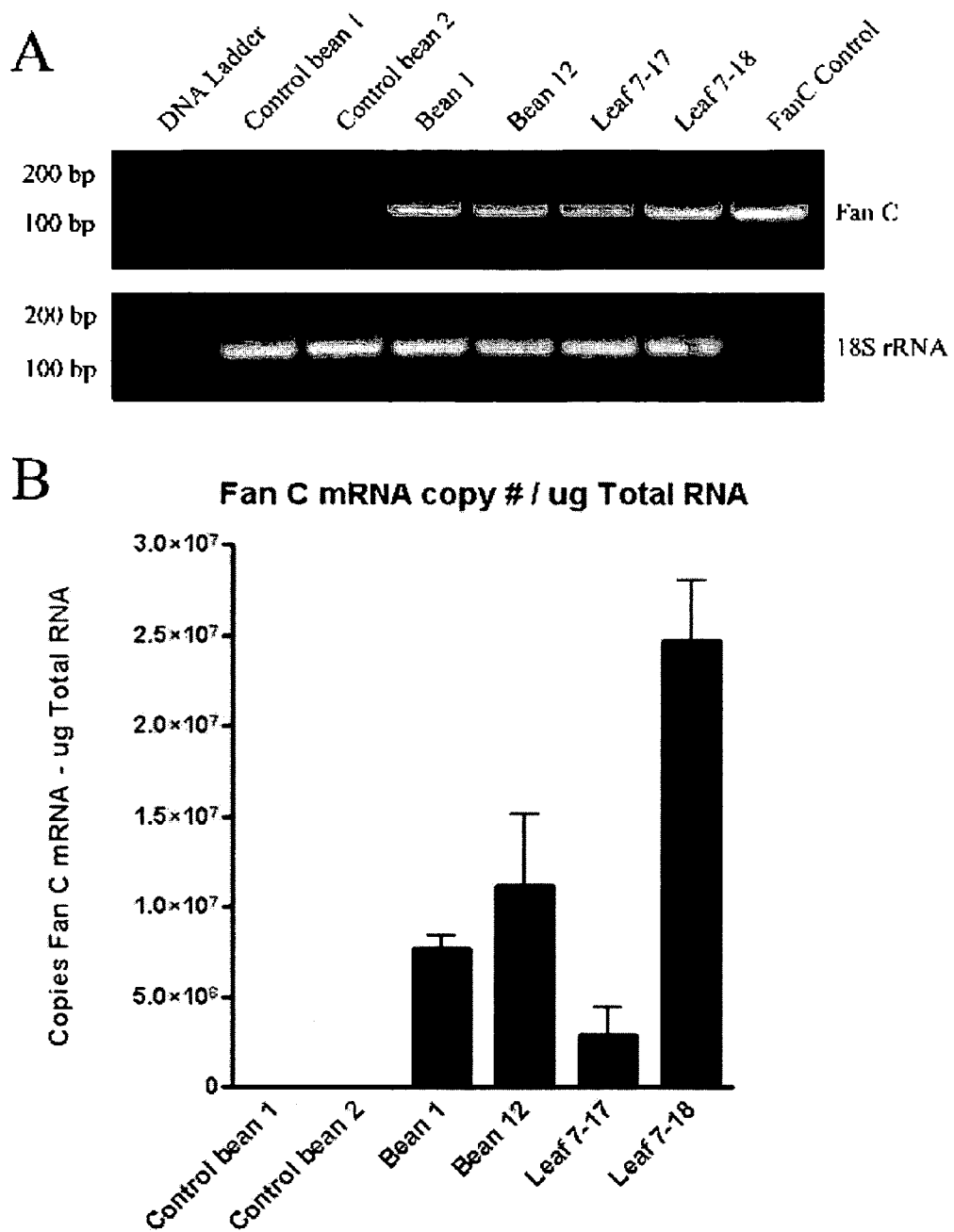

FIG. 18 shows expression of synthetic Fan C mRNA in soybeans. (Panel A) Semi-quantitative RT-PCR analysis of mRNA expression in soybean seeds and leaves. Expression of the mRNA encoding synthetic Fan C and for comparison, soybean 18S rRNA, is shown for control and transformed seeds and leaves. RT-PCR was performed using total RNA and the results presented as amplified products electrophoresed on ethidium bromide stained agarose gels. DNA sizes in basepairs are shown to the left of the DNA standard. For a control, 1 ng of plasmid containing the synthetic Fan C gene was used as the template for the PCR reaction. (Panel B) Synthetic Fan C mRNA copy number derived from quantitative real time reverse transcriptase PCR (RT-PCR). Expression of the mRNA encoding synthetic Fan C was assayed by real time PCR. Fan C mRNA copy number is presented per µg of total RNA, derived from seeds (Control bean 1 and 2 are wild type seeds; Bean 1 and 12 are $T_3$ seeds derived from line 485-10) of leaves (leaf 7-17 and 7-18 are $T_2$ leaves derived from line 485-10).

Figure 19:
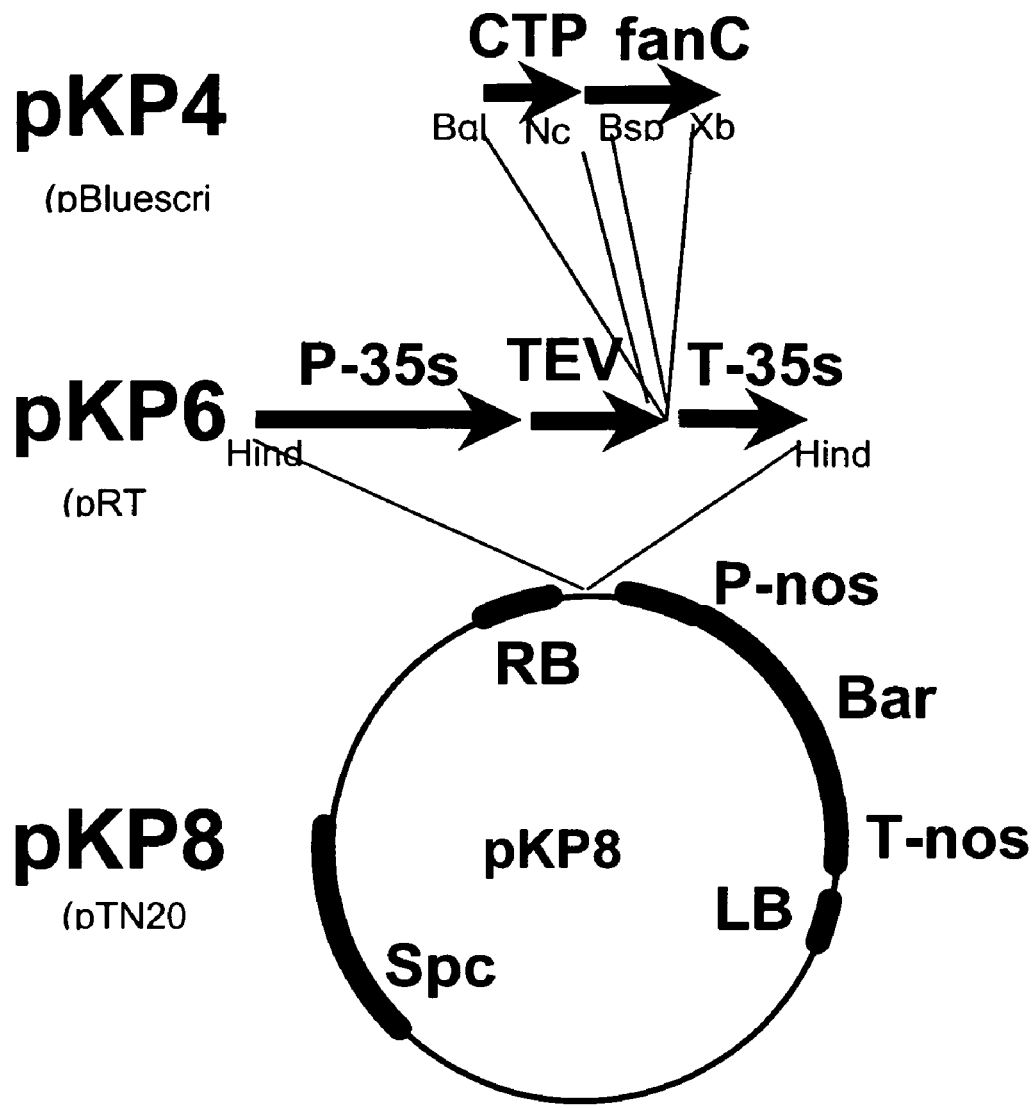

FIG. 19 shows construction of pKP8 for targeting synthetic FanC to the chloroplast. Synthetic fanC optimized for expression in soybean was isolated from pKP3 following digestion with BspHI plus XbaI, and the pea chloroplast transit peptide (CTP) sequence was isolated following digestion with BglII plus NcoI. The CTP and fanC were cloned in tandem in pBLuescript to generate pKP4. The expression cassette targeting fanC to the chloroplast was isolated from pKP4 following digestion with HindIII and subcloned into pTN200 to generate pKP8. pKP8 was used to transform Glycine max.

Figure 20:
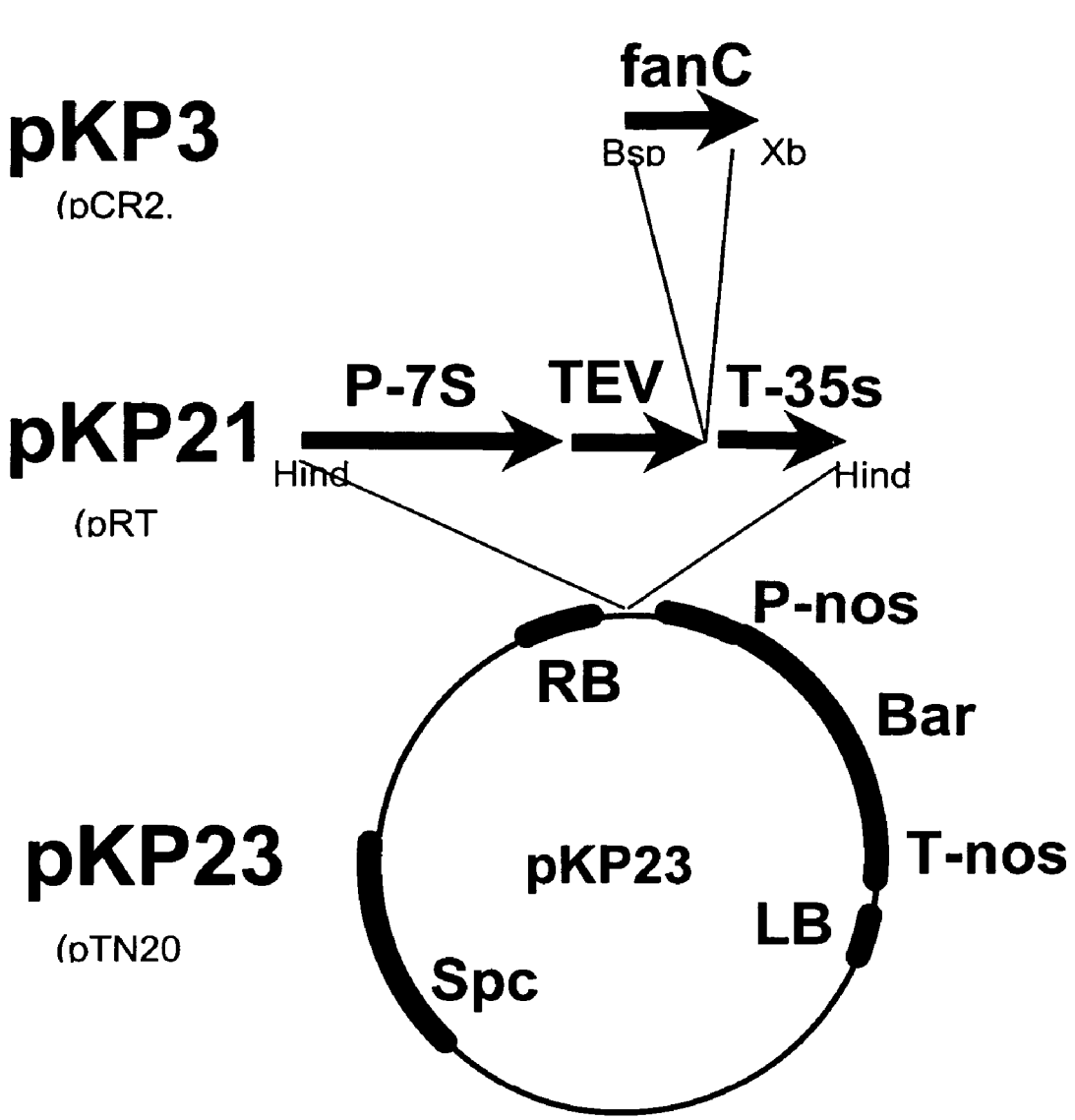

FIG. 20 shows construction of pKP23 for targeting synthetic FanC to soybean seeds. Synthetic fanC optimized for expression in soybean was isolated from pKP3 following digestion with BspHI plus XbaI, and subcloned into pRTL linearized with NcoI plus XbI to generate pKP21. The fanC expression cassette of pKP21 contains the soybean beta conglycinin promoter driving expression of synthetic fanC. A leader sequence from tobacco etch virus was included as an enhancer. The fanC expression cassette was isolated from pKP21 following digestion with HindIII and subcloned into pTN200 to create pKP23. pKP23 can be used to transform Glycine max.

Figure 21:
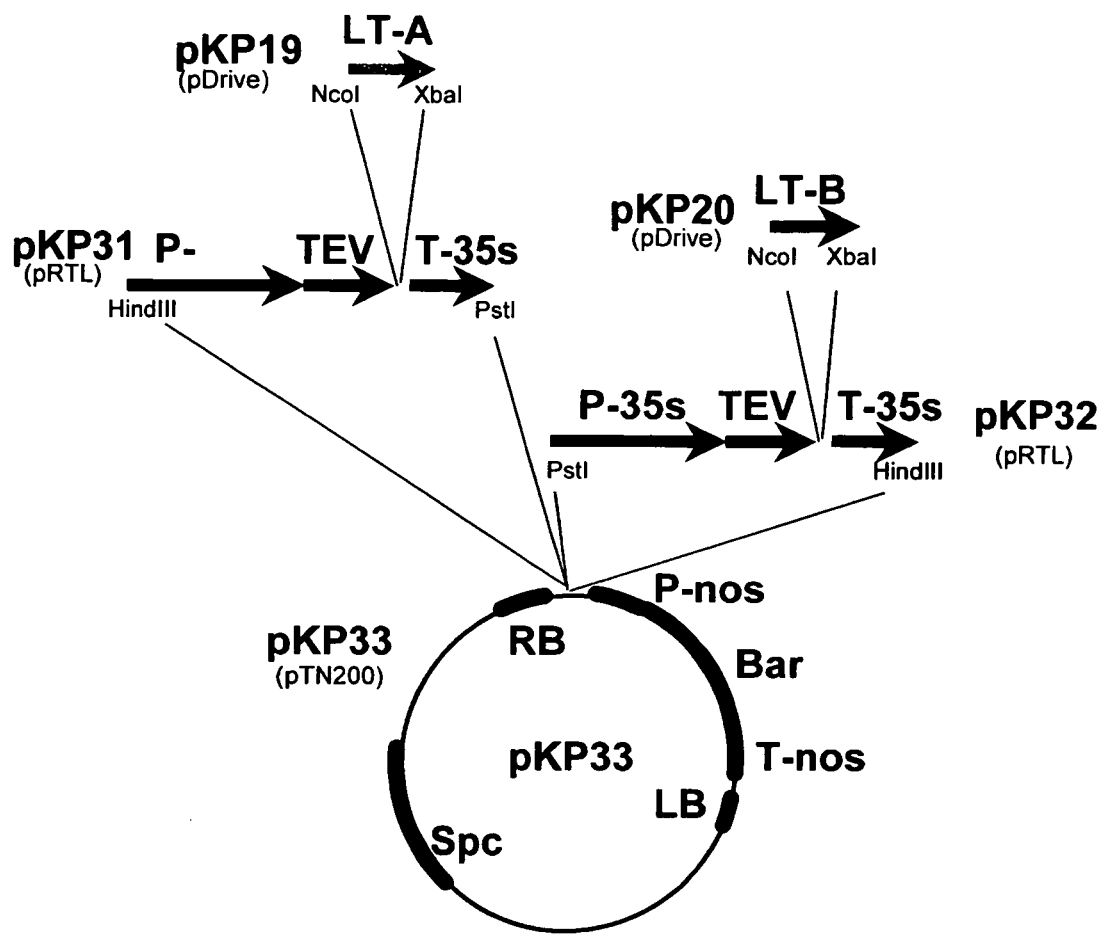

FIG. 21 shows construction of pKP33 for expressing synthetic LT-A, synthetic LT-B, and nontoxic LT in soybeans. Synthetic LT-A and LT-B optimized for expression in soybean were subcloned into the pDrive vector backbone creating pKP19 and pKP20, respectively. Synthetic LT-A and LT-B were isolated from pKP19 and pKP20 following digestion with NcoI plus XbaI, and subcloned into pRTL to generate pKP31 and pKP32, respectively. The LT-A expression cassette was isolated from pKP31 following digestion with HindIII plus PstI, while the LT-B expression cassette was isolated from pKP32 following digestion with PstI plus HindIII. The isolated LT-A and LT-B expression cassettes were ligated into the HindIII site of pTN200 to create pKP33. pKP33 contains the LT-A and LT-B expression cassettes in tandem, and adjacent to a third expression cassette (Bar) used for selection. pKP33 was transformed into Glycine max, and plants are currently regenerating in the greenhouse. Because of the constitutive nature of the 35S promoter, it is expected that transgenic LT, as well as the individual A and B subunits, should accumulate in tissues throughout the plant, including leaves and seeds.

Figure 22:
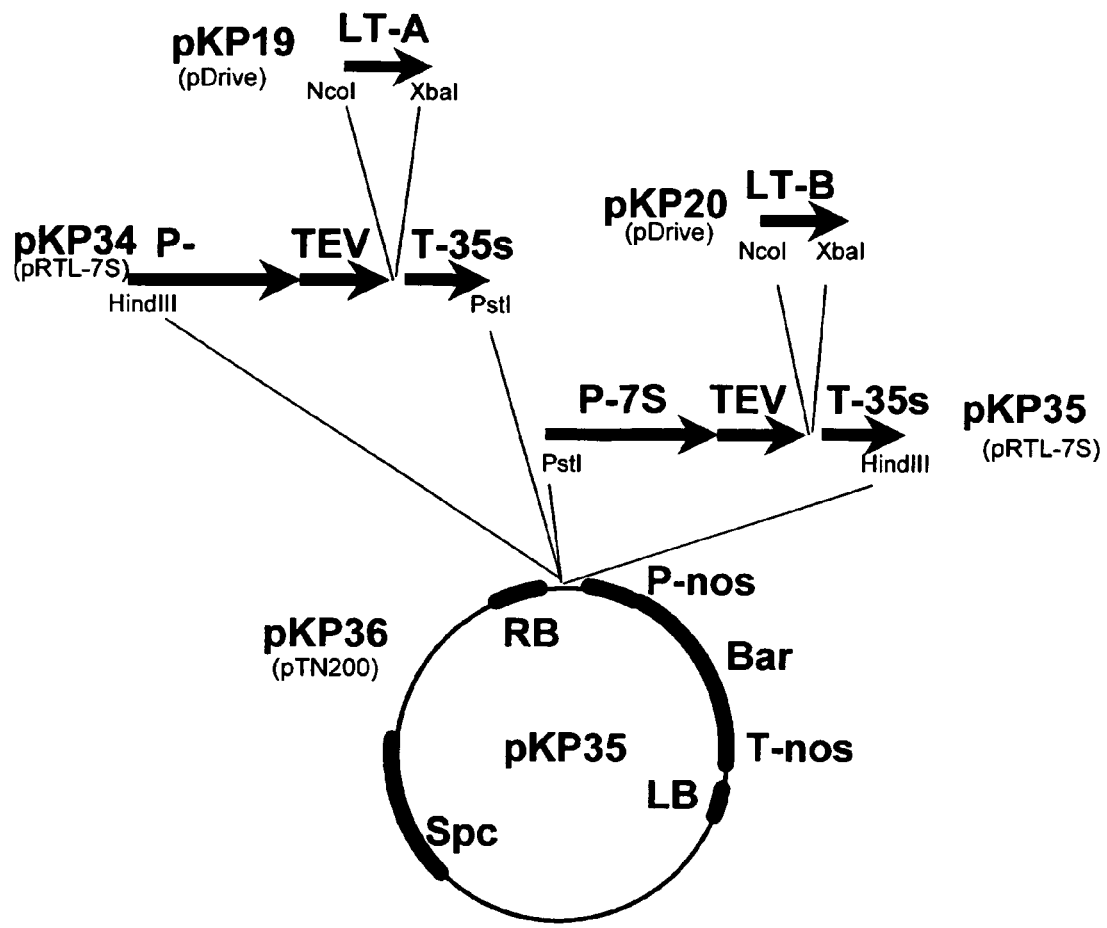

FIG. 22 shows construction of pKP35 for expressing synthetic LT-A, synthetic LT-B, and nontoxic LT in soybean seeds. Synthetic LT-A and LT-B optimized for expression in soybean were isolated from pKP19 and pKP20 following digestion with NcoI plus XbaI, and subcloned into pRTL-7S containing the 7S seed specific promoter to generate pKP34 and pKP35, respectively. The LT-A expression cassette was isolated from pKP34 following digestion with HindIII plus PstI, while the LT-B expression cassette was isolated from pKP35 following digestion with PstI plus HindIII. The isolated LT-A and LT-B expression cassettes were ligated into the HindIII site of pTN200 to create pKP35. pKP35 can be used to transform Glycine max. Because of the nature of the soybean beta conglycinin 7S promoter, it is expected that transgenic LT as well as the individual A and B subunits should accumulate in the seed.

Figure 23:
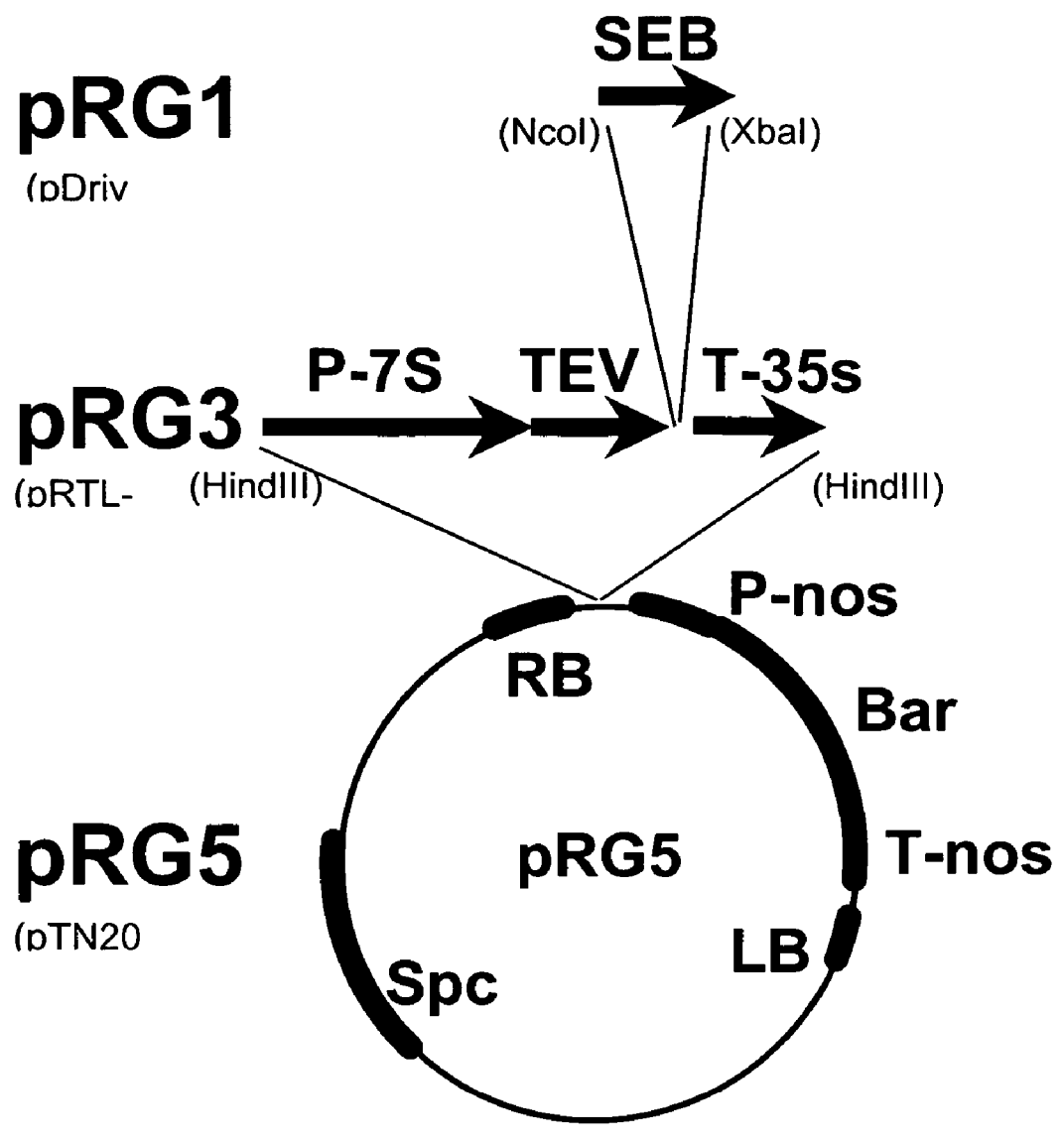

FIG. 23. Construction of pRG5 for targeting synthetic nontoxic staphylococcus enterotoxin B (SEB) soybean seeds. Synthetic SEB optimized for expression in soybean was isolated from pRG1 following digestion with NcoI plus XbaI, and subcloned into pRTL-7S to generate pRG3. The SEB expression cassette of pRG3 contains the soybean beta conglycinin promoter to drive expression and accumulation of transgenic SEB in seeds. A leader sequence from tobacco etch virus was included as an enhancer. The SEB expression cassette was isolated from pRG3 following digestion with HindIII, and subcloned into pTN200 to create pKP23. pKP23 can be used to transform Glycine max.

Figure 24:
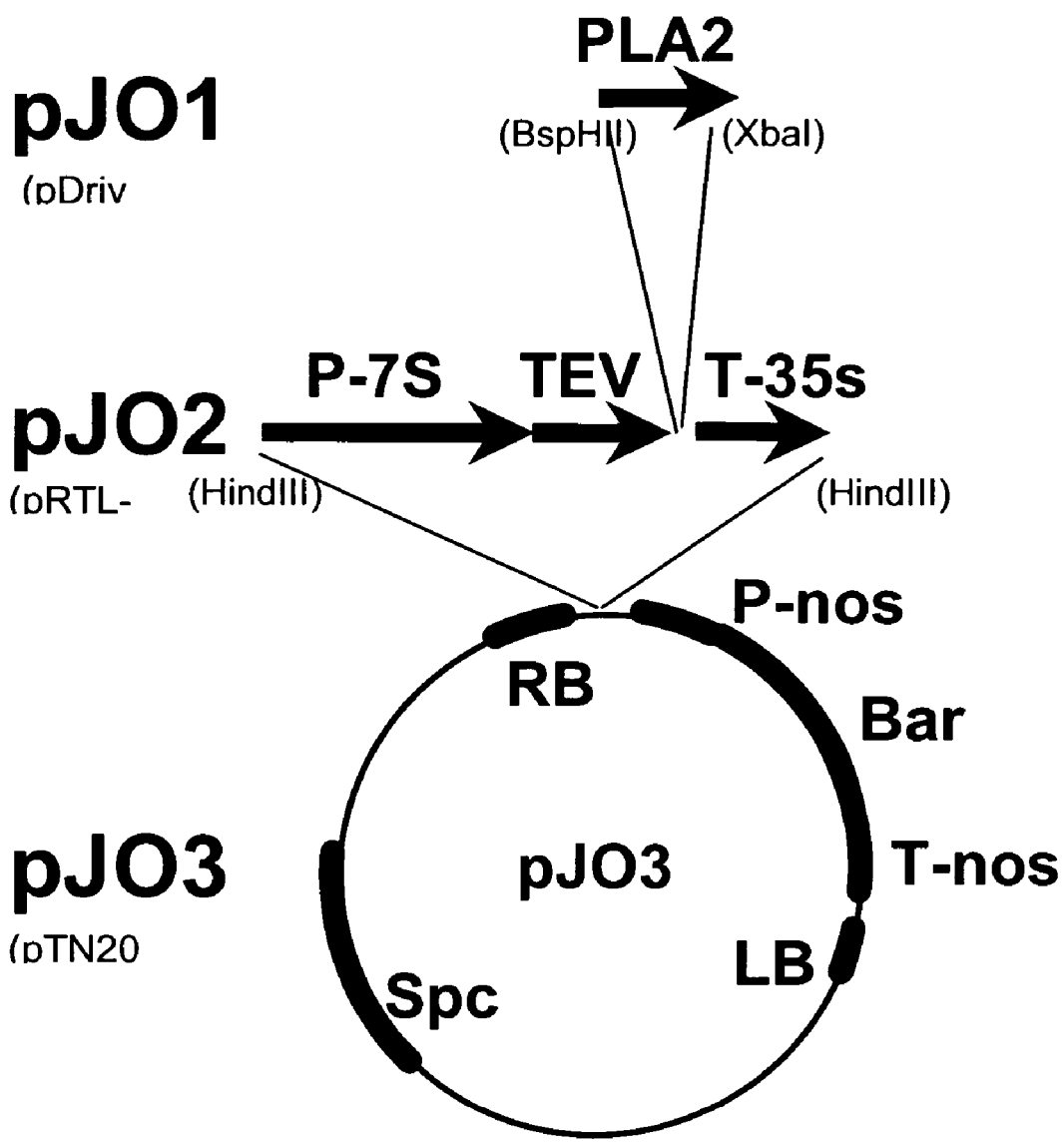

FIG. 24 shows construction of pJO3 for targeting synthetic phospholipase A2 (PLA2) to soybean seeds. Synthetic PLA2 optimized for expression in soybean was isolated from pJO1 following digestion with BspHI plus XbaI, and subcloned into pRTL-7S to generate pJO2. The PLA2 expression cassette of pJO2 contains the soybean beta conglycinin promoter to drive expression and accumulation of transgenic PLA2 in seeds. A leader sequence from tobacco etch virus was included as an enhancer. The PLA2 expression cassette was isolated from pJO2 following digestion with HindIII, and subcloned into pTN200 to create pJO3. pJO3 can be used to transform Glycine max.

FIGS. 25A-I show primers used in the present invention as well as the wild-type and mutant sequences that were used in the present invention. The synthetic sequences shown are optimized for expression in the soybean system. There are four proteins shown: $E.\ coli$ K99 FanC, $E.\ coli$ LT subunits A and B (LT-A and LT-B, expressed in the same plant), Staphylococcus enterotoxin B (SEB), and Aphis mellifera phospholipase A2 (PLA2); the first three are subunit vaccine candidates while PLA2 is a toleragen. Targeting each of these four candidates to the seed is within the scope of the present invention or alternatively, accumulating protein to the cytosol, chloroplast, and endoplasmic reticulum are also within the scope of the present invention.

The figures in this application have been derived from synthetic FanC targeted to the cytosol. Because of the constitutive nature of the promoter used in this construct, transgenic FanC also fortuitously expresses and accumulates in seeds. A construct targeting FanC to the chloroplast has also been made. Constructs targeting FanC and/or any other antigen in transgenic soybeans directed specifically to the seed (using a seed promoter) and the endoplasmic reticulum (using targeting and retention signals) are also within the scope of the present invention. It is also contemplated and within the scope of the invention that any other cellular organelle can be targeted such as the chloroplast, vacuole, mitochondria or any other plant organelle.

Synthetic constructs LT-A and LT-B that have been targeted to the cytosol are shown in FIGS. 25E-F. Soybean plants containing these synthetic nucleotide sequences have been transformed, and grown.

FIG. 25D shows the nucleotide sequence of synthetic SEB which has been targeted to the seed.

FIG. 26 shows the identification of transgenic lines expressing FanC in the chloroplast. Panel A. T1 genomic DNA was isolated from leaf tissue of the indicated lines and used in duplex PCR. Amplification of intact transgenic fanC and the internal vsp fragment control results in products of ~500 bp and ~325 bp, respectively. Positive (pos) and negative (neg) controls were pKP8 plasmid DNA and non-transformed soybean genomic DNA, respectively. The sizes of a molecular weight standard are shown in base pairs on the left side. Panel B shows expression of chloroplast-targeted synthetic FanC in soybean as detected by a Western blot. Protein was isolated from leaves of transgenic soybean transformed with pKP8, and control plants. 50 μg protein was loaded in each lane. Rabbit serum containing polyclonal antibodies raised against bacterially-expressed K99 (primary antibody) and HRP-conjugated goat anti-rabbit Ig (secondary antibody) were used for immunodetection. The predicted mobility of FanC is ~18.5 kDa. The sizes of molecular weight standards are shown as kDa on the left side.

FIGS. 27A-B show FanC protein accumulation in $T_1$ seeds of lines 485-1 and 485-10. Eight $T_1$ seeds from the indicated lines were pulverized, and genomic DNA and protein were extracted for use in PCR and Western assays. Panel a shows a duplex PCR assay used to identify transgenic seeds. The arrows indicate the expected positions of the fanC product (~500 bp) and vsp internal control (~325 bp). Panel b shows a Western blot in which 15 μg seed protein were loaded onto a 10% SDS-PAGE gel, followed by immunnodetection using anti-K99 antibodies. The arrow indicates the expected position (~18.5 kDa) of FanC. Collectively, these results show 35S-driven FanC accumulation in transgenic soybean seeds.

DETAILED DESCRIPTION OF THE INVENTION

Recombinant techniques using expression cassettes have allowed the incorporation of exogenous genes (as well as endogenous genes) into other organisms. Expression cassettes generally contain a number of regulatory elements. The construction of the expression cassette of the instant invention contains one or more of the following regulatory elements: 1) a promoter to initiate transcription, 2) an enhancer region to enhance transcription and/or translation, dependent upon the promoter used, 3) sequences to target transcription, translation, and/or protein accumulation to specific locations within the plant or cell, 4) a coding region, which determines the specific protein or proteins that will be expressed in transgenic plants, and 5) a polyadenylation recognition site to determine transcription termination and for mRNA stability. In addition, 6) a selectable marker cassette can be included for selection during transformation and in subsequent generations.

The promoter of the instant invention directs transcription and/or directs protein accumulation in the seed component of the plant. However, it should be understood that protein accumulation can be directed to other parts of the soybean. Seed-specific promoters are available and are known to those of skill in the art. In an exemplary embodiment, beta conglycinin is used as a promoter, which is sometimes referred to as the 7S promoter. The 7S promoter has been used to drive expression of synthetic fanC, synthetic SEB, and synthetic bee venom PLA2. Although the 7S promoter was used in the embodiments of the instant invention, it should be understood that other promoters can be used with the ideal promoter being one which results in the highest accumulation of transgenic protein in the desired region of the soybean (for example in the seed) as determined by assays such as Western analysis, ELISA, or direct plant part (e.g., seed) composition assays. Another embodiment contemplates the used of constitutive promoters, such as 35S. Any of a plurality of constitutive promoters can be used depending on where one wants to drive the accumulation of protein. For example, 35 S drives the accumulation of transgenic protein in soybean seeds and leaves.

An example of a subunit antigen expressed in seed driven by the 35S promoter is synthetic fanC. Other antigens that can be driven by the 35S promoter include wild-type and synthetic LT-A and Lt-B, wild-type and synthetic SEB, and wild-type and synthetic PLA2. A plurality of other subunit antigen species genes that cause known diseases can be incorporated into exogenous systems (such as higher plant systems like soybeans and the like) and driven by the 35S promoter or any of a plurality of promoters. Examples of the diseases (and their associated proteins) include hepatitis A (capsid protein and a non-structural protein), AIDS (gp 120 & gp41 Gag & RT), SARS (Spike glycoprotein nucleocapsid), Genital Herpes (gB and gD scaffolding proteins), Smallpox (membrane protein and core proteins), Encephalitis (nsProtein 1-4 spike proteins) and the like.

It is also contemplated that any of a plurality of enhancers can be used in the present invention. An exemplary embodiment of an enhancer is the tobacco etch virus leader sequence (TEV), which enhances translation. Any of a plurality of enhancers can be used for a plurality of constructs, such as the constructs for synthetic fanC, synthetic LT-A and Lt-B, synthetic SEB, and synthetic PLA2.

The present invention also contemplates the use of targeting sequences. Targeting sequences are used to direct MRNA and/or protein to various cellular locations. The reason for doing this would be to increase/optimize protein accumulation and or to optimize immunogenicity of a particular antigen or allergen in a particular region. It is possible that a protein targeted to one compartment may accumulate to higher levels than the same protein targeted to another location within the cell. It is also possible that proteins targeted to different locations may have different immunogenicities, possibly due to post translational modifications such as phosphorylation, glycosylation, etc. Targeting sequences may be located 5', 3' and/or 5' and 3' to the gene of interest (GOI). Examples of how different areas can be targeted using different targeting sequences are shown in Table 1 (the synFanC gene is discussed in more detail below).

TABLE 1

Components of the FanC expression cassettes.

| Target location | Promoter | Translational enhancer | N-terminal sequence | Gene | C-terminal sequence | Terminator |
|---|---|---|---|---|---|---|
| Cytosol | CaMV-35S | TEV | — | synFanC | — | CaMV-35S |
| Endo. Ret. | CaMV-35S | TEV | soy vspαS | synFanC | KDEL | CaMV-35S |
| Chloroplast | CaMV-35S | TEV | pea rbc-S | synFanC | — | CaMV-35S |
| Seed | Soy 7S | TEV | — | synFanC | — | CaMV-35S |

Abbreviations for Table 1: CaMV-35S, cauliflower mosaic virus 35S (promoter and polyadenylation/terminator); TEV, tobacco etch virus leader sequence; synFanC, plant-optimized version of FanC; soy vspαS, 21 amino acid leader sequence ofthe αS subunit of soybean vegetative storage protein; KDEL, universal endoplasmic reticulum retention signal; pea rbc-S, 84 amino acid targeting peptide of pea ribulose 1,5 bis-phosphate carboxylase small subunit; soy 7S, soybean beta-conglycinin 7S promoter.

An example of a sequence targeted to the endoplasmic reticulum would contain the alpha subunit of soybean vegetative storage protein located 5' to the coding region, along with an in-frame 3' retention signal such as one coding for the amino acids KDEL, (SEQ ID NO. 54), HDEL (SEQ ID NO. 55), or RDEL (SEQ ID NO. 56). An example of a sequence used to target a protein to the chloroplast would be the small subunit of the protein Rubisco derived from Pisum sativum (pea), fused in frame and at the amino terminus of the gene of interest. Thus, the instant invention contemplates the use of any of a plurality of targeting sequences based upon where the GOI is to be accumulated.

The coding region is the nucleotide sequence that when expressed, generates a desired protein. Essentially any soybean gene segment(s) designed to encode a single protein, or part of a protein, multiple proteins, multiple parts of a single protein, or multiple parts of multiple proteins optimized for expression in soybean are contemplated and within the scope of the invention. Modifications from the native gene are also contemplated and are within the scope of the present invention. Examples of modifications or segment would include the following:

- Alteration of the codon usage to employ preferred codon usage in Glycine max (soybean)
- Alteration of the GC content of the segment to represent similarity to GC content of soybean coding genes
- Removal of any AT stretches longer than 5 nucleotides to reduce the potential for cryptic polyadenylation and MRNA instability
- Removal of any MRNA processing signals, including splice site recognition and AT content of introns that may destabilize mRNAs Removal of secondary structures, hairpin loops, etc. that may destabilize mRNA Addition of sequences to direct mRNA or subsequent pre-proteins to desired locations within cells or plant structures (such as seeds, chloroplasts, mitochondria, cytosol, endoplasmic reticulum, etc.).

In an embodiment of the present invention, a synthetic sequence is optimized for expression in soybean and subcloned in the context of other regulatory elements to allow expression and accumulation in soybean. Examples of segments that have been constructed with these criteria for transformation and expression in soybean include synthetic fanC, synthetic SEB (*Staph* enterotoxin B), and synthetic bee venom phospholipase A2 (PLA2). It is also contemplated and within the scope of the present invention to have multiple protein segments. Although any of a plurality of multiple protein segments are contemplated, an exemplary embodiment of multiple protein segments expressed simultaneously in soybean include synthetic *E. coli* heat labile toxin subunit A and subunit B (LT-A and LT-B). Another example of multiple segments from multiple proteins may include immunogenic domains from several of the known allergens in bee venom.

An embodiment of the present invention may also include terminators and/or polyadenylation sequences. These elements provide stability. Exemplary embodiments that can be used in the system of the instant invention include the CaMV 35S polyadenylation sequence, and the Nopaline Synthase polyadenylation sequence. Other terminators and/or polyadenylation sequences are known and are considered to be within the scope of the present invention.

Multiple expression cassettes can be introduced into soybean. However, when one limits the number of redundant sequences, expression tends to proceed more efficiently. Multiple expression cassettes may include for example, the use of different promoters, enhancers, targeting signals, and terminator/polyadenylation elements. Moreover, any antigen or toleragen cassette can be stacked with other cassettes to employ beneficial effects to the seeds, such as increased linolenic acid, herbicide tolerance, pesticide tolerance, drought resistance, stress resistance, etc.

The expression of subunit vaccines in soybeans has significant advantages over previously reported strategies. Due to the relatively high protein content of soybeans when compared to other transgenic plants that have been used for the development of edible vaccines (e.g. potatoes and tomatoes), the soybean system permits the highest expression of immunogen per total weight of plant material. Furthermore, the ease of efficiently converting soybeans into formulations which can be consumed is a significant advantage in developing oral immunization strategies. Accordingly, the use of transgenic soybeans as one of the methods of choice for expression of plant-derived vaccines should be apparent to those of skill in the art when read in light of the instant disclosure.

Mice were allowed to eat whole soybeans coupled with an oral adjuvant. The mice were exposed several times, and serum antibody titers were determined about one month later. Mice fed whole soybeans expressing FanC developed high antibody titers when compared to controls. The results of this study provide compelling evidence to support the practicality of expressing edible vaccines in soybeans.

Thus, any of the plurality of above described regulatory elements can be incorporated or omitted from the expression cassettes. Specific examples of how the expression cassettes can be manipulated to generate transgenic organisms to develop oral vaccines are given below. However, first a general overview of the invention is given, then several examples of an overall strategy (using specific examples) are given that describes how one might develop a strategy for oral vaccines.

Subunit Vaccines Containing a Single Protein

Essentially any protein which is contained within a single open reading frame can be expressed in soybeans for use as a vaccine once a synthetic, plant-compatible gene is made and transformation is performed. An example showing *E. coli* FanC for use as a vaccine in livestock is described below. Another example is SEB.

It is contemplated and within the scope of the present invention that modifications of the original protein sequence may be made. These modifications include:

a) amino acid changes at specific residues in the original protein sequence which might change the stability of the protein, change the immunogenicity of the protein, change the solubility of the protein, change the glycosylation of the protein, or change the phosphorylation of the protein.

b) conserved amino acid changes at specific residues in the original protein sequence to construct similar, but distinct proteins (e.g. a change from glutamic acid to aspartic acid).

c) non-conserved amino acid changes at specific residues in the original protein sequence to construct similar, but distinct proteins (e.g. a change from glutamic acid to glutamine).

d) addition of amino acids at the N-terminus or C-terminus to target proteins to specific cellular locations (for example, chloroplast, endoplasmic reticulum, seed, mitochondria, etc.).

Subunit Vaccines Containing Multiple Proteins

Essentially any protein which is contained within two or more open reading frames can be expressed in soybeans for use as a vaccine once synthetic, plant-compatible genes are made and transformation is performed. However, there are some additional considerations, including the use of the same or different regulatory elements for each of the proteins to be expressed.

As discussed above in the section pertaining to subunit vaccines containing a single protein, modifications of the original protein sequence are considered to be within the scope of the invention and include:

a) amino acid changes at specific residues in the original protein sequence which might change the stability of the protein, change the immunogenicity of the protein, change the solubility of the protein, change the glycosylation of the protein, or change the phosphorylation of the protein.

b) conserved amino acid changes at specific residues in the original protein sequence to construct similar, but distinct proteins (e.g. a change from glutamic acid to aspartic acid).

c) non-conserved amino acid changes at specific residues in the original protein sequence to construct similar, but distinct proteins (e.g. a change from glutamic acid to glutamine).

d) addition of amino acids at the N-terminus or C-terminus to target proteins to specific cellular locations (for example, chloroplast, endoplasmic reticulum, seed, mitochondria, etc.).

Subunit Toleragens (i.e. Allergens or Autoimmune Antigens) Containing a Single Protein Essentially any protein which is contained within a single open reading frame can be expressed in soybeans for use as a toleragen once a synthetic, plant-compatible gene is made and transformation is performed.

An example of one of these toleragens, bee venom phospholipase A2 for use in humans is given in detail below. Another example would be grass pollen.

As discussed above in the section pertaining to subunit vaccines containing a single protein and multiple proteins, modifications of the original protein sequence are considered to be within the scope of the invention and include:

a) amino acid changes at specific residues in the original protein sequence which might change the stability of the protein, change the immunogenicity of the protein, change the solubility of the protein, change the glycosylation of the protein, or change the phosphorylation of the protein.

b) conserved amino acid changes at specific residues in the original protein sequence to construct similar, but distinct proteins (e.g. a change from glutamic acid to aspartic acid).

c) non-conserved amino acid changes at specific residues in the original protein sequence to construct similar, but distinct proteins (e.g. a change from glutamic acid to glutamine).

d) addition of amino acids at the N-terminus or C-terminus to target proteins to specific cellular locations (for example, chloroplast, endoplasmic reticulum, seed, mitochondria, etc.).

Subunit Toleragens (i.e. Allergens or Autoimmune Antigens Containing Multiple Proteins)

Essentially any protein which is contained within two or more open reading frames can be expressed in soybeans for use as a toleragen once synthetic, plant-compatible genes are made and transformation is performed. However, there are additional considerations, including the use of the same or different regulatory elements for each of the proteins to be expressed.

As discussed above in the section pertaining to subunit vaccines containing a single protein subunit toleragens, modifications of the original protein sequence are considered to be within the scope of the invention and include:

a) amino acid changes at specific residues in the original protein sequence which might change the stability of the protein, change the immunogenicity of the protein, change the solubility of the protein, change the glycosylation of the protein, or change the phosphorylation of the protein.

b) conserved amino acid changes at specific residues in the original protein sequence to construct similar, but distinct proteins (e.g. a change from glutamic acid to aspartic acid).

c) non-conserved amino acid changes at specific residues in the original protein sequence to construct similar, but distinct proteins (e.g. a change from glutamic acid to glutamine).

Subunit Vaccines or Toleragens Containing a Peptide Segment, or Concatemers of Homologous Peptide Segments, or Concatemers of Heterologous Peptide Segments Representing B Lymphocyte Epitopes The subunit vaccines of the present invention includes concatemers and peptide segments that have been incorporated into transformed soybeans. Concatemers may be a) contiguous or b) separated by a finite number of irrelevant amino acids (e.g., a single glycine residue or a sequence of 6 glycine residues), c) separated by amino acids representing known proteolytic cleavage sites (e.g. trypsin, chymotrypsin, serine protease, caspase, etc.), or d) separated by cysteine residues to allow disulfide bond formation. Generally, these concatemers and peptide segments will present an epitope that can be recognized by B lymphocytes (and thus, serve as a vaccine).

Subunit Vaccines or Toleragens Containing a Peptide Segment, or Concatemers of Homologous Peptide Segments, or Concatemers of Heterologous Peptide Segments Representing CD4+ T Helper Lymphocyte Epitopes The subunit vaccines of the present invention includes concatemers and peptide segments that have been incorporated into transformed soybeans. Concatemers may be a) contiguous or b) separated by a finite number of irrelevant amino acids (e.g., a single glycine residue or a sequence of 6 glycine residues), c) separated by amino acids representing known proteolytic cleavage sites (e.g. trypsin, chymotrypsin, serine protease, caspase, etc.), or d) separated by cysteine residues to allow disulfide bond formation. Generally, these concatemers and peptide segments will present an epitope that can be recognized by CD4+ T lymphocytes (and thus, serve as a vaccine).

Subunit Vaccines or Toleragens Containing a Peptide Segment, or Concatemers of Homologous Peptide Segments, or Concatemers of Heterologous Peptide Segments Representing CD8+ T Lymphocyte Epitopes The subunit vaccines of the present invention includes concatemers and peptide segments of homologous or heterologous that have been incorporated into transformed soybeans. Concatemers may be a) contiguous or b) separated by a finite number of irrelevant amino acids (e.g., a single glycine residue or a sequence of 6 glycine residues), c) separated by amino acids representing known proteolytic cleavage sites (e.g. trypsin, chymotrypsin, serine protease, caspase, etc.), or d) separated by cysteine residues to allow disulfide bond formation. Generally, these concatemers and peptide segments will present an epitope that can be recognized by CD8+ T lymphocytes (and thus, serve as a vaccine).

Subunit Vaccines or Toleragens Containing a Peptide Segment, or Concatemers of Homologous Peptide Segments, or Concatemers of Heterologous Peptide Segments Representing Gamma-delta T Cell Epitopes The subunit vaccines of the present invention includes concatemers and peptide segments of homologous or heterologous that have been incorporated into transformed soybeans. Concatemers may be a) contiguous or b) separated by a finite number of irrelevant amino acids (e.g., a single glycine residue or a sequence of 6 glycine residues), c) separated by amino acids representing known proteolytic cleavage sites (e.g. trypsin, chymotrypsin, serine protease, caspase, etc.), or d) separated by cysteine residues to allow disulfide bond formation. Generally, these concatemers and peptide segments will present an epitope that can be recognized by gamma-delta T cells (and thus, serve as a vaccine).

Subunit Vaccines or Toleragens Containing a Peptide Segment, or Concatemers of Homologous Peptide Segments, or Concatemers of Heterologous Peptide Segments Representing Pattern Recognition Receptor Epitopes The subunit vaccines of the present invention includes concatemers and peptide segments of homologous or heterologous that have been incorporated into transformed soybeans. Concatemers may be a) contiguous or b) separated by a finite number of irrelevant amino acids (e.g., a single glycine residue or a sequence of 6 glycine residues), c) separated by amino acids representing known proteolytic cleavage sites (e.g. trypsin, chymotrypsin, serine protease, caspase, etc.), or d) separated by cysteine residues to allow disulfide bond formation. Generally, these concatemers and peptide segments will present an epitope that can be recognized by pattern recognition receptors (and thus, serve as a vaccine).

Subunit Adjuvants Containing a Single Protein

The present invention also relates to subunit adjuvants containing a single protein. The single protein adjuvant serves the function of increasing the efficacy of the immune response to the vaccine. Essentially, any protein which is contained within a single open reading frame can be expressed in soybeans for use as an adjuvant once a synthetic, plant-compatible gene is made and transformation is performed.

These single protein subunit adjuvants are expressed in soybeans and can either be co-expressed with the protein of the vaccine, or alternatively, the adjuvant can be expressed in separate soybeans and administered to individuals separately from the soybeans that serve as the edible vaccine. Modifications of these single protein subunit adjuvants are contemplated and are within the scope of the present invention. These modifications include:

a) amino acid changes at specific residues in the original protein sequence which might change the stability of the protein, change the immunogenicity of the protein, change the solubility of the protein, change the glycosylation of the protein, or change the phosphorylation of the protein.

b) conserved amino acid changes at specific residues in the original protein sequence to construct similar, but distinct proteins (e.g. a change from glutamic acid to aspartic acid).

c) non-conserved amino acid changes at specific residues in the original protein sequence to construct similar, but distinct proteins (e.g. a change from glutamic acid to glutamine).

d) addition of amino acids at the N-terminus or C-terminus to target proteins to specific cellular locations (for example, chloroplast, endoplasmic reticulum, seed, mitochondria, etc.).

Subunit Adjuvants Containing Multiple Proteins

In addition to the single protein subunit vaccines disclosed above, the present invention also encompasses subunit vaccines that contain multiple proteins. Almost any protein which is contained within two or more open reading frames can be expressed in soybeans for use as an adjuvant once synthetic, plant-compatible genes are made and transformation is performed. However, there are additional considerations, including, the use of the same or different regulatory elements for each of the proteins to be expressed that should be considered.

In an embodiment discussed in more detail below, an example of a subunit adjuvant that contains multiple proteins is the E. coli heat labile toxin for use as an adjuvant in humans or livestock.

It should be apparent to those of ordinary skill in the art that the subunit vaccines that contain multiple proteins can encompass modifications of the original protein sequence. These modifications include:

a) amino acid changes at specific residues in the original protein sequence which might change the stability of the protein, change the immunogenicity of the protein, change the solubility of the protein, change the glycosylation of the protein, or change the phosphorylation of the protein.

b) conserved amino acid changes at specific residues in the original protein sequence to construct similar, but distinct proteins (e.g. a change from glutamic acid to aspartic acid).

c) non-conserved amino acid changes at specific residues in the original protein sequence to construct similar, but distinct proteins (e.g. a change from glutamic acid to glutamine).

d) targeting sequences to direct one or both proteins to various cellular locations.

Subunit Vaccines or Toleragens Containing a Peptide Segment, or Concatemers of Homologous Peptide Segments, or Concatemers of Heterologous Peptide Segments Co-Expressed with Proteins or Peptides which Target Binding to Receptors on Epithelial Cells to Facilitate Deliver Essentially any vaccine or toleragen construct can be co-expressed as a fusion protein with proteins or peptides which target binding to epithelial cells in the gastrointestinal tract. For example, the plant lectin protein, Ulex europaeus agglutinin I can be coupled to vaccines or toleragens to facilitate uptake by specialized epithelial cells called "M" cells (Vaccine, 2005 23:3836-42 incorporated by reference in its entirety). Thus, the present invention encompasses any of the vaccines or toleragen constructs described generically or specifically herein wherein the vaccine or toleragen is co-expressed as a fusion protein with proteins or peptides, which target binding to epithelial cells.

Subunit Vaccines or Toleragens Containing a Peptide Segment, or Concatemers of Homologous Peptide Segments, or Concatemers of Heterologous Peptide Segments Co-expressed with Proteins which Function as Adjuvants or Co-stimulatory Molecules The present invention also encompasses concatemers and/or peptide segments that are co-expressed with proteins that function as adjuvants or co-stimulatory molecules. Essentially any vaccine or toleragen can be co-expressed as a fusion protein with proteins or peptides which can function as adjuvants. For example, the adjuvant, E. coli heat labile toxin, can be co-expressed with any vaccine or toleragen. For example, the co-stimulatory molecule CD40 can be co-expressed with any vaccine or toleragen. As another example, the cytokine, IL-2, can be co-expressed with any vaccine or toleragen.

The present invention also encompasses mutants of the concatemers and/or peptide segments that are co-expressed with proteins that function as adjuvants or co-stimulatory molecules. The mutants include:

a) amino acid changes at specific residues in the original protein sequence which might change the stability of the protein, change the solubility of the protein, change the glycosylation of the protein, or change the phosphorylation of the protein.

b) conserved amino acid changes at specific residues in the original protein sequence to construct similar, but distinct proteins (e.g. a change from glutamic acid to aspartic acid).

c) non-conserved amino acid changes at specific residues in the original protein sequence to construct similar, but distinct proteins (e.g. a change from glutamic acid to glutamine).

Soybean Formulations for Soybean Based Vaccines and Adjuvants in Humans and Animals After transformation, selection and growth of the transgenic soybeans containing any of the above discussed embodiments, one can collect the soybeans and process the soybeans for consumption. The soy formulations can be prepared in the following forms:

Soy Protein Powder Formulations:

1) In the soy protein powder formulation, the formulation involves a process wherein one grinds soybeans, extracts lipids, oils, and carbohydrates using known extractants leaving the soy protein containing the particular antigen or adjuvant of interest (for extracting lipids, oils, and carbohydrates from a solution, see, for example, http://www.fao.org/docrep/t0532e/t0532e04.htm visited on Oct. 12, 2005). Then one dries the soy protein powder using any of a known drying techniques (e.g., rotary evaporation or lyophillization). The optimization of the process for this formulation into soy protein powder of each antigen or adjuvant for human or animal consumption is within the purview of those of skill in the art and should take into account the following factors:

a) the stability of antigen or adjuvant b) the suitability for consumption of soy protein powder by humans or animals c) the geographic location for vaccine administration (e.g., third world versus developed countries) which might affect the availability of electricity, storage considerations (e.g., refrigeration), or technical knowledge of the individuals expected to utilize the formulation.

Soy Milk Formulations:

1) In the soy milk formulation, this process involves grinding soybeans into a powder, solubilizing soy beans in an aqueous suspension containing the particular antigen or adjuvant, and treating the suspension in a manner (e.g. heating) which makes it compatible for human and/or animal consumption. Optionally, the suspension is pressed through a filter and the soy milk is collected in a vessel, which may or may not contain adjuvant. The optimization process of the generating soy milk is within the purview of one of skill in the art. The person of skill in the art in the process for formulation into soy milk of each antigen or adjuvant for human or animal consumption should take into account:

a) the stability of antigen or adjuvant
b) the suitability for consumption of soy protein powder by humans or animals
c) the geographic location for vaccine administration (e.g. third world versus developed countries) which might affect availability of electricity, storage considerations, or technical knowledge of the individuals expected to utilize the formulation.

Dehydrated Soybeans

1) In the dehydrated soybean formulation, the soybeans follow known dehydration procedures such as rotary evaporating the soy milk or lyophillization procedures, which are well within the purview of those of skill in the art. All of these processes must be performed under GFP conditions if human use is intended.

Human, Veterinary, Agricultural, and Wildlife Applications of Soybean Based Vaccines and Adjuvants As was discussed briefly above, the soy formulations of the instant invention can be used in a plurality of animals including but not limited to humans and other primates, to veterinary uses such as uses in dogs, cats, horses, and/or birds, in agricultural animals including but not limited to cattle, pigs, sheep, horses (donkeys, mules), goats, chickens, ducks, fish (catfish, trout), and for wildlife including but not limited to deer, elk, moose, waterfowl (ducks, geese), birds (blackbirds), and/or fish.

The soybean formulations that are used for the above enumerated animals can be in the form of Protein Subunit vaccines, which serve a plurality of functions including but not limited to viral vaccines, bacterial vaccines, fungal vaccines, parasite vaccines, prion vaccines, microbial Toxin vaccines, zoonotic disease vaccines to treat wildlife (i.e., rabies vaccine for raccoons, foxes, skunks), anti-vector vaccines to target mosquitoes, ticks, fleas, which spread disease, plant toxin vaccines (i.e., Ricin), cancer vaccines, and/or mutant self protein vaccines (heterologous chromosomal expression).

The soybean formulations that are used for the above enumerated animals can also be in the form of Protein Subunit toleragens (desensitization antigens and autoimmune antigens), which can be used to treat individuals against a number of allergens, including but not limited to plant allergens (e.g., pollen), invertebrate allergens (e.g., dust mite allergens), microbial allergens (e.g., mold spore allergens), or for Fc receptor for IgE molecules on mast cells and basophils.

The soybean formulations that are used for the above enumerated animals can also be in the form of protein subunit self-antigens including but not limited to thyroid antigens targeted to combat hyperthyroidism, agonist sites of growth hormone receptors to treat dwarf/stunted growth syndrome or for example, to make farm animals grow bigger, for antagonist sites of "addiction" receptors, for IgE molecule as an immunogen to prevent all allergies, for prostate antigens to combat prostatitis, and or for any organ that a surgeon routinely takes out due to inflammation or dysfunction.

The soybean formulations that are used for the above enumerated animals can also be in the form of protein Subunit adjuvants, co-stimulatory molecules, and/or cytokines.

The soybean formulations of the instant invention have uses as vaccines for third world countries that would not be pursued for commercialization by companies due to the limited potential for profits.

The soybean formulations that are used for the above enumerated animals can also be in the form of oral contraceptive vaccines including but not limited to vaccines which target self proteins necessary for completion of the reproductive cycle. (e.g., LHRH, FSH, sperm antigens and oocyte zona pellucida antigens). The formulation can be used to sterilize farm animals by vaccinating against self proteins (e.g., testicular antigens, ovarian antigens). Moreover, the soybean formulations of the present invention can be used for food supplements, in addition to the desired vaccine effect.

Military Applications for Soybean Based Vaccines and Adjuvants

The soybean formulations that are used in the above enumerated animals can also be used for vaccines which can be stockpiled for long periods of time (i.e., in soybeans) for a wide variety of vaccines against known agents of bio-terrorism (e.g., for smallpox, anthrax, etc.). This would limit threat and possible use by terrorists if the terrorists knew of the existence of such vaccine stockpiles.

The soybean formulations of the instant invention have a plurality of advantages that are discussed throughout this disclosure (for example cost). One other advantage is the fact that the storage of soybean seeds containing a desired antigen or toleragen can be done for prolonged periods of time (and eliminate the needs for refrigeration or any cold chain needed during its manufacture). Soybeans can also be grown in regulated greenhouses (versus outdoors), which will increase the number of generations that can be grown within the year, and also contain the GMOs (genetically modified organisms).

In one example, the strategy stimulates protective memory T helper lymphocyte and memory B lymphocyte activity, coupled with an alternative strategy to stimulate protective memory T helper lymphocyte and memory Cytotoxic T lymphocyte activity.

Having described the uses of the instant invention in general, the following passages look at specific embodiments that flush out these general uses. In a first embodiment, a strategy for development of two different oral vaccines against Hepatitis A virus is given:

Development of a Vaccine to Stimulate a Memory T Helper Lymphocyte Response, and Mucosal IPA and Systemic IgG Antibodies (and Memory B Lymphocytes) Against the Surface Antigens of Hepatitis A.

A subunit immunogen is encoded by a synthetic gene optimized for expression in soybean expressing the complete coding region for Hepatitis A structural (capsid) protein, which is given below in the amino acid one letter code.

SEQ ID NO: 52

MRPRPILLLLLMFLPMLPAPPPGQPSGRRRGRRSGGSGGGFWGDRVDSQP

FAIPHIHPTNPFAPDVTAAAGAGPRVRQPARPLGSAWRDQAQRPAATSRR

RPTTAGAAPLTAVAPAHDTPPVPDVDSRGAILRRQYNLSTSPLTSPVATG

TNLVLYAAPLSPLLPLQDGTNTHIMATEASNYAQYRVARATIRYRPLVPN

AVGGYAISISFWPQTTTTPTSVDMNSITSTDVRILVQPGIASELVIPSER

LHYRNQGWRSVETSGVAEEEATSGLVMLCIHGLPVNSYTNTPYTGALGLL

DFALEFEFRNLTPGNTNTRVSRYSSTARHRLRRGADGTAELTTTAATRFM

KDLYFTSTNGVGEIGRGIALTLFNLADTLLGGLPTELISSAGGQLFYSRP

VVSANGEPTVKLYTSVENAQQDKGIAIPHDIDLGESRVVIQDYDNQHEQD

RPTPSPAPSRPFSVLRANDVLWLSLTAAEYDQSTYGSSTGPVYVSDSVTL

VNVATGAQAVARSLDWTKVTLDGRPLSTIQQYSKTFFVLPLRGKLSFWEA

GTTKAGYPYNYNTTASDQLLIENAAGHRVAISTYTTSLGAGPVAISAVAV

LAPHSALALLEDTMDYPARAHTFDDFCPECRPLGLQGCAFQSTVAELQRL

KMKVGKTREL

The gene encoding the above Hepatitis A structural (capsid) protein is synthesized using a nucleotide synthesizer. The inventors note that a plurality of possible nucleotide sequence will give the above amino acid sequence. Thus, it is contemplated and within the scope of the present invention to include any of these nucleotide sequences as the sequence that is exogenously expressed in soybean plants. Likewise, it is contemplated and within the scope of the instant invention to include any site directed mutant of the above sequence as an exogenous gene that is incorporated into soybeans. It is noted that conservative amino acid substitutions are preferred for mutants, with one amino acid substitution being preferred, or one deletion or one addition being the preferred mutants. However, it is contemplated that multiple site directed substitutions can be employed, with conservative amino acid substitutions for all of these multiple amino acids being a preferred embodiment. Preferably, any of these mutants should have 90% or more of the above sequence conserved, more preferably 95% or more of the above sequence conserved, even more preferably 98% or more of the above sequence conserved, and most preferably only one amino acid changed.

After the gene is synthesized, it is incorporated into an expression vector (generally cloned into a binary vector which is transferred into *Agrobacterium*). Soybean plants are transformed with the expression vector and selected transformants expanded.

The transformed soybeans expressing the Hepatitis A structural (capsid) polyprotein are processed to soy protein powder or soymilk for consumption. Although the vaccine is described with reference to humans, it should be understood by those of skill in the art that these vaccines are also readily available to be used by veterinarians for the treatment of animals. Moreover, putative uses for the transgenic soybean products of the instant will be discussed in some detail below.

The soy formulation is combined with an adjuvant (for example, mutant, *E. coli* heat labile toxin, LT, which is described later) and used for oral vaccine against Hepatitis A. This vaccine targets the development of memory T helper cells and memory B lymphocytes at mucosal and systemic sites. However, it is noted that although an adjuvant greatly enhances the effect that an antigen (for example, the Hepatitis A structural (capsid) protein) has at generating an immune response, it is contemplated and therefore, within the scope of the invention that an adjuvant not be used (although incorporating an adjuvant is the preferred embodiment).

The advantages of employing the above vaccine system over those that are known in the art include that the present system:

1) Does not require needles, therefore no danger of needle-associated transmission of diseases.

2) Induces an IgA response. No current vaccine induces an IgA response. Since Hepatitis A enters via a fecal-oral route, this IgA response in the gut could prevent virus from entering the circulatory system. Present vaccines only produce IgG in blood, and therefore rely on viral neutralization after the virus has already entered.

3) Should be useful for children under the age of 2. Current vaccines are not licensed for children under 2 years of age. Because of the well known safety of soy products, the safety of an oral vaccine could extend the age range eligible for vaccination.

4) Is inexpensive. Current vaccines are too expensive to prevent most of the 1.5 million cases of hepatitis A in the world today.

Development of a Vaccine to Stimulate T Helper and Cytotoxic T Lymphocyte Responses Against Internal Antigens of Hepatitis A.

In another embodiment, the subunit immunogen is encoded by a synthetic gene optimized for expression in soybean expressing the complete coding region for Hepatitis A non-structural protein:

SEQ ID NO: 53

MEAHQFIKAPGITTAIEQAALAAANSALANAVVVRPFLSHQQIEILINLM

QPRQLVFRPEVFWNHPIQRVIHNELELYCRARSGRCLEIGAHPRSINDNP

NVVHRCFLRPVGRDVQRWYTAPTRGPAANCRRSALRGLSAADRTYCFDGF

SGCNFPAETGIALYSLHDMSPSDVAEAMFRHGMTRLYAALHLPPEVLLPP

GTYRTASYLLIHDGRRVVVTYEGDTSAGYNHDVSNLRSWIRTTKVTGDHP

LVIERVRAIGCHFVLLLTAAPEPSPMPYVPYPRSTEVYVRSIFGPGGTPS

LFPTSCSTKSTFHAVPAHIWDRLMLFGATLDDQAFCCSRLMTYLRGISYK

VTVGTLVANEGWNASEDALTAVITAAYLTICHQRYLRTQAISKGMRRLER

EHAQKFITRLYSWLFEKSGRDYIPGRQLEFYAQCRRWLSAGFHLDPRVLV

FDESAPCHCRTAIRKAVSKFCCFMKWLGQECTCFLQPAEGAAGDQGHDNE

AYEGSDVDPAESAISDISGSYVVPGTALQPLYQALDLPAEIVARAGRLTA

TVKVSQVDGRIDCETLLGNKTFRTSFVDGAVLETNGPERHNLSFDASQST

MAAGPFSLTYAASAAGLEVRYVAAGLDHRAVFAPGVSPRSAPGEVTAFCS

ALYRFNREAQRHALTGNFWFHPEGLLGLFAPFSPGHVWESANPFCGESTL

YTRTWSEVDAVSSPARPDLGFASEPSIPSRAATPTPAALQPSSAPDPFPP

PSAPALGEPAPGVTAVAPAITHQTARHRRLLFTYPDGSKVFAGSLFESTC

-continued

```
TWLVNASNVDHRPGGGLCHAFYQRYPTSFDAASFVMRDGAAAYTLTPRPI

IHAVAPDYRLEHNPKRLEAARETCSRLGTAAYPLLGTGIYQVPIGPSFDA

WERNHRPGDELYLPELAARWFEANRPACPTLTITEDAARTANLAIELDSA

TDVGRACAGCRVTPGVVQYQFTAGVPGSGKSRSITQADVDVVVVPTRELR

NAWRRRGFAAFTPHTAARVTQGRRVVIDEAPSLPPHLLLLHMQRAATVHL

LGDPNQIPAIDFEHAGLVPAIRPDLAPTSWWHVTHRCPADVCELIRGAYP

MIQTTSRVLRSLFWGEPAVGQKLVFTQAAKAANPGSVTVHEAQGATYTET

TIIATADARGLIQSSRAHAIVALTRHTEKCVIIDAPGLLREVGISDAIVN

NFFLAGGEIGHQRPSVIPRGNPDTNVDTLAAFPPSCQISAFHQLAEELGH

RPAPVAAVLPPCPELEQGLLYLPQELTTCDSVVTFELTDIVHCRMAAPSQ

RKAVLSTLVGRYGRRTKLYNASHSDVRDSLARFIPTIGPVQVTTCELYEL

VEAMVEKGQDGSAVLELDLCNRDVSRITFFQKDCNKFTTGETIAHGKVGQ

GISAWSKTFCALFGPWFRAIEKAILALLPQGVFYGDAFDDTVFSAAVAAA

KASMVFENDFSEFDSTQNNFSLGLECAIMEECGMPQWLIRLYHLIRSAWI

LQAPKESLRGFWKKHSGEPGTLLWNTVWNMAVITHCYDFRDLQVAAFKGD

DSIVLCSEYRQSPGAAVLIAGCGLKLKVDFRPIGLYAGVVVAPGLGALPD

VVRFAGRLTEKNWGPGPERAEQLRLAVSDFLRKLTNVAQMCVDVVSRVYG

VSPGLVHNLIGMLQTVADGKAHFTESVKPVLDLTNSILCRVE
```

As described above for the Hepatitis A structural (capsid) protein, the gene encoding the above Hepatitis A non-structural protein is synthesized using a nucleotide synthesizer. The inventors note that a plurality of possible nucleotide sequence will give the above amino acid sequence. Thus, it is contemplated and within the scope of the present invention to include any of these nucleotide sequences as the sequence that is exogenously expressed in soybean plants. Likewise, it is contemplated and within the scope of the instant invention to include any site directed mutant of the above sequence as an exogenous gene that is incorporated into soybeans. It is noted that conservative amino acid substitutions are preferred for mutants, with one amino acid substitution being preferred, or one deletion or one addition being the preferred mutants. However, it is contemplated that multiple site directed substitutions can be employed, with conservative amino acid substitutions for all of these multiple amino acids being a preferred embodiment. Preferably, any of these mutants should have 90% or more of the above sequence conserved, more preferably 95% or more of the above sequence conserved, even more preferably 98% or more of the above sequence conserved, and most preferably only one amino acid changed.

After the gene is synthesized, it is incorporated into an expression vector (generally a binary vector which is transferred into *Agrobacterium*). Soybean plants are transformed with the expression vector and selected transformants expanded.

The Transformed soybeans expressing the structural polyprotein are processed to soy protein powder or soymilk for consumption.

As described above, the soy formulation is combined with an adjuvant (e.g. mutant LT) and used for oral vaccine against Hepatitis A. This vaccine targets the development of memory T helper cells and memory Cytotoxic T lymphocytes at mucosal and systemic sites. As with the Hepatitis A structural (capsid) protein, this methodology has advantages, some of which include:

1) Needles are not required. Accordingly, there is no danger of needle-associated transmission of diseases.

2) No current vaccine has been shown to induce a cytotoxic T lymphocyte response against Hepatitis A. Since Hepatitis A enters via a fecal-oral route, and then infects intestinal epithelial cells, the most efficient method for killing these virally infected cells is through the induction of memory cytotoxic T lymphocytes. Present vaccines only produce IgG in blood, and therefore rely on viral neutralization after virus has already entered.

3) Once a hepatocyte is infected, the infected liver cell must be killed by the immune response so that it does not become a viral factory, producing Hepatitis A to infect other hepatocytes. The induction of a cytotoxic T lymphocyte memory response would allow for such cellular clearance of virally infected cells. Present vaccines only produce IgG in blood, and therefore rely on viral neutralization after virus has already entered.

4) Current vaccines are not licensed for children under 2 years of age. Accordingly, the present invention is advantageous in that the safety of an oral vaccine extends the age range eligible for vaccination.

5) The vaccine is inexpensive. Current vaccines are too expensive to prevent most of the 1.5 million cases in the world today.

The nucleotide sequences for Hepatitis A proteins can be found in Rizzetto, M., Purcell, R. H., Gerin, J. L. and Verme, G. (Eds.); Viral Hepatitis And Liver Disease: 313-316; Edizioni Minerva Medica, Torino (1997), which is herein incorporated in its entirety by reference.

Thus, the above proposed methods are a novel common strategy for vaccine development against a variety of microbes. Mucosal and systemic antibody (memory B cell) responses are targeted to the outer proteins (e.g. capsid proteins) of a microbe following expression of these antigens in soybeans. Antibodies bind to the surface of the microbe and prevent binding to cells or target the microbe for destruction by the immune response. It is contemplated and therefore within the scope of the invention that a concomitant (or separate) immunization strategy uses internal proteins (e.g. non-structural proteins) of a microbe to target development of a memory cytotoxic T lymphocyte response. In this manner, infected cells present these epitopes to Cytotoxic T lymphocytes, which are then targeted for lysis.

Although the above general method is described for hepatitis A proteins and their associated proteins, it should be understood that the above described method is a general method that can apply to a plurality of other viral diseases and their associated proteins. Other viral diseases and their potential targets for memory T helper cell, memory B lymphocyte, and memory Cytotoxic T lymphocyte responses are given in the below Table 2. Moreover, the availability of the sequences for these proteins and/or nucleotide sequences are given below the table.

TABLE 2

| Viral disease | Pathogen | Possible Protein target for Memory T helper cell response | Possible Protein target for Memory B cell response | Possible Protein target for Memory Cytotoxic T cell response |
|---|---|---|---|---|
| AIDS | HIV | gp120 & gp41 Gag & RT | gp120 & gp41 | Gag & RT |
| SARS | SARS Coronavirus | Spike glycoprotein nucleocapsid | Spike glycoprotein | nucleocapsid |
| Genital herpes | HSV-2 | gB and gD scaffolding proteins | gB and gD | Scaffolding proteins |
| Smallpox | Smallpox virus | Membrane protein Core proteins | Membrane protein | Core proteins |
| Encephalitis | Western Equine encephalitis | nsProtein 1–4 spike proteins | Envelope spike proteins | nsProtein 1–4 |

One HIV strain protein and/or DNA sequence(s) is described in Fang et al., Recombination following Superinfection by HIV-1, AIDS, 18 (2), 153-159 (2004), which is herein incorporated in its entirety by reference.

The SARS Coronavirus protein and/or DNA sequence(s) is described in He et al., Analysis of multimerization of the SARS coronavirus nucleocapsid protein, Biochem. Biophys. Res. Commun. 316 (2), 476-483 (2004), which is herein incorporated in its entirety by reference.

The Herpes simplex 2 protein and/or DNA sequence(s) is described in McGeoch et al., DNA sequence and genetic content of the HindIII 1 region in the short unique component of the herpes simplex virus type 2 genome: identification of the gene encoding glycoprotein G, and evolutionary comparisons, J. Gen. Virol. 68 (PT 1), 19-38 (1987), which is herein incorporated in its entirety by reference.

The smallpox sequence is not published due to accessibility to terrorists. However, the sequences can be readily obtained by those who need them for legitimate research purposes.

The West Equine Encephalitis protein and/or DNA sequence(s) is described by Netolitzky et al., which involved a direct submission on 08 Dec. 1999 to the Medical Countermeasures Section, Defence Research Establishment Suffield, P.O. Box 4000, Stn Main, Medicine Hat, Alberta T1A 8K6, Canada. All of the above references are incorporated in their entirety by reference.

Other possible subunit vaccines include polio and human ETEC toxins.

Thus, with the above description, it should be apparent that the above described protocol for generating subunit vaccines using higher plants, and in particular, soybeans is a generic method that can be employed on any of a plurality of immunogens associated with viral diseases.

Likewise, similar methodology can be applied on bacterial disease related proteins. One example of an overall strategy to develop oral vaccines that stimulate protective memory T helper lymphocyte and memory B lymphocyte activity against mutant bacterial toxins is given below.

Those of skill in the art will recognize that genes encoding mutant toxins are synthesized to encode proteins which do not have toxicity but still retain their ability to stimulate a protective response against the native toxin. Typically, at least two separate point mutations are made in the mutant toxin. A particular example is given using *Staphylococcus* Enterotoxin B (SEB) as a prototype, but it should be understood by those of skill in the art that the following protocol is a generic method that can be employed for a plurality of bacterial diseases proteins.

Strategy for Development of an Oral Vaccine Against Mutant *Staphylococcus* Enterotoxin B (SEB)

The following describes a general protocol for the development of a vaccine to stimulate a memory T helper lymphocyte response, and mucosal IgA and systemic IgG antibodies (and memory B lymphocytes) against mutant *Staphylococcus* Enterotoxin B (SEB). A more detailed protocol occurs further below. This general procedure is presented to show that the method of incorporating the exogenous gene and expressing bacterial related immunogens is a generic procedure that can be adapted to use any of a plurality of these bacterial related immunogens.

In an exemplary embodiment, a version of mutant SEB is constructed by a gene synthesizer and incorporated into a higher plant (for example, into soybeans). The soybean plants are transformed and selected transformants expanded. The transformed soybeans expressing this mutant SEB is processed to soy protein powder or soymilk for consumption. The soy formulations are combined with an adjuvant (e.g. mutant LT) and used for oral vaccine against mutant SEB. Although the preferred embodiment uses an adjuvant, it should be understood by those of skill in the art that the present invention encompasses embodiments wherein no adjuvant is used.

Vaccine Targeting the Development of Memory T Helper Cells and Memory B Lymphocytes at Mucosal and Systemic Sites The vaccine, as described above, targets the development of memory T helper cells and memory B lymphocytes at mucosal and systemic sites. This provides several advantages over the vaccines that are currently in use. These advantages include:

1) There is no need for the use of needles, and therefore there is no danger of needle-associated transmission of diseases.

2) There is no current vaccine for SEB. Thus, the transgenic soybeans of the instant invention provide a vaccine for SEB that does not exist.

It was noted above that the above process is a generic process that can accommodate a plurality of bacterial related disease. Additional examples of vaccines against mutant bacterial toxins are included in table 3 below.

TABLE 3

| Mutant Toxin | Additional information or sequence location |
| --- | --- |
| E. coli heat labile toxin (also know as LT adjuvant) | Synthetic gene optimized for expression in soybean has been made in soy plants and transformed |
| Bacillus anthracis toxins PA toxin LF toxin EF toxin | Toxin sequences are sequestered from PUBMED due to potential for terrorism, but are available |
| Clostridium tetani exotoxins | Toxin sequences are sequestered from PUBMED but are known |
| Clostridium botulinum toxin | Toxin sequences are sequestered from PUBMED but are known |

Development of a Vaccine to Stimulate a Memory T Helper Lymphocyte Response, and Mucosal IgA and Systemic IgG Antibodies (and Memory B Lymphocytes) Against the Surface Antigens of Enteropathogenic E. coli. FanC In an exemplary embodiment, a version of a subunit immunogen is encoded by a synthetic gene optimized for expression in soybean gene expressing the complete coding region for FanC. Soybean plants are transformed and the selected transformants expanded. The transformed soybeans expressing this surface antigen are processed to soy protein powder or soymilk for consumption. The soy formulation is combined with an adjuvant (e.g., mutant E. coli heat labile toxin, LT) and used as an oral vaccine against E. coli infection. This vaccine targets the development of memory T helper cells and memory B lymphocytes at mucosal and systemic sites.

Similar to the oral vaccine against mutant SEB, the transgenic soybean containing FanC has similar advantages, such as:

1) There is no need for needles and therefore, there is no danger of needle-associated transmission of diseases.

2) There are no current vaccines that induce an IgA response against FanC. Thus, this is the first vaccine against FanC.

3) The current vaccines are more expensive and therefore are not used for agriculture purposes as often as they could be.

The above protocol describes the protocol for how an oral vaccine against mutant SEB is prepared. Similarly, a general protocol is described below that shows the development of a vaccine to stimulate memory T helper lymphocyte responses against internal antigens of Mycobacterium tuberculosis.

Some bacteria are not extracellular pathogens like E. coli, but are intracellular pathogens that can live inside cells (i.e. macrophages). The causative agent for tuberculosis is such a bacterium which can live and hide inside macrophages while the disease develops. An effective immune response against such an intracellular bacterium induces T helper lymphocytes to activate the macrophage response. Therefore, this embodiment of the invention discloses vaccines that combat intracellular bacteria wherein the target is a helper T lymphocyte response.

As described above the requisite gene sequences are synthesized by a gene synthesizer (which is described in more detail below) and incorporated through a vector into the desired higher plant (e.g., soybean). As an example, a subunit immunogen is encoded by a synthetic gene optimized for expression in soybean that expresses Antigen 85 complex (Ag85 A-C) internal antigens expressed by mycobacterium tuberculosis (XX):

The DNA and/or protein sequences for Ag85-A can be found in Cole et al., Deciphering the biology of Mycobacterium tuberculosis from the complete genome sequence, Nature 393 (6685), 537-544 (1998), which is herein incorporated in its entirety by reference. The DNA and/or protein sequences for Ag85-B can be found in Matsuo et al., Cloning and expression of the Mycobacterium bovis BCG gene for extracellular alpha antigen, J. Bacteriol. 170 (9), 3847-3854 (1988), which is herein incorporated in its entirety by reference. The DNA and/or protein sequences for Ag85-C can be found in Content et al., The genes coding for the antigen 85 complexes of Mycobacterium tuberculosis and Mycobacterium bovis BCG are members of a gene family: cloning, sequence determination, and genomic organization of the gene coding for antigen 85-C of M. tuberculosis, Infect. Immun. 59 (9), 3205-3212 (1991), which is herein incorporated in its entirety by reference.

After the gene has been synthesized and incorporated into the correct vector, the soybean plants are transformed with the vector and the selected transformants are expanded. The transformed soybeans expressing the Ag85 complex is processed to soy protein powder or soymilk for consumption. The soy formulation is combined with an adjuvant (e.g. mutant LT) and used for oral vaccine against Mycobacterium tuberculosis. As above, this embodiment can be used with or without an adjuvant. However, the presence of the adjuvant is preferred. This vaccine targets the development of memory T helper cells at mucosal and systemic sites.

The vaccine as described has a plurality of advantage over currently available vaccines.: These include:

1) There is no need for needles, and therefore there is no danger of needle-associated transmission of diseases.

2) No current vaccine has been shown to induce an effective helper T lymphocyte response. BCG (live attenuated Mycobacterium bovis BCG) represents the only vaccine currently available against tuberculosis. It is the most widely administered of all vaccines in the WHO Expanded Programme for Immunization, but has been estimated to prevent only 5% of all potentially vaccine preventable deaths due to TB. It has been shown to protect against disseminated and meningeal TB in young children, and to provide some protection against leprosy, but its efficacy in preventing adult pulmonary TB, which carries the major burden of morbidity and mortality from this disease, has varied dramatically in carefully conducted studies throughout the world—from 77% in the UK to 0% in Chingleput, India. As a result of this variability in efficacy, the impact of BCG on the global TB epidemic has been negligible. Moreover, the use of BCG vaccine is not recommended for use in the US and some northern European countries because of its low efficacy and its interference with skin test screening.

Thus, it should be apparent to those of skill in the art that this general procedure to generate oral vaccines can be used on any of a plurality of bacterial related diseases, including bacterial related diseases that are not enumerated here as long as there is a target antigen that can be used. Similar to bacterial related disease, the instant invention also encompasses the development of vaccines against tumor antigens.

Development of Vaccines to Stimulate a Memory T Helper Lymphocyte Responses, Memory B Lymphocyte Responses, and/or Memory Cytotoxic T Lymphocyte Responses Against Tumor Antigens The same general procedure as used for the above disclosed viral and bacterial related diseases can be used for tumor antigens. Generally, this procedure involves synthesizing the gene encoded the desired tumor antigen(s), incorporating the gene into an appropriate vector and transforming the higher plant (preferably soybean) with the vector containing the gene of interest. Mutants that have undergone site directed mutagenesis are considered to be within the scope of the present invention. Moreover, mutants that have a plurality of conservative amino acid substitutions are considered within the scope of the present invention. Preferably, these mutants should have 90% or more homology with the wild type, more preferably 95% or more of the above sequence conserved, even more preferably 98% or more of the above sequence conserved, and most preferably only one amino acid changed. The below table 4 enumerates several antigens that are known to be cancer antigens, in what type of cancer they are found, and where the DNA and/or protein sequences for these cancers can be found.

TABLE 4

| Antigen | Cancer | Sequence information |
|---|---|---|
| MART-1 | melanoma | Kawakami et al., Cloning of the gene coding for a shared human melanoma antigen recognized by autologous T cells infiltrating into tumor, Proc. Natl. Acad. Sci. U.S.A. 91 (9), 3515–3519 (1994), which is herein incorporated in its entirety by reference |
| PSMA | Prostate | Israeli et al., Molecular cloning of a complementary DNA encoding a prostate-specific membrane antigen, Cancer Res. 53 (2), 227–230 (1993), which is herein incorporated in its entirety by reference |
| HER-2/neu | Breast ovarian | Coussens et al. Tyrosine kinase receptor with extensive homology to EGF receptor shares chromosomal location with neu oncogene, Science 230 (4730), 1132–1139 (1985), which is herein incorporated in its entirety by reference |
| CEA | Colon adenocarcinoma | Schrewe et al., Cloning of the complete gene for carcinoembryonic antigen: analysis of its promoter indicates a region conveying cell type-specific expression, Mol. Cell. Biol. 10 (6), 2738–2748 (1990), which is herein incorporated in its entirety by reference |

It should be apparent to those of skill in the art that the above procedure is a generic procedure for generating vaccines that can be used on any of a plurality of tumor antigens, including those tumor antigens that are known that are not enumerated here (as well as those that are not yet known).

Expression of Allergens or Autoimmune Antigens in Soybeans for use in the Induction of Mucosal or Systemic Tolerance:

The above describes using transgenic plants (in particular, soybeans) in the formation of vaccines from antigens that are related to viral related diseases, bacterial related diseases and tumor antigens. Transgenic higher plants such as soybeans containing a desired exogenous gene can also be used to induce tolerance in individuals prior to showing hypersensitive sensitivity to allergens. Prior to this invention, this prophylactic approach had not been used for the widespread prevention or treatment of allergic reactions and autoimmune diseases. Presently, immunotherapy may be used once an individual has demonstrated a significant hypersensitivity against a particular allergen or autoimmune disease. However, it has seemed impractical to suggest that one might be able to induce tolerance toward specific allergens and autoimmune antigens in individuals even before they demonstrate hypersensitivity or autoimmune disease. Thus, in another embodiment of the present invention, the widespread induction of tolerance as a viable method for preventing and/or treating the development of potentially life threatening allergic reactions or autoimmune diseases is presented. This embodiment encompasses giving soy protein powder or soy milk formulations derived from transgenic soybeans expressing allergens or autoimmune antigens to individuals prior to showing a hypersensitive reaction.

As an exemplary embodiment, venom phospholipase A2 is illustrated briefly here and discussed in more detail later. Venom phospholipase A2 is one of the antigens present in stings from honey bees. The general procedure is comparable to the procedure outlined above for generating vaccines. The gene of interest (in this instance, venom phospholipase A2) is synthesized on a gene synthesizer and incorporated into an expression vector. Soybeans are transformed with the expression vector, which also contains a selection marker on the plasmid backbone. The soybeans are selected using the selection marker and grown. The soybeans can be processed into soy powder and/or soy milk for consumption. Tolerance is induced by giving small quantities a number of times to the individual. The procedure is a general procedure that can be performed on any of a plurality of allergens and or antigens that may be related to autoimmune diseases. Tables 5 and 6 list a series of the allergens and autoimmune antigens, respectively that can be performed using the above enumerated general procedure. Tables 5 and 6 also contain information as to where the DNA and/or protein sequences can be found for each of the respective allergens and autoimmune antigens.

TABLE 5

| Allergens | Additional information or sequence location |
|---|---|
| *Ambrosia* (ragweed) allergen | Rogers et al., Complete sequence of the allergen Amb alpha II. Recombinant expression and reactivity with T cells from ragweed allergic patients, J. Immunol. 147 (8), 2547–2552 (1991), which is herein incorporated in its entirety by reference. |
| *Dermatophagoides* (dust mite) allergen | O'Neil et al., direct submission on 30 MAY 2005 to Molecular Biotechnology, Telethon Institute of Child Health Research, 100 Roberts Road, Subiaco, WA 6008, Australia |
| *Juniperus* (red cedar) allergen | Midoro-Horiuti et al., Identification of mutations in the genes for the pollen allergens of eastern red cedar (*Juniperus virginiana*), Clin. Exp. Allergy 31 (5), 771–778 (2001), which is herein incorporated in its entirety by reference. |
| Feline (cat) allergen | Leitermann et al., Cat allergen 1: Biochemical, antigenic, and allergenic properties, J. Allergy Clin. Immunol. 74 (2), 147–153 (1984), which is herein incorporated in its entirety by reference. |
| *Arachis* (peanut) allergen | Viquez et al., Structure and organization of the genomic clone of a major peanut allergen gene, Ara h 1, Mol. Immunol. 40 (9), 565–571 (2003), which is herein incorporated in its entirety by reference. |

TABLE 6

| Autoimmune antigens | Disease | Additional information or sequence location |
|---|---|---|
| acetylcholine receptor | Myasthenia gravis | Elliott et al., Comparative structure of human neuronal alpha 2–alpha 7 and beta 2–beta 4 nicotinic acetylcholine receptor subunits and functional expression of the alpha 2, alpha 3, alpha 4, alpha 7, beta |

TABLE 6-continued

| Autoimmune antigens | Disease | Additional information or sequence location |
|---|---|---|
| | | 2, and beta 4 subunits, J. Mol. Neurosci. 7 (3), 217–228 (1996), which is herein incorporated in its entirety by reference. |
| Myelin basic protein | Multiple Sclerosis | Roth et al., Evidence for the expression of four myelin basic protein variants in the developing human spinal cord through cDNA cloning, J. Neurosci. Res. 17 (4), 321–328 (1987), which is herein incorporated in its entirety by reference. |
| Type II collagen | Arthritis | Cheah et al., Identification and characterization of the human type II collagen gene (COL2A1), Proc. Natl. Acad. Sci. U.S.A. 82 (9), 2555–2559 (1985), which is herein incorporated in its entirety by reference. |

Thus, it should be apparent to those of ordinary skill in the art that any of the above nucleotide sequences of the allergens and/or autoimmune antigens can be incorporated into soybeans, which expresses the correlated protein.

In an embodiment of the invention, minor variants to the protein sequence of allergens and/or autoimmune antigens can be made. A single mutation can be made or alternatively several amino acids can be substituted. Generally, conserved amino substitutions are preferred. Moreover, the mutants should have preferably 90% or more of the wild-type sequence of the above sequence conserved, even more preferably 98% or more of the wild-type sequence conserved, and most preferably only one amino acid changed from the wild-type.

Development of Vaccines to Stimulate a Memory T Helper Lymphocyte, Memory B Lymphocyte, and/or Memory Cytotoxic T Lymphocyte Mucosal and Systemic Responses Against Diseases of Animals of Agricultural Importance The same general procedure as disclosed above for preparing vaccines to viral and bacterial related diseases, tumor antigen(s) and autoimmune related diseases can also be used for developing vaccines that stimulate responses against diseases in animals of agricultural importance. The process as disclosed above should be followed. The process involves incorporating the gene of interest (after synthesis) into an appropriate vector and transforming the higher plant (preferably soybean) with the vector containing the gene of interest. The transformed soybeans are selected, grown and then collected. The soybean in a purified or unpurified form can be fed to animals in a single dose or in multiple doses to stimulate the desired response.

A series of antigens are known that are important in these animal related diseases and are thus the target of the instant invention. One of skill in the art should note that mutants that have undergone site directed mutagenesis are considered to be within the scope of the present invention. Moreover, mutants that have a plurality of conservative amino acid substitutions are considered within the scope of the present invention. Preferably, these mutants should have 90% or more homology with the wild type, more preferably 95% or more of the above sequence conserved, even more preferably 98% or more of the above sequence conserved, and most preferably only one amino acid changed. Table 7 enumerates several antigens and the microbes that contain the antigen, and where the DNA and/or protein sequences for these antigens can be found.

TABLE 7

| Antigen | Microbe | Sequence information and comments |
|---|---|---|
| Envelope glycoprotein E1 and E2 | Bovine viral diarrhea virus (BVDV) | Colett et al. Molecular cloning and nucleotide sequence of the pestivirus bovine viral diarrhea virus, Virology 165 (1), 191–199 (1988), which is herein incorporated in its entirety by reference. Vaccine targets mucosal IgA, memory B cell, and T helper cell responses |
| Capsid protein | Bovine viral diarrhea virus | Colett et al. Molecular cloning and nucleotide sequence of the pestivirus bovine viral diarrhea virus, Virology 165 (1), 191–199 (1988), which is herein incorporated in its entirety by reference. Vaccine targets memory cytotoxic T and T helper cell responses |
| Envelope glycoprotein B | Equine herpesvirus | Holloway et al., Identification, sequence analysis and characterization of equine herpesvirus 5 glycoprotein B, Arch. Virol. 144 (2), 287–307 (1999), which is herein incorporated in its entirety by reference. Vaccine targets mucosal IgA, memory B cell, and T helper cell responses |
| Capsid protein | Equine herpesvirus | Telford et al., The DNA sequence of equine herpesvirus-1, Virology 189 (1), 304–316 (1992), which is herein incorporated in its entirety by reference. vaccine targets memory cytotoxic T and T helper cell responses |
| FanC | E. coli | See above and below in the instant written description |
| Fimbrae | Pasteurella | Saad et al. Direct Submission on 21 OCT. 2004 to Pathology and Microbiology Veterinary, Faculty of Veterinary Medicine, Universiti Putra Malaysia, Seri Kembangan, Selangor 434000, Malaysia vaccine targets mucosal IgA, memory B cell, and T helper cell responses |
| leukotoxoid | Pasteurella | Lo et al., Nucleotide sequence of the leukotoxin genes of *Pasteurella haemolytica* A1, Infect. Immun. 55 (9), 1987–1996 (1987), which is herein incorporated in its entirety by reference. Vaccine targets systemic IgG, memory B cell, and T helper cell responses |
| V1hA family | Mycoplasma | Papazisi et al., The complete genome sequence of the avian pathogen *Mycoplasma gallisepticum* strain R(low), Microbiology (Reading, Engl.) 149 (Pt 9), 2307–2316 (2003), which is herein incorporated in its entirety by reference. vaccine targets memory cytotoxic T and T helper cell responses |

Thus, using the above described process of gene synthesis, exogenous gene incorporation into soybeans, selecting transformed soybeans, growing and collecting the soybeans, one can treat BVDV. BVDV has a high prevalence in the cattle population. Currently, it is mandatory that BVDV vaccination be done to decrease potential losses due to BVDV infection.

The use of killed or modified-live vaccines is the method currently used and can provide protection by decreasing the consequences of acute infections. However, it is questionable whether killed or modified-live vaccines provide complete fetal protection from the development of in utero fetal infections. Moreover, the vaccine of the present invention will put less stress on cattle because the cattle can simply eat the soybeans rather than having to receive vaccinations.

Likewise, the above described methodology for BVDV can be used for Equine herpesvirus. An inactivated carbomer-adjuvated EHV-1/EHV-4 vaccine (DUVAXYN®) is a currently used vaccine. This vaccine has had its efficacy tested for reducing abortions caused by EHV-1 in a small group of mares. Pregnant mares were vaccinated 3 times during pregnancy and control mares were left unvaccinated. At 4 weeks after the third vaccination, the mares were exposed to a strain of EHV-1 that is known to cause abortions in pregnant mares. All of the control mares aborted between days 15 and 16 post infection. Of the vaccinated mares, 20% aborted and 80% maintained their pregnancies and delivered healthy foals. Thus, it was concluded that an inactivated, adjuvant vaccine based on EHV-1 and EHV-4 antigens was safe for pregnant mares and significantly reduces the incidence of EHV-1 induced abortions. The vaccine of the present invention will put less stress on cattle because the cattle can simply eat the soybeans rather than having to receive vaccinations.

Similarly, the above described methodology can be used for Pasteurella. The Pasteurella bacteria, even though they all are derived from the same species, are not all the same. It is know that there are as many as 15 different strains of Pasteurella haemolytica. Thus, a vaccine made with one strain does not always protect against other strains. For these reasons, the popularity of Pasteurella vaccines has decreased in recent years. However, farmers in a particular region may find a Pasteurella vaccine that works for the strain that is in their particular area and use it. The vaccines are currently manufactured with killed bacteria. At least two live avirulent REPLICATING Pasteurella vaccines are on the market. However, objections to their use generally include: 1) high cost; 2) adverse reactions which include injection site pain, swelling or abscesses, and muscle stiffness; 3) the administration of antibiotics or sulfa drugs at the same time as vaccination is thought to kill the live vaccine organisms and cause vaccination failure; and 4) in one case, the vaccine was recommended only for use in calves over three months of age. Since many shipped cattle are routinely administered antibacterial drugs on arrival, the use of these particular vaccines in recently shipped cattle has been questioned. Thus, it should be apparent to those of ordinary skill in the art that the instant invention using transgenic soybeans that have expressed the Pasteurella antigen has many advantages over the vaccines in current use. The cost is less, the cattle do not suffer from adverse reactions from injections (because the vaccine is eaten), and a dosage can be prepared that is very high (still inexpensively) so that even if cattle are treated with antibiotics or sulfa drugs, the vaccine may still be effective. Moreover, cattle younger than 3 months can likely be treated.

Similar to the above-enumerated cattle diseases, Mycoplasma, which affects chickens can also be treated. Mycoplasma infections are intracellular infections and, therefore one must target cell mediated immunity. Mycoplasma infection is a major cause of production loss in chickens all aroLuLd the world. The currently available vaccines partially protect breeder chickens from clinical disease, but do not eliminate the pathogen. The extensive use of antibiotics has lead to severe resistance problems and utmost care must be given to select the right antibiotic to ensure a successful treatment.

Development of Oral Contraceptive Vaccines for Animals of Agricultural Importance, Pets, and for Wildlife The above enumerated methods for generating vaccines can also be used in the development of oral contraceptives for animals of agricultural importance, pets and for wildlife. One instance where this might apply is in a given deer population wherein the deer population in a given location is too high. By feeding deer transgenic soybeans that have an antigen that functions as an oral contraceptive, the deer population can be reduced preventing a plurality of problems (such as loss of crops due to mastication by large deer populations, large deer die-offs in the winter, etc.). In this embodiment of the invention, a subunit immunogen will be encoded by a synthetic gene optimized for expression in soybean expressing the complete coding region for proteins expressed on sperm or eggs that are necessary for gametogenesis or fertilization.

The general method involves transforming the Soybean plants, selecting the transformed soybeans, and then expanding the selected transformants. The selected transformants are grown and collected. The Transformed soybeans expressing this protein are processed so they are used as seeds or processed to soy powder, or alternatively, they are left unprocessed. The processed or unprocessed transgenic soybeans can then be fed to animals and used as an oral contraceptive. Alternatively, the soy formulation can be combined with adjuvant seeds or soy powder (e.g. mutant *E. coli* heat labile toxin, LT) and used with seeds or powder expressing antigen. The vaccine targets the development of memory T helper cells and memory B lymphocytes at systemic sites.

The normal, cellular prion protein ($PrP^C$) is encoded by the PRNP gene and is found within cells in the central nervous system. However, a variant form of the prion protein referred to as abnormal, scrapie prion ($PrP^{Sc}$) can transmit prion-mediated diseases when consumed.

Bovine Spongiform Encephalopathy and Chronic Wasting disease are prion diseases of cattle and free range ruminants (e.g., elk and deer), respectively. It is thought that these diseases are transmitted by eating feed containing prion proteins which can cause disease. Since humans consume these animals, there have been some reports of spread of prion-related diseases following consumption of contaminated meat. The neurological disease which humans get following consumption of contaminated meat is called Variant Creutzfeldt-Jakob Disease. It is thought that approximately 155 humans in the United Kingdom have presented with this disease.

Some investigators have used parenteral immunizations of mice with prion proteins to limit development of prion-like disease in rodent models. However, it is not clear how practical such immunizations would be for wildlife (e.g., elk and deer) since delivery to such animals would be a significant problem. Furthermore, since only a small percentage of cattle (>1%) contract prion related diseases, the cost-effectiveness of such widespread vaccinations would be questioned. An advantage of a soybean-based vaccine against abnormal prion proteins is the ability to deliver vaccine to wildlife or agricultural animals in a cost-effective manner.

Having described the general process and a background of prion based diseases, the following table 8 discloses the antigens and a prion protein that can be expressed by the above method as well as where the gene sequences can be found.

TABLE 8

| Antigen | Sequence information and comments |
| --- | --- |
| Gonadotrophin releasing hormone (as appears in pig) | Wu, S. L., Direct Submission on 29 OCT. 1997 to Department of Biochemistry, China Medical College, 91 Hsueh-Shih Road, Taichung, Taiwan 404, R.O.C. vaccine targets systemic IgG, memory B cell, and T helper cell responses |
| Zona pellucida proteins ZPA and ZPB (as appears in cow) | Yonezawa, et al., Molecular cloning of bovine zona pellucida glycoproteins ZPA and ZPB and analysis for sperm-binding component of the zona, Eur. J. Biochem. 268 (12), 3587–3594 (2001), which is herein incorporated in its entirety by reference. vaccine targets systemic IgG, memory B cell, and T helper cell responses |
| Epididymal protease inhibitor (Eppin) (as appears in cow) | Gene sequence given at http://www.ncbi.nlm.nih.gov/entrez/viewer.fcgi?db=nucleotide&val=61815352 Visited on Oct. 4, 2005. vaccine targets systemic IgG, memory B cell, and T helper cell responses |
| Chorionic gonadotrophin (as appears in horse) | Min et al., Nucleotide sequence of eCG a-subunit cDNA and its expression in the equine placenta, J. Reprod. Dev. 40, 301–305 (1994), which is herein incorporated in its entirety by reference. vaccine targets systemic IgG, memory B cell, and T helper cell responses |
| Human prion protein (PrP) | Kretzschmar et al., Molecular cloning of a human prion protein cDNA, DNA 5 (4), 315–324 (1986), which is herein incorporated in its entirety by reference. |

Although the above antigens in Table 8 are given for a particular species (for example, pig Gonadotrophin releasing hormone), it should be understood by those of ordinary skill in the art that other species also possess the same antigens (for example deer Gonadotrophin releasing hormone). Many of the gene sequences of these antigens are known and are thereby considered to be part of the present invention.

Prophylactic Therapy Using Phospholipase A2

As was mentioned above, general prophylactic therapy is within the scope of the instant invention. As a specific example of prophylactic therapy, the prevention of development of hypersensitivity to the bee venom allergen, phospholipase A2 (Api ml) in neonatal and adolescent mice is disclosed. Generally, to accomplish prophylactic therapy, an allergen can be expressed in soy protein and in soy milk which can be given orally to weanling mice to induce systemic tolerance. Specifically, one can express the bee venom allergen (phospholipase A2) in transgenic soybeans. Soy protein and soy milk preparations from these transgenic soybeans can then be given orally to weanling mice prior to sensitization. The ability to induce allergic reactions in these tolerized animals can then be assessed using the methodology described above for the mice that ingest the fanC transgenic soybeans.

Insertion of Phospholipase A2 into Soybeans

Hypersensitivity to hymenoptera (e.g. bee, wasp, hornet) venom in the human population has been reported to occur in approximately 1% to 5% of the population, with about 1 death per million people attributed to this allergic reaction. Interestingly, studies indicate that as many as 25% to 30% of the population are sensitized to hymenoptera venoms as indicated by the presence of detectable IgE antibodies, though most of these individuals are not classified as being hypersensitive. The risk of bee venom allergy increases with the degree of exposure, so that beekeepers are at a high risk for such hypersensitivity.

In an embodiment of the instant invention, a focus on hypersensitivity to honeybee (Apis mellifera) venom can be studied, as this is the most common insect sting which results in allergic reactions. Honeybee venom is a complex mixture of proteins (Hoffman, D. R. 1996. Hymenoptera venom proteins. Adv Exp Med Biol 391:169, which is herein incorporated by reference in its entirety), however several of these proteins as major allergens can be identified. These include phospholipase A2 (Api ml), hyaluronidase (Api m2), acid phosphatase (Api m3), and melittin (Api m4), as well as other recently identified allergens (Winningham, K. M., C. D. Fitch, M. Schmidt, and D. R. Hoffman. 2004. J Allergy Clin Immunol 114:928; Tavares, B., F. Rodrigues, C. Pereira, G. Loureiro, and C. Chieira. 2005. Allerg Immunol (Paris) 37:171, both of which are incorporated by reference in their entirety). In an exemplary embodiment of the present invention, one of the major allergens in honeybee venom, phospholipase A2, can be studied. In addition to this being a major allergen, a significant amount of information about this protein and gene sequence is known. Such information includes its nucleotide sequence (Muller, U. R. 2002. Recombinant Hymenoptera venom allergens. Allergy 57:570. Moreira, L. A., J. Ito, A. Ghosh, M. Devenport, H. Zieler, E. G. Abraham, A. Crisanti, T. Nolan, F. Catteruccia, and M. Jacobs-Lorena. 2002. Bee venom phospholipase inhibits malaria parasite development in transgenic mosquitoes. J Biol Chem 277: 40839. both of which are incorporated by reference in their entirety), and an enzymatically inactive mutant (H34Q) which still retains its ability to stimulate a hypersensitivity response in allergic patients (Wymann, D., C. A. Akdis, T. Blesken, M. Akdis, R. Crameri, and K. Blaser. 1998. Enzymatic activity of soluble phospholipase A2 does not affect the specific IgE, IgG4 and cytokine responses in bee sting allergy. Clin Exp Allergy 28:839, which is incorporated in its entirety by reference). In addition, a murine model for hypersensitivity to bee venom phospholipase A2 has been previously used to question the efficacy of various types of immunotherapy (Akdis et al. 1996. Epitope-specific T cell tolerance to phospholipase A2 in bee venom immunotherapy and recovery by IL-2 and IL-15 in vitro. J Clin Invest 98:1676; Astori, et al. 2000. Inducing tolerance by intranasal administration of long peptides in naive and primed CBA/J mice. J Immunol 165: 3497. von Garnier, et al. 2000. Allergen-derived long peptide immunotherapy down-regulates specific IgE response and protects from anaphylaxis. Eur J Immunol 30:1638, all of which are incorporated by reference in their entireties). In the present invention, we can express the enzymatically inactive mutant of honeybee venom phospholipase A2 (H34Q) (Wymann, et al. 1998. Enzymatic activity of soluble phospholipase A2 does not affect the specific IgE, IgG4 and cytokine responses in bee sting allergy. Clin Exp Allergy 28:839, which is herein incorporated by reference in its entirety) for use as an allergen in a mouse model of hypersensitivity that has been previously described (Akdis et al. 1996. Astori, et al. 2000. von Garnier, et al. 2000).

For the 1%-5% of the population that have a previous medical history of hypersensitivity to hymenoptera stings, desensitization immunotherapy is presently the only allergen-specific treatment option. For the "conventional" desensitization treatment, diluted bee venom (ALK Pharmalgen) is injected subcutaneously in patients beginning with a dose (less than 10 micrograms) that is unlikely to cause much of a systemic effect. Typically, this dose is used weekly for one month, followed by an increase in dose for the next several months until a maintenance dose of 100 micrograms is reached. During the next 3 to 5 years, the maintenance dose is given every 3 to 6 months. Such treatments are performed by medical personnel due to the possibility of side effects. In an effort to limit the time required for desensitization, there are also "rush" and "ultrarush" treatments where increasing doses of bee venom are given in an accelerated fashion. The risk of side effects from such accelerated desensitization therapy is significant enough that such therapy should be performed under close medical supervision (Birnbaum, et al. 2003. Hymenoptera ultra-rush venom immunotherapy (210 min): a safety study and risk factors. Clin Exp Allergy 33:58. Wenzel, et al. 2003. Safety of rush insect venom immunotherapy. The results of a retrospective study in 178 patients. Allergy 58:1176, both of which are incorporated by reference in their entireties.).

Desensitization immunotherapy is an effective treatment to limit hypersensitivity reactions to bee venom in most patients who receive this treatment (Golden, et al. 1996. J Allergy Clin Immunol 97:579. Ross, et al. 2000. Clin Ther 22:351. Valentine, et al. 1990. N Engl J Med 323:1601. Hunt, et al. 1978. N Engl J Med 299:157, all of which are incorporated by reference in their entireties.). Success rates for desensitization therapy have been reported to be 75% to 85% effective for honeybee immunotherapy when a maintenance dose of 100 micrograms is reached in adults (Golden, D. B. 2005. J Allergy Clin Immunol 115:439, which is herein incorporated by reference in its entirety.). An increase to a maintenance dose of 150 to 250 micrograms of bee venom has been reported to improve efficacy for those adults not protected by 100 microgram doses (Rueff, et al. 2001. J Allergy Clin Immunol 108:1027, which is herein incorporated by reference in its entirety.).

There are side effects and risks associated with this therapy despite reports of the relative safety of such immunotherapies (Golden, D. B. 2005. Birnbaum, et al. 2003, Clin Exp Allergy 33:58, which is incorporated by reference in its entirety). Side effects include: patches on the skin, itching, reddening of the skin's surface, swelling at the site of injection, raised patches on the skin at sites systemic to the injection site, inflammation of the mucosal membranes in the nose, mild or moderate difficulty in breathing, and swelling of the eyes, lips, or tongue. In a small percentage of cases, an anaphylactic reaction has been observed following immunotherapy, which included difficulty in breathing, airway obstruction, facial swelling, etc. which requires medical intervention to reverse these symptoms.

The present day immunotherapy for bee venom allergy have limitations. These limitations can be summarized as follows. 1) Time. Often greater than 20 subcutaneous injections with bee venom allergen preparations (ALK, Pharmalgen) are required over a period of 3 to 5 years in order to establish and maintain the desensitized state. This requires a significant commitment by the patient to travel to an appropriate medical facility on numerous occasions over the course of several years to comply with the particular immunotherapy regimen. 2) Cost. The cost of travel to medical clinics or hospitals, the cost of medical personnel to administer the injections, and the costs of bee venom (ALK, Pharmalgen) for multiple treatments over a period of years is a significant financial commitment for immunotherapy patients. 3) Necessity for medical supervision. As noted above (Section B3), these injections must be performed under medical supervision, and if "ultrarush" regimens are used, close medical supervision or hospitalization has been recommended. This requirement places significant limitations on where such treatments can be performed. 4) Side effects. While the side effects associated with any single injection is low, the possibility that an individual patient may have one or more side effects during one of the numerous injections over a 3 to 5 year period increases proportionately. 5) Efficacy. Although desensitization using hymenoptera venom injection is one of the most successful applications for specific immunotherapy that is presently practiced with efficacy levels of 75% to 85% for honeybee venom therapy being reported, there is a percentage of patients wherein this therapy is not effective. An increase in the maintenance dose (150 to 250 micrograms) has been suggested in patients who are not desensitized using standard doses (100 micrograms). Furthermore, efficacy in children is not altogether clear. A recent study (Golden, et al. 2004. Outcomes of allergy to insect stings in children, with and without venom immunotherapy. N Engl J Med 351:668, which is herein incorporated by reference in its entirety) demonstrated that children (age 8+3 years) having a mild to severe hypersensitivity to bee sting early in life do not always outgrow such an allergy, but can have symptoms into adulthood. Furthermore, for those children that received venom immunotherapy, it did reduce the risk of having a systemic response when they were stung by a bee with a mean of 21 years later (+5 years). However this protection into adulthood was not complete. So, immunotherapy in children appears somewhat successful, but is not absolute. 6) Unknown hypersensitivities to bee venom. Only those individuals who have already experienced a hypersensitivity reaction to a honeybee sting are indicated for immunotherapy. Diagnostic tests to identify those individuals who might have an adverse reaction to bee venom are limited by the fact that 25% to 30% of the population shows reactivity in a RAST test. Furthermore, some individuals who have a negative RAST or skin test can still have an allergic reaction to a bee sting (Reisman, R. E. 2001. Insect sting allergy: the dilemma of the negative skin test reactor. J Allergy Clin Immunol 107:781, which is herein incorporated by reference in its entirety). More troubling is the fact that about half of the deaths attributed to fatal sting reactions could not have been prevented since there was no previous indication that these individuals had any hypersensitivity (Barnard, J. H. 1973. Studies of 400 Hymenoptera sting deaths in the United States. J Allergy Clin Immunol 52:259. Hoffman, D. R. 2003. Fatal reactions to hymenoptera stings. Allergy Asthma Proc 24:123, both of which are incorporated by reference in their entireties.), and therefore they would not have been candidates for immunotherapy. 7) Non-compliance of patients for which immunotherapy is indicated. Once a patient presents with a hypersensitivity to bee stings, it is not a certainty that the individual will choose to receive such therapy. The reasons for deciding not to participate in immunotherapy are likely some combination of the problems listed above, including cost, inconvenience, the use of needles, and/or side effects associated with such therapy. In one study (Golden, D. B., A. Kagey-Sobotka, P. S. Norman, R. G. Hamilton, and L. M. Lichtenstein. 2004. Outcomes of allergy to insect stings in children, with and without venom immunotherapy. N Engl J Med 351:668, which is incorporated by reference in its entirety), of 345 children that had a moderate to severe systemic reaction to a bee sting, 99 (or 29%) chose not to undergo immunotherapy even though they were advised to do so.

Thus, despite the successes of venom-based immunotherapies, there remain some significant problems with the practicality and safety of performing these treatments. This fact is underscored by recent investigations which have sought technological advances in the field of immunotherapy in an attempt to overcome some of these limitations (Jilek, et al. 2001. J Immunol 166:3612. Muller, et al. 1998. J Allergy Clin Immunol 101:747. Muller, U. R. 2003. Curr Opin Allergy Clin Immunol 3:299. Alexander, et al. 2002. Curr Drug Targets Inflamm Allergy 1:353, which are incorporated by reference in their entirety). Thus, one embodiment of the present invention is to prophylactically apply oral allergen therapy to prevent the development of hypersensitivity in children who have not yet shown clinical symptoms. This can be a cost-effective, safe, and efficacious treatment option.

There is little doubt that high levels of allergen can be expressed in a stable form in transgenic soybeans for pennies a dose. There have been several excellent review articles documenting the successful expression of proteins in transgenic plants and the above studies with transgenic fanC show this. The ability to express foreign proteins in transgenic plants has been demonstrated, and it is clear that the technology exists to transform plants for human use. In fact, proteins that retain their enzymatic activity or functionality have been expressed in a variety of plants, indicating the potential utility of this technology for a variety of applications. The advantages of transgenic plants for production of proteins of importance to human health have also been discussed (Goldstein, et al. 2004. Qjm 97:705. Peterson, et al. 2004. Trends Biotechnol 22:64. Ma, J. K. 2000. Nat Biotechnol 18:1141. Larrick, et al. 2001. Curr Opin Biotechnol 12:411. Giddings, G. 2001. Curr Opin Biotechnol 12:450, all of which are incorporated by reference in their entireties.). The feasibility of expressing foreign proteins (but not allergens) in transgenic soybeans has also been demonstrated (Zeitlin, et al. 1998. Nat Biotechnol 16:1361. Sojikul, et al. 2003. Proc Natl Acad Sci U S A 100:2209. Smith, et al. 2002. Biotechnol Bioeng 80:812. Hatic, et al. 2001. Anal Biochem 292:171, all of which are incorporated by reference in their entireties) and the disclosure in the present invention of *E. coli* FanC shows that subunit allergens can be expressed in soybeans. When targeted to the cytoplasm, expression levels of FanC approaches 0.5% of total protein. Therefore, it is postulated that well over 1% of total protein expression of an antigen can be obtained when it is specifically targeted to expression in soybean seeds (Sato, et al. 2004. Crop Sci 44:646, which is herein incorporated by reference in its entirety.).

Presently, soybean yields are ~40 bushels/acre with a typical price of ~$6 per bushel. Since soybeans contain ~38% protein, even with 1% expression of a particular allergen, oral therapy would be pennies a dose. Therefore, the cost of numerous exposures to any particular oral toleragen in a large population of children is not a limitation to using this technology.

As are discussed herein, soy milk formulations for infant and adult consumption are safe to consume and have significant nutritional benefit (Messina, M. J. 1999. Am J Clin Nutr 70:439S. Slavin, J. 1991. J Am Diet Assoc 91:816, both of which are incorporated by reference in their entireties.). In fact, soy milk formulations are so safe that they are routinely fed to infants with little side effects (Motil, K. J. 2000. Curr Opin Pediatr 12:469. Seppo, et al. 2005. Am J Clin Nutr 82:140. Badger, et al. 2002. J Nutr 132:559S, both of which are incorporated by reference in their entireties.). Such safety also seems to apply to transgenic plants in general. In a recent review, it was noted that "... more than two trillion transgenic plants have been grown between 1999 and 2000 alone, with no overt documented adverse food reactions being reported, indicating that genetic modification through biotechnology will not impose immediate, significant risks such as food allergen sources beyond that of our daily intake of foods from crop plants." (Helm, R. M. 2003. Ann Allergy Asthma Immunol 90:90, which is incorporated by reference in its entirety.). Such safety further supports the notion that widespread therapy with allergen-containing soy milk formulations would not pose any significant risk to the majority of infants or adolescents, even if those individuals might never develop hypersensitivity to that particular allergen.

Making soybeans into forms that are palatable for human consumption are established and are numerous (Friedman, et al. 2001. J Agric Food Chem 49:1069. Lusas, et al. 1995. J Nutr 125:573S, both of which are incorporated by reference in their entireties). Furthermore, novel processing methods are presently being sought to improve existing technologies (Kitts, et al. 2003. Curr Pharm Des 9:1309, which is incorporated by reference in its entirety.).

Tofu is a well known form of soybeans that is generated by the fermenting soy protein. It is contemplated and within the scope of the invention that the transgenic soy of the instant invention can be processed in such a way. It is believed that the fermenting process may proteolize the proteins, yet nevertheless, these proteins may possess the requisite epitopes necessary to elucidate an immune response. Consequently, the instant invention contemplates that transgenic soybean that has been made into tofu is within the scope of the instant invention.

Without fermentation of soy products, a process can be readily identified that maintains allergen structure, and at the same time forms transgenic soybeans into a consumable product. The above disclosure demonstrates that soybeans expressing the bacterial protein, FanC, can be processed into soy powder and soy milk suitable for consumption and still contain intact FanC capable of stimulating a mucosal response. These studies support the notion that formulating soybeans into soy milk maintains allergen structure for use in the induction of oral tolerance.

Recent reviews (Wu, et al. 2003. Immunol Res 28:265. Mayer, L., et al. 2004. Nat Rev Immunol 4:407, both of which are incorporated by reference in their entireties.) summarize the efficacy of inducing tolerance to a variety of antigens following their oral administration. Animal models of autoimmune disease have shown some of the most promising results, especially when oral antigens are given prior to sensitization of animals to the auto-antigen. In addition, feeding of allogeneic cells or MHC proteins has shown efficacy in animal models of transplant rejection (Stepkowski, et al. 1999. Transplant Proc 31:1557. Zavazava, et al. 2000. J Leukoc Biol 67:793, both of which are incorporated by reference in their entireties.).

There have been a few attempts to use autoimmune antigens expressed in transgenic plants to limit the development of autoimmune disease in mouse models. Of note, others have used transgenic tobacco to express a diabetes associated antigen and prevent diabetes in an animal model following oral administration (Ma, et al. 2004. Proc Natl Acad Sci U S A 101:5680. Ma, et al. 1997. Nat Med 3:793, both of which are incorporated by reference in their entireties.). Other researchers have used transgenic potatoes expressing a cholera toxin B subunit-insulin fusion protein for oral tolerance induction in a mouse model of diabetes (Arakawa, et al. 1998. Nat Biotechnol 16:934, which is incorporated by reference in its entirety.).

There have also been a few attempts to induce oral tolerance to allergens. There has been some success using increasing doses of food allergens given orally to desensitize patients (Patriarca, et al. 2003. Aliment Pharmacol Ther 17:459, which is incorporated by reference in its entirety.). Unfortunately some patients react to even small doses to oral food allergens, making side effects possible in highly reactive patients. Oral tolerance has also been observed when certain pollen extracts are given to mice (Aramaki, et al. 1994. Immunol Lett 40:21. Kim, et al. 2001. Arch Pharm Res 24:557, which are incorporated by reference in their entireties). However, to the inventors knowledge this is the first studies on using transgenic soybeans to express allergens. Furthermore, the inventors believe that this is the first suggestion that one can prophylactically treat children with plant-derived allergens in an attempt to prevent the development of hypersensitivities.

Thus, the present invention shows that the technology is available to express allergens in soybeans. Furthermore, the efficacy of inducing tolerance by oral administration in pre-sensitized animals is quite compelling. To the inventors knowledge, this is the first time that one has shown that it is not necessary to purify allergens from transgenic soybeans. However, the inventors also note that soy milk formulations from such plants should also be able to be used to induce tolerance when given orally to neonatal or adolescent mice. Widespread consumption of soy formulations containing allergens to induce systemic tolerance should thus be a viable therapy for preventing the development of immediate type hypersensitivity reactions.

There are many advantages to using a preventative therapy utilizing allergens expressed in transgenic soybeans.

As noted above, the low costs of expressing allergens in transgenic soybeans for prophylactic therapy makes such treatments feasible for almost anyone. The high protein content of soybeans makes it possible to express high amounts of allergen per soybean, which is a significant advantage over other plants such as tobacco, bananas, potato and tomato previously used to express antigens.

Also noted above, the safety of soybean formulations for humans, like soy milk, is well recognized. Thus, the purification of soy-derived allergens is not a necessity. For example, previous work (Ma, et al. 2004. Proc Natl Acad Sci U S A 101:5680. Ma, et al. 1997. Nat Med 3:793) expressed a diabetes antigen in tobacco to limit autoimmune diabetes in a mouse model. While this was a significant accomplishment, this antigen would have to be purified from such plants for use in humans. Thus, the present invention is advantageous in that the safety of soy formulations permits minimal processing prior to use by humans.

Moreover, due to its safety, the oral delivery of allergens in soy milk formulations does not require medical personnel for such administration. This greatly simplifies treatment and contribute to a low cost. Further, consumption of soy milk formulations would likely be preferable to injections, especially for children. The low cost, safety and ease of administration of soy milk formulations would likely increase compliance with immunotherapeutic regimens that require several years duration to complete. The possibility exists that oral immunotherapy may produce less side effects (Helm, R. M. 2003. Ann Allergy Asthma Immunol 90:90, which is herein incorporated by reference in its entirety.) than those observed with present day injectable immunotherapy. If such a difference exists, it is likely that the route of administration (i.e. systemic versus gastric) would be responsible for the limited side effects.

Soybeans were selected for expression of our oral allergen, bee venom phospholipase A2, for several key reasons. First, soybean has relatively high protein content when compared to other transgenic plants such as tobacco, bananas, potato and tomato previously used to express antigens. The typical composition of a soybean is 38% protein, 30% carbohydrate, 18% oil, and 14% moisture and other components. Therefore, it is possible to express a toleragenic dose of allergen in one or two soybean seeds. Second, procedures for processing soybeans into forms that are palatable for human consumption are established and are numerous:

Production and purification of soybean includes 1) mass production in a factory of soy milk or soy powder containing the appropriate amount of vaccine; 2) individual, disposable vaccine extractors which might be sold over the counter, 3) and other similar systems. A novel processing method is shown in FIG. 17, which shows an extract-a-vac. The extract-a-vac employs a concept to extract vaccines from soybeans or from soy powder. The extract-a-vac works as follows.

As pictured, the concept of an extract-a-vac has two essential functions: 1) to produce a single dose of vaccine; and 2) to produce it using a disposable extractor. The extractor can be made so it is reusable. If the extractor is reusable, it should be made of a material that can withstand thorough cleaning (and possibly even being autoclaved). Alternatively, the extract-a-vac can be used for a single vaccine dose followed by disposing of the extract-a-vac. As an extracting solution one would preferably use an aqueous solution that might contain some excipients such as sucralose or some other sugar to add palatability the extraction product. The extract generally should be heated to an appropriate temperature in order to maximize the solubility of the immunogen in the aqueous extraction solvent yet not so high as to cause the degradation of the immunogen (e.g. 75° C., or that temperature empirically determined for each immunogen to be optimal for extraction). Once heated the tab as shown in FIG. 17 should be pulled to mix the extracting solution with soy protein powder containing immunogen and optionally also containing an adjuvant. In a preferred embodiment, the processing of the transgenic soybeans to soy protein powder and quantification of immunogen dose would be done prior to putting the material into each extract-a-vac. After a period of time with gentle shaking to allow solubilization of proteins, the liquid would be pressed through a filter as shown. The cup containing the soymilk formulation could then be consumed by drinking.

The extract-a-vac shows a process that can readily be used that maintains antigenicity, while formulating transgenic soybeans into a consumable product.

Many food products made for human consumption already contain soy protein suggesting that adverse reactions to orally administered soy formulations would be limited. Stated simply, immunogens would not have to be purified from soy preparations because tolerance to soy proteins would be maintained when edible immunogens derived from these plants are used.

The presence of immunogens in seeds of crop plants is advantageous due to antigen stability in seeds and transportability of these crops. Soybean seeds are likely to be stable to antigens.

The following experimental section and the associated results demonstrate several important points regarding the advantages of using transgenic soybeans to express allergens. These include: 1) the ability to obtain high levels of antigen expression; 2) the ability to formulate soybeans into consumables while still maintaining antigenicity; and 3) the stability of antigen expression in soybean formulations even after processing or long term storage.

Expression of an Enzymatically Inactive Form of Bee Venom Phospholipase A2 (Api ml) in Transgenic Soybeans An enzymatically inactive mutant of bee venom phospholipase A2, with the histidine at position 34 changed to a glutamine (H34Q), has been described. This mutant has essentially no enzymatic activity, yet retains its ability to stimulate a hypersensitivity response in allergic patients. To assure that the phospholipase activity did not cause any unforeseen problems for expression in plants, the inventors have made a plant-compatible version of the H34Q mutant for expression in soybeans.

To construct a plant-compatible version of bee venom phospholipase A2 (H34Q) several factors had to be considered. Considerations for constructing a plant-compatible version of phospholipase A2 (H34Q) included: 1) increasing the GC content to resemble plant systems; 2) removing AT-rich regions which could affect mRNA stability; 3) altering codon usage to resemble plant biases; and 4) removing the N-terminal targeting sequence. In addition, all AT-rich regions greater than five nucleotides in length were eliminated to avoid introduction of potential cryptic polyadenylation signals. Once the synthetic, plant-compatible version of bee venom phospholipase A2 (H34Q) had been designed, the actual gene was created by annealing large synthetic oligonucleotides with 30-bp overlapping regions of homology, to create a template for PCR amplification. A similar strategy is shown elsewhere in this invention disclosure wherein a construct was made to express a plant-compatible version of the *E. coli* antigen, FanC (Piller, et al. 2005. Planta 222:6, which is herein incorporated by reference.), and a mutant form of the heat labile bacterial toxin, LT (R03 AI-061102).

Transformation of Plants

A common means of transforming higher order plants is through the use of *Agrobacterium* species. An exemplary embodiment of a particular species that can be used to transform higher order plants and soybeans in particular is *Agrobacterium tumefaciens*. Other species that are contemplated and within the scope of the present invention include *A. radiobacter*, which is an "avirulent" species, *A. rhizogenes*, which is known to cause hairy root disease, and *A. rubi*. When multiple cassettes are used, the expression efficiency tends to decrease. Accordingly, a preferred embodiment limits the number of T-DNA insertions.

Particular soybean strains can be used in transformations that are tolerant to different conditions. For example, one might use elite soybean germplasm for transformation, which is resistant to rust. Alternatively, different soybean varieties can be used that are suited to a geographical region around the world for transformation (e.g. one might select a variety that is resistant to heat or drought conditions that grow well in Africa).

Soybean Transformation and $T_0$ Plant Growth

Soybean transformations are performed to generate ~25 transgenic events. The pKP43 vector is mobilized into *Agrobacterium tumefaciens* strain EHA101 by triparental mating, and transconjugants resistant to antibiotic selection are used to transform soybean as described elsewhere in this disclosure. Seeds are surface sterilized and germinated for 5 days, at which time cotyledonary explants are isolated, immersed in *A. tumefaciens* inoculum, and cultivated for 3 days. Following washing and culturing on shoot induction medium for 4 weeks, the differentiating node are separated from the cotyledons, and sub-cultured on shoot elongation medium biweekly until shoots reach a length of greater than or equal to three cm. To select for transformants, the shoot initiation and elongation medium contains 5 mg/ml and 3 mg/ml glufosinate, respectively. Elongated shoots are transferred to rooting medium and allowed to grow into plantlets. The plantlets are grown and then are transferred to soil, grown to maturity, and allowed to set $T_1$ seeds in the greenhouse.

$T_1$ seeds can then be screened to determine which lines expressing the gene encoding bee venom phospholipase A2 (H34Q) is selected for $T_1$ plant growth and $T_2$ seed formation.

Selection for Transformed Plants

Selectable Marker Cassettes are also contemplated and within the scope of the present invention. A cassette encoding a selectable marker can be included on the plant binary vector. An exemplary embodiment of a selectable marker is the bar gene encoding resistance to the herbicide bialophos. Another example is the EPSPS gene (Monsanto) encoding resistance to glyphosate. The selectable marker may impart an advantage to the soybean plant, as do the bar and glyphosate cassettes by offering resistance to herbicides. Although antibiotic selection markers are contemplated, there is some resistance from segments of the population to put antibiotic resistant strains of plants into the environment. For this reason, the herbicide resistant selection markers are preferred.

Bialophos produced by *Streptomyces hygroscopicus* is a tripeptide consisting of two L-alanine residues and an analogue of glutamic acid (phosphinothricin (PPT)). Upon cleavage of bialophos, PPT is released and acts as an inhibitor of glutamine synthesis in plants, and hence functions as a potent herbicide. A gene (bar) coding for PPT acetyltransferase has been isolated from *S. hygroscopicus* and is widely used as a selective marker for the transformation of higher plants. See DeBlock et al. 1987 EMBO J. 6:2513-2518 Avalos et al. 1989 Curr. Genet. 16:369-327; and Pall, 1993 Fungal Genet. Newsl. 40:58, which are hereby incorporated in their entirety by reference.

Expression of FanC in Transgenic Soybeans

FanC antigen has been successfully expressed in transgenic soybeans. The synthetic fanC gene targeting expression to the cytosol of plant cells (pKP7) (FIG. 2) was used for transformation of soybean plants. Primary $T_0$ transformants were subjected to molecular analyses (FIGS. 3-6). Total protein was extracted from leaves of the $T_0$ transformants and used in Western analysis to identify lines expressing the transgenic FanC protein (FIG. 4). Based on FanC accumulation levels, two lines (lines 485-1 and 485-10) were chosen for propagation and further study. To verify that the transgene had been stably inherited, $T_1$ leaf tissue was screened for the presence of the transgene. FIG. 5 shows several $T_1$ siblings that were transgenic for fanC, demonstrating stable inheritance of the gene. Because of the constitutive nature of the 35S promoter, the potential for FanC accumulation in transgenic seeds was determined. As predicted, the level of cytosolic FanC accumulation in transgenic $T_1$ seeds was comparable to that detected in $T_0$ vegetative leaf tissue (see FIGS. 4, 15, 17).

Figure 27:
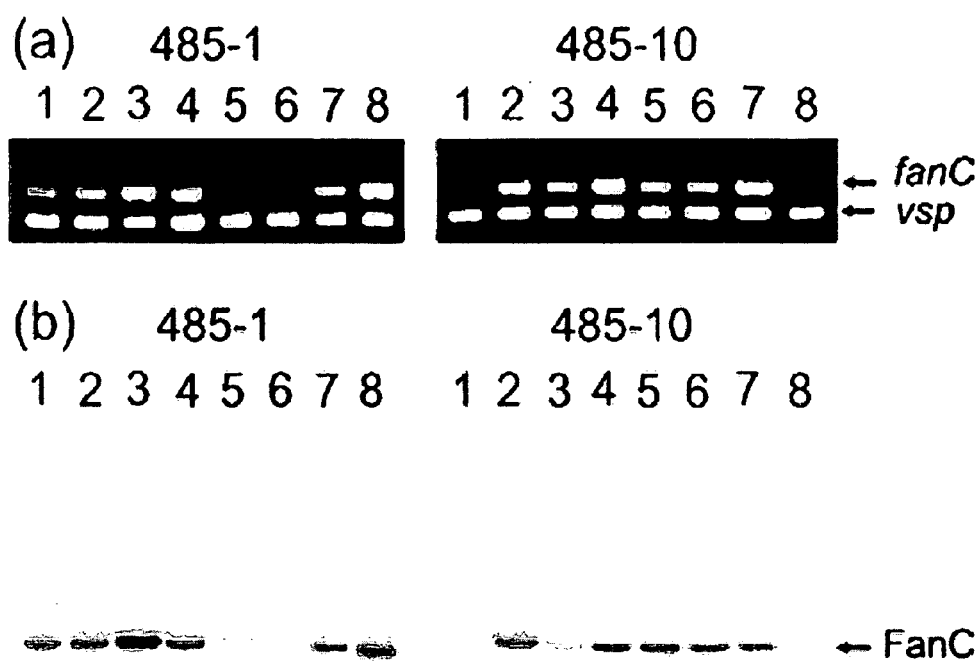

A western blot is shown in FIG. 4A demonstrating the immunological detection of FanC in vegetative tissue. The size of the detected protein correlates with the predicted mobility of FanC (i.e., 18.5 kDa). FIG. 27 shows the identification and detection of FanC protein in transgenic seeds. FIG. 3 shows the results of duplex PCR used to identify transgenic progeny. FIG. 27 shows a western blot on seed protein.

The immunogenicity of soybean-derived FanC was also demonstrated. Mice immunized with soybean-derived FanC not only had significant antibody titers, but also had antigen-specific CD4+ T cell responses against this antigen.

Analysis and Screening of T1 Plants Containing FanC Targeted to the Chloroplast

FanC was also targeted to the chloroplast to examine expression, accumulation, and immunogenicity of the antigen. Soybean plants were transformed with pKP8 (FIG. 19) which is analogous to pKP7 except that pKP8 contains a sequence coding for a chloroplast targeting peptide at the 5' end of the fanC open reading frame (Table 1). Thus, expression and accumulation of this synthetic FanC product should be targeted to chloroplasts. Because of the constitutive nature of the 35S promoter, it is expected that expression may occur in any green tissues that contain chloroplasts. Following transformation with pKP8, leaf tissue was assayed for the presence of the fanC gene by duplex PCR and for the presence of transgenic FanC protein by Western analysis. All lines that tested positive for expression were allowed to set seed. To demonstrate that the fanC gene was stably inherited, T1 seeds were planted from each of the T0 lines expressing FanC, and T1 tissue was collected for duplex PCR and Western analysis. FIG. 26 shows eight different parental lines whose progeny test positive for the transgene as determined by a duplex PCR assay. Western analysis of protein derived from leaves of each T1 progeny (FIG. 26) demonstrated that 64% expressed transgenic FanC in the chloroplast. Furthermore, at least one progeny from each of the 8 parent lines accumulated measurable levels of FanC. Based on the intensity of the Western signal, lines 502-5 and 504-10 were chosen for further analysis.

Processing or Purification of FanC from Soybean Seeds is not Required for Immunogenicity.

Two whole transgenic soybean seeds expressing FanC were given to mice to consume (FIG. 15A). After 1 hour mice had readily consumed both seed and were then given a dose of the oral adjuvant LT. Following an immunization regimen (i.e., three boosts every 10 days), mice developed significant antibody responses and CD4+ T cell responses against FanC. This demonstrates that antigen does not have to be purified from soybeans to serve as an effective immunogen (FIG. 15B).

Stability of Expression of FanC in Soy Powder and Soy Milk Formulations Made from Transgenic Soybean Seeds In the present invention, soy powder and soy milk can be formulated from transgenic seeds expressing the allergen. The stability of antigens within such soybean formulations once processed was tested. FIG. 14 shows the processed transgenic soybeans expressing FanC to soy powder (lanes 2, 5) and soy milk (lanes 3, 6). The antigen stability in such preparations was determined using western blot analyses. As shown in FIG. 14, intact FanC is present in soy powder (lanes 2 and 5) and soy milk (lanes 3 and 6) formulations. Furthermore, there is no detectable breakdown observed even when using a polyclonal anti-FanC antibody which detects multiple epitopes on FanC.

The stability of FanC in soybean seeds after storage at room temperature for 18 months was tested. The storage of transgenic soybean seeds for long periods of time at room temperature while still maintaining the stability of FanC was shown. FIG. 14 shows the results of soy powder and soy milk formulations made from transgenic soybean seeds expressing FanC after being stored for 18 months at room temperature. These striking results further demonstrate the stability of FanC expressed in transgenic soybeans even after long-term storage. This result demonstrates that using transgenic soybeans to store immunogens in situations that lack refrigeration may prove to be advantageous relative to the purified immunogens that often require refrigeration.

Long Term Stability of FanC in Soybean Leaves and Seeds

FIG. 14 shows antigen stability in 18 month old stored seeds used to make different formulations that could be applied to commercial scale-up. The stability of transgenic FanC following long term storage and formulation into soy protein and soymilk formulations is shown. T1 transgenic seeds (line 485-10) were stored for 18 months, and then used in various different formulations. The first formulation served as a control, and seeds were extracted with buffer as previously described (Piller, et. al 2005, 222, 6) (Lanes 1 and 4). In the second formulation, seeds were treated with hexane, ethanol, and heat, analogous to commercial methods for making soy flour and soy flakes. For this formulation, seeds were de-hulled and ground to a fine powder. The powder was extracted with 10 parts of warm hexane, and then washed in 100% ethanol and heated to 90° C. for 10 minutes. Proteins were then extracted from the protein-enriched soy powder for use in Western analysis (Lanes 2 and 5). In the third formulation, soymilk was extracted as would be accomplished using either commercial or personal soymilk makers such as the SoyQuick Soymilk Maker (Kitchen's Best Manufacturing Group, Ltd.) or the Hurricane Soymilk Maker (Internet Kits, Inc.). Soymilk was subjected to boiling at 100° C. for 10 minutes and clarified prior to use in the Western analysis (Lanes 3 and 6). Protein from the preparations was quantified, and either 30 micrograms or 100 micrograms of protein was subjected to Western blot analysis using a polyclonal anti-FanC antibody to determine whether intact FanC was detectable. The arrow indicates the expected molecular weight for FanC, as estimated from molecular weight standards and a histidine-tagged recombinant FanC run on the same gel. Protein in lanes 1 (30 μg) and 4 (100 μg) was derived from the non-processed control. Protein in lanes 2 (30 μg) and 4 (100 μg) was derived from soy protein powder formulations. Protein in lanes 3 (30 μg) and 6 (100 μg) was derived from soymilk formulations. Surprisingly, processing of soybean seed into soy-enriched powder or soymilk did not appear to significantly impact the stability of the FanC antigen.

FIG. 16 shows the stability of FanC antigen in dried soybean leaves stored for 2 years at room temperature. $T_0$ transgenic leaves from lines 485-1 and 485-10 were air dried, ground to a powder, and stored in a 50 ml conical tube at room temperature on a laboratory shelf for 24 months. After 24 months, protein was extracted from the dried leaf material and quantified using the Bradford protein assay. Fifteen micrograms of protein from each line was then subjected to SDS-PAGE and Western analysis, as previously described (Piller et al 2005. 222, 6.). Known concentrations of recombinant histidine tagged FanC (6×FanC) were included as a standard. This result clearly shows that the FanC antigen can be stored for prolonged periods of time in a stable form in dried leaves.

Expression of Heat Labile Toxin of *E. coli*, LT(R192G) in Transienic Soybeans

In another embodiment, the A and B subunits of a mutant form of LT in transgenic soybeans were expressed (FIG. 12). The ability to express the A and B subunits of a mutant form of LT in transgenic soybeans shows the generality of the procedure and demonstrates that a plurality of immunogens are likely to be able to be expressed in soybeans.

Prophylactic Therapy Approach

In an embodiment of the invention, prophylactic therapy to prevent the development of hypersensitivity to the bee venom allergen, phospholipase A2 (Api ml) in neonatal and adolescent mice is likely to be successful. To accomplish this task, allergen(s) in a soy powder or soy milk formulations are expressed which can be administered orally to weanling mice to induce systemic tolerance which lasts into adulthood. Specifically, the bee venom allergen (phospholipase A2) is expressed in transgenic soybeans. Soy protein or soy milk preparations from these transgenic soybeans is then given orally to weanling mice prior to sensitization. The ability to induce allergic reactions in these tolerized animals is then assessed.

The plantlets are grown and then transferred to soil, grown to maturity, and allowed to set $T_1$ seed in the greenhouse. In short, the $T_1$ seeds derived from T0 plant lines are screened to determine whether the gene encoding bee venom phospholipase A2 (H34Q) is expressed in seeds of the surviving, herbicide-resistant transgenic plants.

When $T_1$ seeds become available, the transgenic events expressing high levels of bee venom phospholipase A2 (H34Q) are identified. The best T1 seeds are then propagated to obtain $T_2$ seeds. The $T_1$ seeds are harvested from all herbicide resistant lines. The seeds are earmarked for possible future propagation to $T_1$ plant growth, and the remainder of the seeds are processed for DNA and RNA. Genomic DNA isolated from $T_1$ seeds and from control seeds is used in duplex PCR to verify stable integration of the bee venom phospholipase A2 (H34Q) expression cassette. For those DNA samples which are positive, the RNA is subjected to RT-PCR to demonstrate the presence of message expression and confirm the results of the DNA analyses. A Southern analysis is performed to determine copy number and locus number of the bee venom phospholipase A2 (H34Q) expression cassette. The genomic DNA is isolated from transgenic and control tissues, digested with a restriction enzyme that cleaves once within the T-DNA (such as BamHI), electrophoresed in agarose gels, denatured, and mobilized onto membranes that undergoes hybridization with a 32P-labelled bee venom phospholipase A2 (H34Q) probe. Autoradiography is then used to visualize the number of bee venom phospholipase A2 (H34Q) loci within each event. Events that accumulate the greatest levels of bee venom phospholipase A2 (H34Q) are propagated. If both, high complexity and low complexity events show similar accumulation of PLA2 (H34Q), the preference is to move the low complexity events forward.

$T_1$ Plant Growth and $T_2$ Seed Screening

Using information from the $T_1$ seed screens, the three lines with the best molecular profile and which express the greatest levels of bee venom phospholipase A2 (H34Q) are propagated for $T_1$ plant growth. The $T_2$ seeds are collected and screened to: 1) identify transgenic lines in a segregating population; 2) verify stable inheritance of the bee venom phospholipase A2 (H34Q) gene and bee venom phospholipase A2 (H34Q) expression; 3) increase the number of transgenic soybean seeds available for subsequent studies; and 4) identify lines that may have reached homozygosity for the transgenic locus. These screens employ duplex PCR, ELISA, Western, and Southern analyses as described above. Bee venom phospholipase A2 (H34Q) levels of >1.0% of seed TSP are expected when bee venom phospholipase A2 (H34Q) is targeted specifically to the seed.

Recombinant Bee Venom Phospholipase A2 (H34Q) Expression in *E. coli*.

For use in ELISAs, Western blot analyses, and as an immunogen for making antibodies, bee venom phospholipase A2 (H34Q) in *E. coli* is cloned and expressed. Expression of recombinant proteins, their purification, and characterization is routine. Synthetic bee venom phospholipase A2 (H34Q), optimized for expression in prokaryotes, is synthesized using overlapping primers and PCR. A histidine tag (or possibly a GST tag or some other tag) is incorporated into the synthetic gene to facilitate purification of the recombinant protein for subsequent use.

Polyclonal Antibody Production Against Recombinant Bee Venom Phospholipase A2 (H34Q)

For use in ELISAs and Western blot analyses, polyclonal antibodies are made against the *E. coli*-derived bee venom phospholipase A2 (H34Q) in rabbits using procedures known in the art. (See 86-89 for making polyclonal and monoclonal antibodies, purifying immunoglobulins, and developing immunoassays using antibodies).

Bee Venom Phospholipase A2 (H34Q) Stability in Soy Formulations:

Once $T_2$ seeds have been screened to demonstrate the lines that need to be expanded for $T_2$ plant growth, some of the $T_2$ seeds are used to demonstrate, and confirm, the stability of bee venom phospholipase A2 (H34Q) in the soy protein and soy milk formulations. For these studies, soy protein and soy milk formulations are made using transgenic $T_2$ seeds as described below. Western blot analyses are used to demonstrate intact allergen present in the two formulations. ELISAs are used to quantify the amount of allergen present in seeds and in each soybean formulation on a per-weight basis and per total protein. As is shown for FanC (see FIG. 4 page 25), the bee venom phospholipase A2 (H34Q) expression in these soybean formulations is likely to remain intact.

$T_2$ Plant Growth and $T_3$ Seed Screening

Using the information from the $T_2$ seed screens, selected lines are expanded as $T_2$ plants which provides $T_3$ transgenic soybean seeds. Screening of the $T_3$ seeds and quantification of each plant line's ability to express bee venom phospholipase A2 (H34Q) protein is determined by ELISA and Western blot as described above for $T_2$ seeds.

Treatment of Weanling Mice with a Soy Protein Formulation from Transgenic Seeds Expressing Bee Venom Phospholipase A2 (H34Q) as a Prophylactic Therapy for Hypersensitivity.

Treatment of weanling mice with a soy protein formulation derived from transgenic seeds expressing bee venom phospholipase A2 (H34Q) is tested to see if the development of hypersensitivity against this allergen is established.

Weanling mice are allowed to consume soy protein powder made from transgenic soybeans expressing bee venom phospholipase A2 (H34Q). At an age of 44 days, sensitization by weekly subcutaneous injections of recombinant allergen in alum is begun. At an age of 93 days, mice are challenged with an intraperitoneal injection of recombinant allergen. Groups of mice are taken for analyses at the indicated days.

The Treatment of Weanling Mice

A soy protein formulation from $T_3$ transgenic seeds expressing bee venom phospholipase A2 (H34Q) (experimental) or from transgenic seeds expressing *E. coli* FanC (control) is made as follows. Transgenic seeds are dried at room temperature to a water content of approximately 10% and then hulls are removed. The dehulled seeds are ground to a powder and defatted using solvent extraction (5 parts hexane) and gentle stirring for 20 minutes. Removal of hexane by filtration and air drying is followed by solvent extraction with 100% ethanol at room temperature to reduce the carbohydrate content. The soy protein powder is then exposed to dry heat (90° C. for 10 minutes). Soy protein powder sufficient to complete an entire experimental protocol is prepared and stored, in aliquots, at −20° C. for use. Each lot of soy protein powder is assayed to quantify protein content and the amount of transgenic protein expressed per mg of powder.

Because mice readily eat whole soybean seeds, it is not necessary to make a soy protein powder for their consumption. However, this is to show the feasibility of translating such prophylactic therapy to children. While enumerable methods for preparing soy protein exist, the above outlined procedure produces a soy protein powder of 70%-80% protein. This formulation is considered a "medium to high" grade formulation and is acceptable for human consumption.

Consuming Soy Protein Formulation Containing Bee Venom Phospholipase A2 (H34Q):

At 22 days of age, CBA/J mice are weaned and housed individually. Starting at day 23, regular chow is taken from the mice, and the appropriate amount of soy protein powder is added to a rodent feeding bowl with an inverted lip. Such vessels allow mice access to the soy powder, but virtually eliminate loss of any powder from the bowl. Mice eat at their leisure and at the end of the day an accurate record can be kept of the amount consumed by each mouse. This treatment continues every other day up to day 41 of age, for a total of 9 treatments.

Prophylactic treatment of children with soybean-derived oral allergens should be a safe and efficacious method for preventing the development of hypersensitivity. The studies on mice that are young, and particularly on mice weanlings give results that are likely translatable results to children. Two previous studies have suggested that intragastric administration of antigen to neonates within the first 10 days of life is not an effective method of tolerance induction (Miller, et al. 1994. Eur J Immunol 24:1026. Strobel, et al. 1984. Pediatr Res 18:588, both of which are incorporated in their entirety by reference.). Therefore, in the instant invention, mice are studied that are not still suckling as suckling mice may not be an optimal age for tolerance induction.

Sensitization to Bee Venom Phospholipase A2 (H34Q):

At 44 days of age, CBA/J mice receive 0.1 microgram of *E. coli*-derived bee venom phospholipase A2 (H34Q) in 1 milligram of alum subcutaneously. This sensitization continues every other week for a total of five treatments. This regimen results in the induction of high levels of allergen-specific IgE and, therefore, the sensitization of normal CBA/J mice to bee venom phospholipase A2 (Astori, et al. 2000. J Immunol 165:3497. von Garnier, et al. 2000. Eur J Immunol 30:1638., Jilek, et al. 2001. J Immunol 166:3612., Seeger, et al. 1998. Eur J Immunol 28:2124. Von Garnier, et al. 2002. Clin Exp Allergy 32:401, all of which are incorporated by reference in their entireties).

Challenge with Bee Venom Phospholipase A2 (H34Q)

Three weeks after the final sensitization injection, CBA/J mice at 121 days of age are challenged with allergen by injecting 30 micrograms of *E. coli*-derived bee venom phospholipase A2 (H34Q) intraperitoneally. This exposure induces an anaphylactic response in sensitized mice.

Table 1 shows the number of mice per group, the treatment groups, and the number of mice to be taken for each of the assay groups. A low dose (1 mg per day) and a high dose (5 mg per day) of soy protein powder expressing bee venom phospholipase A2 (H34Q) is used in this experimental protocol.

A 500 microgram dose represents the amount of bee venom phospholipase A2 (H34Q) that is expressed in approximately 1 transgenic soybean seed, assuming that allergen expression is 1% of the total seed protein. Soybean seeds from this strain weigh about 150 milligrams and about 130 milligrams following dehulling. Therefore at 1% expression, each seed contains just over 500 micrograms of allergen. When processing to soy powder most of the fat and carbohydrates are lost, which accounts for about half of the weight of the dehulled seed. Therefore approximately 70 milligrams of soy protein powder are fed to obtain a 500 microgram dose. Based on these calculations, the amount of material needed is easy to obtain after isolating $T_3$ seeds. In addition, this amount of material is easily consumed by weanling mice during the course of the treatment days.

For control groups, mice are allowed to consume soy protein powder expressing *E. coli* FanC (Piller et al. Planta, 222, 6) or normal laboratory chow (which contains soy 15 protein but no FanC) for comparison.

Table 9: Groups of mice to be treated with soybean-derived bee venom phospholipase A2 (H34Q).

TABLE 9

Groups of mice to be treated with soybean-derived bee venom phospholipase A2 (H34Q).

| Total number of mice treated | Treatment (amount of allergen in soy protein formula per day) | Number of mice taken for Group #1 analyses | Number of mice taken for Group #2 analyses | Number of mice taken for Group #3 analyses |
|---|---|---|---|---|
| 12 | Soy protein powder containing phospholipase (1 mg) | 4 | 4 | 4 |
| 12 | Soy protein powder containing phospholipase (5 mg) | 4 | 4 | 4 |
| 12 | Soy protein powder containing FanC (5 mg) | 4 | 4 | 4 |
| 12 | None (regular laboratory chow) | 4 | 4 | 4 |
| 4 | *E. coli*-derived phospholipase in CFA given intraperitoneally | 4 | 0 | 0 |

The relevant question is: does consumption of soy protein powder containing bee venom phospholipase A2 (H34Q), by itself, result in sensitization of mice? At day 44 when mice have completed their consumption of soy protein powder containing bee venom phospholipase A2 (H34Q), four mice each from the experimental and control groups are sacrificed to determine if allergen specific antibodies or if antigen-specific CD4+ T cell responses are present. To investigate the presence of any anti-bee venom phospholipase A2 antibody responses, ELISA, ELISpot and antigen-specific proliferation analyses are performed. This entire experimental design is performed twice to assure data reproducibility.

ELISA for allergen-specific serum and mucosal antibodies: For ELISA, *E. coli*-derived allergen is coated onto ELISA plates. Sera and fecal samples collected from the euthanized mice are used to quantify serum IgG1, IgG2a, and IgE and mucosal IgA antibody levels against bee venom phospholipase A2. Fecal IgA antibodies are isolated as previously described (Takahashi, et al. 1996. J Infect Dis 173:627, which is herein incorporated by reference in its entirety.).

ELISpot Analyses for Quantification of Allergen-specific Antibody Forming Cells

To quantify numbers of allergen-specific antibody forming cells, mononuclear leukocytes are isolated from the spleens and mesenteric lymph nodes of mice. Triplicate limiting dilutions ($5 \times 10^5$ to $10^4$ cells per well) are plated onto MultiScreen-IP microtiter plates (Millipore, Inc.) that have been previously coated with E. coli-derived recombinant bee venom phospholipase A2 (H34Q). After 48 hours at 37° C. in a CO2 incubator, wells are washed, and alkaline phosphatase-conjugated anti-mouse isotype specific (IgG1, IgG2a, IgA, and IgE, respectively) antibodies are added. After washing, substrate is added to visualize spot forming cells. An automated ImmunoSpot Reader (Cellular Technologies, Ltd., Becton Dickinson) with dedicated software can be used to facilitate data acquisition and analysis.

ELISpot Analyses for Quantification of Allergen-specific CD4+ T Cell Responses:

To investigate the presence of any CD4+ T cell responses in mice who have been allowed to consume soy protein powder containing bee venom phospholipase A2 (H34Q), ELISpot analyses are performed. Mononuclear leukocytes are isolated from the spleens of mice, followed by positive magnetic separation (MACS, Miltenyi, Inc.) for CD4+ lymphocytes as previously described (Peacock, et al. 2001. Immunology 104: 109., Elhofy, et al. 2000. J Immunol 165:3324., Lin, et al. 2004. Biochem Biophys Res Commun 321:828. Elsawa, et al. 2003. J Immunol 170:2605, all of which are incorporated by reference in their entireties.). The MACS procedure for isolation of CD4+ T lymphocyte subpopulations routinely gives greater than 93% purification as indicated by FACS analysis. Triplicate limiting dilutions of the appropriate T cell subpopulations ($1 \times 10^5$ to $10^3$ cells per well) are plated onto MultiScreen-IP microtiter plates (Millipore, Inc.) that have been previously coated with a capture monoclonal antibody against mouse IFN-g, IL-4 or IL-10 (BD Pharmingen). To serve as antigen presenting cells, $10^5$ bone marrow-derived dendritic cells per well, that have been pulsed with E. coli-derived bee venom phospholipase A2 (H34Q) (10 micrograms per $10^5$ cells), are added. Bone marrow derived dendritic cells are used as antigen presenting cells in the ELISpot re-stimulation assays, and these antigen presenting cells are generated as previously described (Nelson, et al. 2004. J Neuroimmunol 155:94. Son, et al. 2002. J Immunol Methods 262:145, both of which are incorporated by reference in their entireties.). After 48 hours of re-stimulation, ELISpot analyses are performed for production of IFN-gamma, IL-4, and/or IL-10 (BD Pharmingen ELISPOT kits). An ImmunoSpot Reader (Cellular Technologies, Ltd., Becton Dickinson) with dedicated computer and software for analysis of spot size distribution facilitates data acquisition and analysis.

CD4+ T Cell Proliferation Assays

To investigate the ability of CD4+ T cells to proliferate in response to allergen, tritiated thymidine incorporation assays are performed. Mononuclear leukocytes are isolated from the spleens of mice, followed by positive magnetic separation for CD4+ lymphocytes as previously described (Peacock et al. 2001. Immunology 104:109, Elhofy, et al. 2000. J Immunol 165:3324., Lin, et al. 2004. Biochem Biophys Res Commun 321:828. Elsawa, et al. 2003. J Immunol 170:2605, all of which are incorporated by reference in their entireties.). Triplicate limiting dilutions of the CD4+ T cell subpopulations ($1 \times 10^5$ to $10^4$ cells per well) are plated into round bottom 96 well plates. To serve as antigen presenting cells, $10^5$ bone marrow-derived dendritic cells per well, that have been pulsed with E. coli-derived bee venom phospholipase A2 (H34Q) (10 micrograms per $10^5$ cells), are added. Bone marrow derived dendritic cells are used as antigen presenting cells in the proliferation assays, and these antigen presenting cells are generated as previously described (Nelson, et al. 2004. J Neuroimmunol 155:94. Son, et al. 2002. J Immunol Methods 262:145). Plates are cultured at 37° C. in a $CO_2$ incubator for 72 hours with the final 24 hours being in the presence of 0.5 microcurries per well of tritiated thymidine. Cells are harvested (PHD Cell Harvester, Brandel) and incorporation of radioactivity determined.

Statistical Analyses

Statistical analyses are performed on the results from ELISA, ELISpot, and proliferation analyses by one-way ANOVA using a Bonferroni post hoc test for comparison of means (GraphPad, San Diego, Calif.).

To serve as positive controls for these assays (see Table 9), four additional mice are immunized intraperitoneally with 200 micrograms of E. coli-derived bee venom phospholipase A2 emulsified in complete Freund's adjuvant (CFA). Sera and cells from these immunized mice are taken 14 days later, to coincide with the euthanasia of the other mice that are 44 days of age.

To determine if weanling mice that have consumed soy protein powder containing bee venom phospholipase A2 (H34Q) are tolerant to a sensitization regimen the following experiment can be performed. At 114 days of age, two weeks after mice have received their last sensitization injection, four mice each from the experimental and control groups (see Table 9) are sacrificed to determine the level of allergen-specific antibodies or antigen-specific CD4+ T cell responses which are present. Analyses to be performed include: 1) ELISA for allergen-specific serum and mucosal antibodies; 2) ELISpot analyses for quantification of allergen-specific antibody forming cells; 3) ELISpot analyses for quantification of allergen-specific CD4+ T cell responses; and 4) CD4+ T cell proliferation assays, using the methods described above.

Mice that have been allowed to consume soy protein powder containing bee venom phospholipase A2 (H34Q) should have: 1) a reduced allergen-specific IgG1 and IgE antibody levels, with a possible skewing toward an IgG2a and IgA response; 2) reduced numbers of IgG1 and IgE allergen-specific antibody spot forming cells, with a possible skewing toward an IgG2a and IgA response; 3) a reduced number of allergen-specific CD4+ T cells secreting IL-4, with an increased number of IFN-gamma and IL-10 spot forming cells; and 4) a decrease in the allergen-induced proliferation of CD4+ T lymphocytes; when compared to mice who have been allowed to consume soy protein powder containing *E. coli* FanC or regular laboratory chow.

To determine if weanling mice, that have consumed soy protein powder containing bee venom phospholipase A2 (H34Q), are tolerant to challenge with an anaphylactic dose of allergen the following experiment can be performed.

At 121 days of age, three weeks after mice have received their last sensitization injection, four mice each from the experimental and control groups (see Table 9) are challenged with an anaphylactic dose of allergen. The primary goal of this challenge is to determine whether mice can survive the anaphylactic response. Mice are treated and observed individually. When it is clear that a particular mouse succumbs to this systemic hypersensitivity reaction, they are euthanized. Following challenge, tissues from all mice, regardless of clinical response, are taken to determine the level of allergen-specific antibodies or antigen-specific CD4+ T cell responses which are present. Analyses performed include: 1) ELISA for allergen-specific serum and mucosal antibodies; 2) ELISpot analyses for quantification of allergen-specific antibody forming cells; 3) ELISpot analyses for quantification of allergen-specific CD4+ T cell responses; and 4) CD4+ T cell proliferation assays, using the methods described above.

Mice treated orally with soybean-derived FanC or allowed to consume regular laboratory chow should succumb to anaphylactic shock when given the intraperitoneal injection. In contrast, mice treated orally with soybean-derived bee venom phospholipase A2 (H34Q) should survive. For the antibody and cellular analyses, similar results should occur as observed for the analyses of weanling mice that have consumed soy protein powder containing bee venom phospholipase A2 (H34Q). In fact, these studies should indicate that the effects of prophylactic treatment with oral allergen can last well into adulthood of these mice.

These results would strongly support the notion that it is possible to prevent the development of an allergic phenotype by prophylactic therapy in weanling animals.

Treatment of Weanling Mice with a Soy Milk Formulation from Transgenic Seeds Expressing Bee Venom Phospholipase A2 (H34Q) as a Prophylactic Therapy for Hypersensitivity In an embodiment, an additional set of studies are performed to assess the efficacy of continuous feeding soy milk derived from transgenic seeds expressing bee venom phospholipase A2 (H34Q). There is some indication that continuous feeding of an antigen is an efficacious method for the induction of oral tolerance (Faria, et al. 2003. J Autoimmun 20:135, which is herein incorporated by reference in its entirety.). This supports the notion of prophylactic therapy of children to limit the development of hypersensitivities.

A soy milk formulation from $T_3$ transgenic seeds expressing bee venom phospholipase A2 (H34Q) (experimental) or from transgenic seeds expressing *E. coli* FanC (control) is made as follows. $T_3$ transgenic soybean seeds are placed into an automated processor (SoyQuick Soy Milk Maker) to make soy milk. Typically, the concentration of soy protein in such aqueous formulations is approximately 40 milligrams per milliliter of milk. Therefore, assuming that allergen expression in transgenic seeds is 1% of total protein, each milliliter of milk contains approximately 400 micrograms of allergen. The exact concentration of allergen in each batch of soy milk is determined per milliliter and per concentration of protein using an ELISA assay. Aliquots of soy milk are stored at −20° C. until given to mice.

Consuming Soy Milk Containing Bee Venom Phospholipase A2 (H34Q)

At 22 days of age, CBA/J mice are weaned and housed individually. Starting at day 23, water is replaced with soy milk in a graduated tube which allows the amount of milk consumed to be recorded each day. Fresh soy milk is given daily through 41 days of age.

The sensitization to bee venom phospholipase A2 (H34Q and the challenge with bee venom phospholipase A2 (H34Q) is similar to the procedure described above.

Table 10 shows the number of mice per group, the treatment groups, and the number of mice to be taken for each of the assay groups. For control groups, mice allowed to drink soy milk expressing *E. coli* FanC (Piller et al. 2005 Planta, 222, 6) or water are used as controls for comparison.

TABLE 10

| Groups of mice to be treated with soybean-derived bee venom phospholipase A2 (H34Q). | | | | |
|---|---|---|---|---|
| Total number of mice treated | Treatment (amount of allergen in soy milk formula per milliliter) | Number of mice taken for Group #1 analyses 44 days | Number of mice taken for Group #2 analyses 114 days | Number of mice taken for Group #3 analyses 121 days |
| 12 | Soy milk (approximately 350 micrograms/ml phospholipase) | 4 | 4 | 4 |
| 12 | Soy milk (approximately 350 micrograms/ml FanC) | 4 | 4 | 4 |
| 12 | None (water) | 4 | 4 | 4 |
| 4 | *E. coli*-derived phospholipase in CFA given intraperitoneally | 4 | 0 | 0 |

Group #1 Analyses: Does Consumption of Soy Milk Containing Bee Venom Phospholipase A2 (H34Q), by itself, Result in Sensitization of Mice?

At day 44 when mice have completed their consumption of soy milk containing bee venom phospholipase A2 (H34Q), four mice each from the experimental and control groups are sacrificed to determine if allergen specific antibodies or if antigen-specific CD4+ T cell responses are present. To investigate the presence of any anti-bee venom phospholipase A2 antibody responses, ELISA, ELISpot and antigen-specific proliferation analyses are performed. This entire experimental design is performed twice to assure reproducibility of the data obtained. Furthermore, the methods are identical to those described above.

Group #2 Analyses: Are Weanling Mice, that have Consumed Soy Milk Containing Bee Venom Phospholipase A2 (H34Q), Tolerant to the Subsequent Sensitization Regimen?

At 114 days of age, two weeks after mice have received their last sensitization injection, four mice each from the experimental and control groups (see Table 10) are sacrificed to determine the level of allergen-specific antibodies or antigen-specific CD4+ T cell responses which are present. Analyses performed include: 1) ELISA for allergen-specific serum and mucosal antibodies; 2) ELISpot analyses for quantification of allergen-specific antibody forming cells; 3) ELISpot analyses for quantification of allergen-specific CD4+ T cell responses; and 4) CD4+ T cell proliferation assays, using methods described above. Furthermore, the methods are identical to those described above.

Group #3 Analyses: Are Weanling Mice, that have Consumed Soy Milk Containing Bee Venom Phospholipase A2 (H34Q), Tolerant to Challenge with a Anaphylactic Dose of Allergen?

At 121 days of age, three weeks after mice have received their last sensitization injection, four mice each from the experimental and control groups (see Table 10) are challenged with an anaphylactic dose of allergen. The primary goal of this challenge is to determine whether mice survive the anaphylactic response. Mice are treated and observed individually. When it is clear that a particular mouse succumbs to this reaction, they are euthanized to determine the level of allergen-specific antibodies or antigen-specific CD4+ T cell responses which are present. Analyses performed include: 1) ELISA for allergen-specific serum and mucosal antibodies; 2) ELISpot analyses for quantification of allergen-specific antibody forming cells; 3) ELISpot analyses for quantification of allergen-specific CD4+ T cell responses; and 4) CD4+ T cell proliferation assays, using methods described above.

It is likely that the processing of soybeans to protein powder or to soy milk does not destroy the bee venom phospholipase A2 (H34Q) expressed in seeds. The stability of FanC, of similar size (see above and below) has already been demonstrated. An advantage of the present invention is that allergen does not need to be purified, but only goes through a simple, and relatively gentle processing of the soybeans to obtain soy protein powder or soy milk, which can be readily consumed by humans. Therefore, it is likely that the mild processing does not destroy the allergen.

Degradation of allergen in the gastrointestinal tract is also not likely to be a limiting factor because the present invention gives a very high allergen load. Furthermore, the soy formulations contain high levels of protein that likely provide stability. Even if there is some degradation of the bee venom phospholipase A2 (H34Q), peptide fragments also might be able to contribute to tolerance induction as epitopes may still be present on these peptide fragments.

Construction of Synthetic FanC and Plant Transformation Vectors

A synthetic plant-optimized version of fanC was created by sequential pair-wise annealing and extension of 70- to 100-bp-long complimentary oligonucleotides. Four 20-µl reactions, each containing 10 pmol of the complementary oligonucleotide pairs indicated, were assembled on ice: reaction A contained

```
FanC-1
                                              SEQ ID NO: 1
(TCATGAATACAGGCACTATCAACTTTAACGGAAAGATTACTTCCGCGAC
GTGCACAATCGAC CCCGAGGTGAACGGAAATCG)

plus FanC-8
                                              SEQ ID NO: 8
(CTTGAGCTTAAAGTCTACAACCGTGCCGTGTCCACTGATCGCGGCTGG
CCCAGGTCGATAGTGGATGTGCGATTTCCGTTCACCTCGGGGTCGATTGT
G);

reaction B contained FanC-2
                                              SEQ ID NO: 2
(CACGGCACGGTTGTAGACTTTAAGCTCAAGCCAGCCCCTGGCTCTAACG
ACTGCTTGGCCAAGACAAACGCTCGGATTGACTGGTCGGGCTCG ATGAA
CT)

plus FanC-7
                                              SEQ ID NO: 7
(GCAGCGGTATTGCCGCTAGCAGTGTTATTGAATCCAAGCGAGTTCATCG
AGCCCGACCAGTCAATCCGA);

reaction C contained FanC-3
                                              SEQ ID NO: 3
(CAATAACACTGCTAGCGGCAATACCGCTGCCAAAGGGTATCACATGACC
CTACGTGCGACTAACGTGGGA)

plus FanC-6
                                              SEQ ID NO: 6
(AGTGTGGGTGTATTCCGCCGTGGTGAATGAAGTGTTGATGTTCGCACCA
CCACTACCGTTTCCCACGTTAGTCGCACGTAGGGTCATGTG),
and reaction D contained FanC-4
                                              SEQ ID NO: 4
(TCATTCACCACGGCGGAATACACCCACACTTCGGCTATACAGTCCTTCA
ACTATTCCGCCCAACTTAAGAAAGACGATAGGGCACCTTCTAACGGAGGG
T)
```

```
plus FanC-5
                                              SEQ ID NO: 5
(TCTAGAGCT CGTCCTWCATATAGGTCACGA GGAATGACGCGCTGGTC
GTGAAGACTCCCGCCTTATACCCTCCGTTAGAAGGTGCCCTATCGTCTT)
```

Because the gene oligosequences were synthesized on a gene machine, it should be understood by those of skill in the art that modifications to protein sequences (for example, site directed mutagenesis) can be easily accomplished by modifying the nucleotide sequence. Each of the above reactions also contained 50 mM NaCl, 10 mM Tris-HCl (pH 7.9), 10 mM MgCl2, 1 mM dithiolthreitol (DTT), 1 mM dNTPs, and 0.1 mg/ml bovine serum albumin (BSA). Reactions were heated to 94° C. for 5 min and then annealed at 60° C. for 5 min. Three units of T4 DNA polymerase were then added to each reaction, and extensions proceeded for 15 min at 14° C. The above heating-annealing-extension cycle was repeated a second time with the addition of 3 units of fresh T4 DNA polymerase before the extension step. Reactions A and B, and reactions C and D were combined to make reactions E and F, respectively. Heating, annealing, and extension of reactions E and F were carried out for two cycles as described above with fresh enzyme added prior to the extension. Reactions E and F were combined to make reaction G, which was again subjected to the cycle regimen described above. The template in reaction G was further amplified using primers

```
Fanc-9
                                              SEQ ID NO: 9
(GCCCTTTCATGAAT ACAGGCAC)
and FanC-10
                                              SEQ ID NO: 10
(GCTCTAGAGCTCGTCCTTCATATAGG).
```

PCR reactions (50 µl) contained 50 pmol of primer (FanC-9 and FanC-10), 5 µl of template G, 0.2 mM dNTPs, and 5 units of Pfu DNA polymerase (Stratagene, LaJolla, Calif., USA) in buffer recommended by the manufacturer. Reactions were denatured at 94° C. for 3 min, and then cycled 25 times (94° C. denaturation for 45 s, 60° C. annealing for 30 s, 72° C. extension for 1 min) in a Stratagene Robocycler. Following PCR, 5 units of Taq DNA polymerase (Promega, Madison, Wis., USA) was added to each tube and reactions were incubated at 72° C. for 10 min to allow 3' terminal addition of A residues to PCR-amplified products. The products were subcloned into pCR2.1-TOPO using the TOPO TA cloning kit (Invitrogen, Carlsbad, Calif., USA) creating the intermediate plasmid pKP3. SynfanC was isolated from pKP3 as a BspHI-XbaI fragment, and ligated into pRTL2 (Carrington et al. 1990 J Virol 64:1590-1597, which is herein incorporated by reference in its entirety) digested with NcoI and XbaI to create the intermediate plasmid pKP5. The synFanC plant expression cassette was isolated from pKP5 as a HindIII fragment and ligated into the binary vector pPTN200, a derivative of pPZP202 (Hajdukiewicz et al. 1994 Plant Mol Biol 25:989-994, which is herein incorporated by reference in its entirety) that harbors a bar gene (Thompson et al 1987 EMBO J 6:2519-2523, which is herein incorporated by reference in its entirety), to create pKP7. Plasmid DNA was isolated and purified using Qiagen Plasmid Isolation kits (Qiagen, Valencia, Calif., USA), and the integrity of pKP7 was verified by double-stranded sequencing (Davis Sequencing, LLC, Davis, Calif., USA).

Soybean Transformations

The binary vector pKP7 was mobilized into *Agrobacterium tumefaciens* strain EHA101 (Hood et al. 1986 J Bacteriol 168:1291-1301, which is herein incorporated by reference in its entirety) by triparental mating (Ditta et al. 1980 Proc Natl Acad Sci USA 77:7347-7351, which is herein incorporated by reference in its entirety). Soybean (Glycine max Merr) genotype Thorne (Ohio State University) was used for transformation with the above resultant transconjugant as previously described (Clemente et al. 2000, Crop Sci 40:797-803; Zhang et al. 1999, Plant Cell Tissue Organ Cult 56:37-46, both of which are incorporated by reference in their entireties). Glufosinate was used as the selective agent at concentrations of 5 mg/ml and 3 mg/ml during shoot initiation and elongation steps, respectively. Following regeneration, young plantlets were transplanted to soil and maintained in a greenhouse. After approximately 4 weeks in soil, a leaf trifoliate was isolated for use in nucleic acid and protein characterizations.

Molecular Characterization of Transgenic Plants

Soybean leaf tissue and seeds were frozen in liquid nitrogen and ground to a fine powder using a mortar and pestle. Genomic DNA was isolated using DNEasy Plant Kit (Qiagen). For duplex PCR reactions, approximately 1 µg of genomic DNA was mixed with FanC-9, FanC-10, VSP-1 (5'-GCTTCCACACATGGGAGCAG-3') SEQ ID NO: 17, and VSP-2 (5'-CCTCTGTGGTCTCCAAGCAG3') SEQ ID NO: 18. Reactions were denatured at 95° C. for 5 min, followed by 32 cycles of denaturation (95° C. for 30 s), annealing (58° C. for 1 min), and extension (72° C. for 1 min), and visualized in 1.5% agarose gels. For Southern analysis, genomic DNA was digested with BamHI, separated by agarose gel electrophoresis, and transferred onto a nitrocellulose membrane. Membranes were then probed with a 32 P-labeled FanC probe for 16 h, washed, and exposed for autoradiography as previously described (Sato et al. 2004, Crop Sci 44:646-652, which is incorporated by reference in its entirety). For Western analysis, soluble protein was extracted from ground tissue using soybean extraction buffer (SEB, 25 mM Tris-HCl [pH 8.0], 1 mM EDTA, 5 mM DTT; 5 ml/g ground tissue) and sonication (10-s pulses for a total of 1 min at 4° C.). Sonicated samples were clarified by centrifugation at 16,000 rcf for 30 min at 4° C., and quantified with the Bradford reagent (Bio-Rad) against a BSA standard. Proteins were separated in 10% SDS-PAGE gels, and transferred in 10 mM CAPs buffer (pH 11) to Immobilon-P membrane (Millipore, Bedford, Mass., USA). Following an overnight blocking reaction at room temperature in PBS containing 5% non-fat powdered milk, rabbit anti-K99 serum (1:2,000) was added to fresh block solution, and incubations were carried out for 1-2 h at room temperature. Membranes were washed twice in PBS containing 0.02% Tween (PBST) for 15 min each at room temperature, and then incubated for 1 h with a goat anti-rabbit immunoglobulin antibody conjugated with horseradish peroxidase (Cell Signaling Technology) in blocking solution. Following two additional washes with PBST, immunodetection was carried out using the SuperSignal West Pico Chemiluminescent Substrate kit (Pierce, Rockford, Ill., USA), and bands were visualized with a BioMax film (Kodak, Rochester, N.Y., USA).

Purification of Recombinant FanC

Recombinant FanC was produced and purified as a MalE-FanC fusion protein. The plasmid harboring the fusion protein was created by PCR amplification of native fanC (Ascon et al. 1998, Infect Immun 66:5470-5476, which is incorporated by reference in its entirety) with the primers FanC-11 (5'-ATGGATCCAATACAGGTACTATTAAC-3') SEQ ID NO: 11 and FanC-12 (5'-ATTCTAGACATATAAGTGAC-TAAGAAGGA-3') SEQ ID NO: 12, digestion of the PCR product with BamHI and XbaI, and ligation into the pMAL-c2 expression vector (New England Biolabs) creating pMalE-FanC. Bacteria harboring pMalE-FanC were grown in LB at 37° C. to a density of OD600=0.5. Expression of the fusion protein was induced with 1 mM isopropyl-b-D-thiogalactoside (IPTG), and bacterial cells were grown for an additional 2 h at 37° C. Recombinant MalE-FanC fusion protein was isolated in accordance with the manufacturer's protocol.

Immunohistochemistry and Histochemical Staining

Leaf tissue was fixed in 100 mM potassium phosphate containing 1.5% paraformaldehyde, and 0.2% glutaraldehyde (pH 7.0) overnight at 4° C. The fixed tissue was processed by dehydration with increasing concentrations of ethanol [50%, 70%, 80%, 95% (·2), and 100% (·3)] for 30 min each, followed by treatment with Citrisolv (30 min ·3) and paraffin (45 min ·2). The tissue was then embedded in paraffin blocks, sectioned at 10-µm thickness, and placed onto glass slides. Slides were heated to 60° C. for 20 min to melt paraffin and then passed through a Citrisolv clearing agent (3· for 5 min each). The tissues were rehydrated by incubation with decreasing concentrations of ethanol (100%, 95%, 80%, and 70%) for 5 min each, followed by a rinse with PBS containing 3% BSA. Following an overnight block in PBS supplemented with 3% BSA and 50 µl/ml goat sera, the tissue was incubated with rabbit anti-K99 serum (1:100 dilution) for 3 h at RT, followed by an Alexaflour goat anti-rabbit IgG-HRP conjugated secondary antibody (1:500) for 1 h at RT. Cover slips were added to the sections using Gel/Mount aqueous mounting media, and sections were viewed at 20· using confocal imaging. For standard histochemical staining, the tissue was fixed and processed as described above. Slides were then stained with Gills hematoxylin for 15 min, rinsed in dH20, and immersed in 0.25% ammonium hydroxide for 1 min. Slides were then stained with eosin for 1 min followed by 1-min incubations with increasing concentrations of ethanol (80, 95, and 100%). Finally, slides were washed three times for 1 min each in Citrisolv.

Immunization of Mice with Soybean-derived K99 Protein Lysates

Groups of C57BL/6 mice (Jackson Laboratories) were untreated or were immunized intraperitoneally with transgenic protein lysate containing 382 ng of synFanC emulsified in complete Freund's adjuvant. Ten days following immunization, mice received a second equivalent immunization of transgenic protein lysate emulsified in incomplete Freund's adjuvant. Twenty-one days after the initial immunization, mice were euthanized and sera and splenic leukocytes isolated for quantification of antibody titers and CD4+ T-cell responses against FanC. For comparison, an additional group of mice was immunized in an identical manner with rFanC fusion protein purified from *E. coli* lysates as described above. These mice received 300 ng of rFanC emulsified in complete Freund's adjuvant, and 10 days later received a booster of 300 ng rFanC emulsified in incomplete Freund's adjuvant. Twenty one days after the initial immunization, mice were euthanized and sera collected.

Quantification of Antibody Titers Against K99

Serum antibody titers against synFanC in groups of immunized mice were determined using an ELISA. For these studies, rFanC fusion protein, purified from *E. coli* as described above, was adsorbed to 96-well ELISA plates (Coming) overnight in 0.1 M bicarbonate buffer (pH 9.0). ELISA wells were blocked with phosphate-buffered saline containing 1% BSA for 2 h, followed by the incubation of serial 1:2 dilutions of sera taken from immunized and control mice. After washing, a goat antimouse immunoglobulin antibody conjugated with horseradish peroxidase (Southern Biotechnology, Birmingham, Ala., USA) was added. Following a 1-h incubation, the unbound antibody was washed off, and bound antibody was detected by addition of TMB substrate (BioFX Inc). Enzymatic reactions were stopped by the addition of 1 M $H_2SO_4$, and optical absorbances at 450 nm determined. Antibody titers in immunized mice were defined as the highest dilution of sera that still had an absorbance value twice that of values obtained from non-immunized mice.

Quantification of CD4+ T-lymphocyte Responses Against K99

The ability of CD4+ T lymphocytes from immunized mice to respond to synFanC was determined using an in vitro restimulation assay. Following euthanasia, CD4+ T lymphocytes were isolated from splenic leukocytes using magnetic activated cell sorting (Miltineyi Biotech, Auburn, Calif., USA) as previously described (Elhofy et al. 2000, J Immunol 165:3324-3332; Peacock and Bost 2001, Immunology 104: 109-117, both of which are incorporated by reference in their entireties). CD4+ T lymphocytes isolated from non-immunized mice, or from mice immunized with transgenic soybean protein lysates containing synFanC, were plated at $10^6$ cells per well in 96-well round bottom tissue culture plates (Corning).

To serve as antigen presenting cells, bone-marrow derived dendritic cells were isolated as previously described (Son et al. 2002, J Immunol Methods 262:145-157, which is incorporated by reference in its entirety). Briefly, femurs of C57BL/6 mice were flushed with RPMI-1640 containing 2% FCS to collect total bone marrow cells. Any spicules or bone matrix were allowed to settle and were removed. The total bone marrow cells were washed once, and resuspended in RPMI-1640 containing 12% FCS and 1,000 U/ml GM-CSF (BD Biosciences, Chicago, Ill., USA). Cells were fed every 2 days by adding 50% fresh media. After 5 days in culture, non-adherent cells were removed, washed, and resuspended in RPMI-1640 containing 12% FCS and 1,000 U/ml GM-CSF. After 3 days, the non-adherent dendritic cells were removed from the flask and washed. Recombinant FanC, purified from E. coli as described above, was added to the dendritic cells (450 ng per $10^6$ cells), and these $5·10^5$ antigen-pulsed cells per well were added to the 96-well plates already containing the isolated CD4+ T lymphocytes. Following a 4-day incubation of CD4+ T lymphocytes with FanC pulsed dendritic cells, culture supernates were removed to quantify interferon gamma secretion using an ELISA procedure that has been previously described (Elhofy et al. 2000). To assure that interferon gamma secretion was antigen specific, control cultures containing CD4+ T lymphocytes and dendritic cells but without FanC antigen, or CD4+ T lymphocytes and FanC antigen but without dendritic cells were also prepared concomitantly.

Anti-FanC Serum Titers in Mice Immunized with Transgenic Soybeans Expressing FanC.

Mice readily consume soybean seeds. When food is withheld overnight, the mice consume 1-2 seeds in 10 minutes. FIG. 15 shows Anti-FanC serum titers in immunized and control mice. Mice were fed two transgenic or wild type seeds on days 0, 7, 15, and 22. On day 29, serum was collected and 1:2 serum dilutions were used in an ELISA assay. Anti-FanC titers in mice immunized with transgenic seed (n=3) were greater than 1:3200 when compared to controls (i.e., a statistically significant two fold difference over control values).

C57BL/6 mice were given two transgenic soybean seeds (derived from lines 485-1 and 485-10), while control mice were given two non-transgenic, wild type soybean seeds. A dose of two seeds weighed approximately 250 mg. Both transgenic and wild type seeds had been stored for more than a year at 4° C. Mice readily consume soybean seeds and most of the seed material was consumed within 10 minutes. However, mice were allowed 1 hour per feeding, followed by gavage with 25 μg of cholera toxin adjuvant. Similar feedings and gavages took place on days 7, 15, and 22 for a total of four feedings. On day 29, serum was collected, and an ELISA was performed to examine anti-FanC titers in control and test mice. As shown in FIG. 15, anti-FanC titers were easily detectable in mice fed with transgenic soybean seeds expressing FanC, but not in controls. In fact, anti-FanC titers were greater than 1:3200 when compared to controls (i.e. a statistically significant two fold difference over control values).

Thus, in less than one month from the first feeding, substantial serum antibody levels were observed in mice allowed to eat whole transgenic soybeans expressing FanC.

Previous studies to compare the above results are few because plant-derived immunogens are often concentrated or purified before being given to individuals (and they are usually given parenterally or intranasally). A study by Arntzen and colleagues (1995, Science, 268:714-716) showed IgG titers of less than 1:1000 after allowing mice to eat 5,000 mg of transgenic potato on 4 separate occasions (see FIG. 3, Science 268:714-716, 1995, which is herein incorporated in its entirety by reference). In the instant study, mice ate only 250 mg of seeds on 4 separate occasions, and had anti-FanC titers greater than 1:3200. Thus, this invention provides strong evidence to support the use of transgenic soybeans as a method of choice for expression of plant-derived vaccines.

The transgenic seeds used in the instant invention contained cytosol-targeted FanC, which resulted in accumulated antigen of ~0.25% of the total seed protein. Such levels can likely be increased 4 fold or more with a "seed-targeted" antigen construct, which is within the purview of a person of skill in the art.

Antibody Titers in Mice Orally Immunized with Soybean Formulations Containing rFanC The efficacy of FanC as a mucosal antigen following oral administration of a soybean-derived formulation in mice was studied. FanC model antigen is immunogenic when administered orally, and a dose of 150 μg of antigen is sufficient to stimulate humoral and cellular immune responses. Preliminary data demonstrated that FanC was indeed immunogenic when administered intraperitoneally, and stimulated production of significant anti-FanC antibody titers and antigen-specific CD4+ T lymphocytes in spleens of immunized mice. In the instant invention, it was shown that mice immunized orally with soybean protein formulations containing 50-450 μg FanC also produce significant anti-FanC antibody titers and stimulate formation of antigen-specific CD4+ T lymphocytes. This demonstrates the immunogenicity of the FanC model antigen when administered via an oral route, and also supports the dosage formulations outlined above.

Groups of mice were orally gavaged with 10 μg soybean leaf protein containing 50, 150, or 450 μg of rFanC antigen and adjuvant (25 μg CT). For controls, groups of mice were orally gavaged with formulations containing soybean extract plus adjuvant or FanC antigen plus adjuvant. Mice were given booster formulations on days 21 and 35, and on day 53 serum and spleen tissues were collected. To determine whether immunized animals developed significant anti-FanC antibody titers, an ELISA was performed. Dilutions (1:2) of serum were incubated in wells coated with rFanC antigen, and a goat anti-mouse Ig-HRP-conjugated secondary antibody was used to detect the presence of anti-FanC antibodies. The titer of each animal was defined as the highest dilution of sera that still had an absorbance value twice that of background, and was plotted as a histogram for comparison. FIG. 8 shows the results.

FIG. 8 shows that significant anti-FanC titers were detected in mice from all three test groups that were orally gavaged with soybean extract containing rFanC antigen, but not in control mice gavaged with soybean extract alone. Notably, the anti-FanC titers detected in some of the mice from groups immunized with 150 µg or 450 µg of rFanC were similar to anti-FanC titers in control mice gavaged with 150 µg of FanC alone. These findings are significant for several reasons: First, the results demonstrate that FanC is immunogenic when administered via the oral route, complementing our previous studies in which immunogenicity was demonstrated following intraperitoneal injection. Second, the results show that 150 µg doses of FanC are capable of stimulating the immune response. Finally, the results suggest that soybean-based formulations containing FanC induce humoral responses that are similar to those induced by the FanC antigen alone, suggesting that soybean components does not negatively impact antigenicity.

FanC-specific CD4+ T Lymphocyte Responses in Orally Immunized Mice.

To characterize the cellular immune responses in the orally immunized mice, a re-stimulation assay was performed. CD4+ T lymphocytes were isolated from splenic leukocytes using magnetic activated cell sorting, and plated in 96-well round bottom tissue culture plates. To serve as antigen presenting cells, bone marrow-derived dendritic cells were pulsed with rFanC antigen and added to the wells containing the CD4+ T lymphocytes. Following incubation of the T lymphocytes with rFanC-pulsed dendritic cells, interferon gamma secretion was measured using an ELISA. To assure that interferon gamma secretion was antigen specific, control cultures containing CD4+ T lymphocytes and dendritic cells but without rFanC antigen, or CD4+ T lymphocytes and FanC antigen but without dendritic cells, were also done concomitantly. FIG. 9 shows the results.

FIG. 9 shows that significant interferon gamma production was induced by CD4+ T lymphocytes isolated from all mice orally gavaged with soybean protein containing rFanC, but not from lymphocytes isolated from mice gavaged with soybean protein alone. Notably, mice in the group given a 150 µg dose of FanC secreted the greatest levels of interferon gamma, followed by mice in the group given 450 µg and 50 µg doses of rFanC, respectively. These results are significant because they support that a dose of about 150 µg antigen generates the highest immunogenic response. However, although a dose of about 150 µg antigen gives a large response, it should be clear to those of ordinary skill in the art that this invention demonstrates that cellular immune responses are generated in all mice immunized with the antigen, even at low doses of 50 µg.

The present invention has been described generally and with an emphasis on particular embodiments. It should be apparent to those of ordinary skill in the art that modifications can be made to the above disclosure and still fit within the scope and spirit of the invention. It is intended, contemplated, and therefore within the scope of the invention to combine any of the plurality of different elements in each of the embodiments in the above disclosure with any other embodiment. Moreover, the list of references that are mentioned in the disclosure are herein incorporated by reference in their entirety. The invention is not to be limited by the disclosure above but rather is defined by the claims below.

We claim:

1. An immunogen comprising a transgenic soybean and a mutant cholera toxin adjuvant, wherein the transgenic soybean is transformed with an exogenous nucleotide sequence that expresses recombinant SEB (*Staphylococcus* enterotoxin B) and wherein said immunogen produces a protective immunogenic response upon oral administration to an animal.

2. The immunogen according to claim 1, wherein the transgenic soybean is transformed with the exogenous nucleotide sequence by *Agrobacterium* mediated transformation.

3. The immunogen according to claim 1, wherein the protective immunogenic response is selected from the group consisting of: A) memory T helper lymphocyte response; B) memory cytotoxic T lymphocyte response; and C) memory B lymphocyte response.

4. An immunogen comprising a soy product and a mutant cholera toxin adjuvant, wherein the soy product is selected from the group consisting of soybean seed, soy milk, soy powder, soy flour, and soy flakes; and wherein the soy product comprises recombinant SEB that was produced in transgenic soybeans.

5. A method of producing an immunogen comprising a transgenic soybean or soy protein product made therefrom and a mutant cholera toxin adjuvant, said method comprising:
transforming a soybean with an exogenous nucleotide sequence that expresses SEB; wherein the mutant cholera toxin adjuvant is coexpressed with the SEB or is added separately to the transgenic soybean or soy protein product.

6. The method of claim 5, further comprising a step wherein the SEB is processed into a soy protein product.

7. The method of claim 6, wherein the soy protein product is in a form selected from the group consisting of soybean seed, soy milk, soy powder, soy flour, and soy flakes.

8. The method of claim 7, wherein the exogenous nucleotide sequence is operationally linked to a seed specific promoter.

9. A method of prophylactically treating an individual with the immunogen of claim 1, wherein said immunogen produces a protective immunogenic response upon oral administration to said individual.

10. The method of claim 9, wherein SEB is coexpressed as a fusion protein with another protein or peptide which targets binding to epithelial cells in the gastrointestinal tract.

11. The method of claim 9, wherein the immunogen is administered in a soy protein product form selected from the group consisting of soybean seed, soy milk, soy powder, soy flour, and soy flakes.

12. The method of claim 5, wherein the step of transforming is carried out by transferring the exogenous nucleotide sequence into an *Agrobacterium*, and infecting a soybean plant with the *Agrobacterium* thereby transforming the soybean plant.

13. The immunogen according to claim 1, wherein the immunogen comprises a transgenic soybean that is transformed with the exogenous nucleotide sequence that expresses SEB and an exogenous nucleotide sequence that expresses the mutant cholera toxin adjuvant wherein said immunogen produces a protective immunogenic response upon oral administration to an animal.

14. The immunogen according to claim 1, wherein at least 1% of the total protein of the transgenic soybean comprises the protein antigen expressed from the exogenous nucleotide sequence.

15. The method of claim 5, further comprising a step wherein the SEB and the mutant cholera toxin co-expressed are processed into a soy protein product.

16. The method of claim 9, wherein the immunogen is administered in a soy milk form.

\* \* \* \* \*